US008569036B2

(12) United States Patent
Dicosimo et al.

(10) Patent No.: US 8,569,036 B2

(45) Date of Patent: Oct. 29, 2013

(54) IMMOBILIZED TAL BIOCATALYST FOR PRODUCTION OF PARA-HYDROXYCINNAMIC ACID

(75) Inventors: Robert Dicosimo, Chadds Ford, PA (US); Sharon L. Haynie, Philadelphia, PA (US); Lixuan Lisa Huang, Hockessin (DE); Fateme Sima Sariaslani, Wilmington, DE (US); Tina K. Van Dyk, Wilmington, DE (US); Robert J. Trotman, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 1154 days.

(21) Appl. No.: 11/485,575

(22) Filed: Jul. 12, 2006

(65) Prior Publication Data

US 2008/0032371 A1 Feb. 7, 2008

(51) Int. Cl.

| | |
|---|---|
| ***C12N 1/20*** | (2006.01) |
| ***C12N 9/88*** | (2006.01) |
| ***C12P 7/40*** | (2006.01) |
| ***C12P 7/24*** | (2006.01) |
| ***C07H 21/04*** | (2006.01) |

(52) U.S. Cl.

USPC ........ 435/252.3; 435/136; 435/147; 435/232; 536/23.2

(58) Field of Classification Search

USPC ............... 435/232, 419, 135, 252.33, 69.1, 6; 536/23.2

See application file for complete search history.

(56) References Cited

U.S. PATENT DOCUMENTS

| | | | | |
|---|---|---|---|---|
| 4,562,151 | A | 12/1985 | Kishore | |
| 5,705,618 | A | 1/1998 | Westcott et al. | |
| 6,368,837 | B1 | 4/2002 | Gatenby et al. | |
| 2002/0164728 | A1* | 11/2002 | DiCosimo et al. | 435/128 |
| 2004/0059103 | A1 | 3/2004 | Huang et al. | |
| 2004/0248267 | A1* | 12/2004 | Ben-Bassat et al. | 435/156 |
| 2005/0260724 | A1 | 11/2005 | Ben-Bassat et al. | |

FOREIGN PATENT DOCUMENTS

| | | |
|---|---|---|
| JP | 7-017898 | 1/1995 |
| JP | 2004-149438 | 5/2004 |
| JP | 2004-231541 | 8/2004 |
| WO | WO 2005/116229 A2 | 12/2005 |

OTHER PUBLICATIONS

Bandhyopadhyay et al. Solid matrix characterization of immobilized Pseudomonas putida MTCC 1194 used for phenol degradation, Appl Microbiol Biotechnol. Jun. 1999; 51(6): 891-5.*

P.M. Dey, Plant Biochemistry, 1997, Academic Press (Book Not Included).

R. Benrief et. al., Monoterpene Alkaloids, Iridoids and Phenylpropanoid Glycosides From Osmanthus Austrocaledonica, Phytochemistry, 1998, vol. 47:825-832.

R.J. Bandoni et. al. Phenylalanine and Tyrosine Ammonia-Lyase Activity in Some Basidiomycetes, Phytochemistry, 1968, vol. 205-207.

Koichia Ogata et. al., Metabolism of Aromatic Acid in Microorganisms Part 1. Formation of Cinnamic Acid From Phenylalanine, Arg. Biol. Chem., 1967, vol. 31:200-206.

A.V. Emes et. al., Partial Purification and Properties of L-Phenylalanine Ammonia-Lyase From *Streptomyces verticillatues*, Can. J. Microbiology, 1970, vol. 48:613-622.

Kenneth R. Hanson et. al. , The Enzymic Elimination of Ammonia, The Enzymes, 3rd Edition, 1967, pp. 75-167.

Lindhardt et. al. Patents and Literature: Immobilized Biocatalysts, Applied Biochemsitry and Biotechnology, 1987, vol. 14:121-145.

Godwin B. D'Cunha et. al., Stabilization of Phenylalanine Ammonia Lyase Containing *Rhodotorula glutinis* Cells for the Continuous Synthesis PF L-Phenylalanine Methyl Ester/96/, Enzyme and Microbial Technology, 1996, vol. 19:421-427.

Staffan Birnbaum et. al., Covalent Stabilization of Alginate Gel for the Entrapment of Living Whole Cells, Biotechnology Letters, 1981, vol. 3:393-400.

Christopher T. Evans et. al., Bioconversion of Trans-Cinnamic Acid to L-Phenylalanine in an Immobilized Whole Cell Reactor, Biotechnology and Bioengineering, 1987, vol. 30:1067-1072.

Hansruedi Felix, Bioconversions in Permeabilized Cells, Bioprocess. Technol., 1991, vol. 11:259-278.

Hansruedi Felix, Permeabilized Cells, Analytical Biochemistry, 1982, vol. 120:211-234.

Yrr A. Morch et. al., Effect of Ca2+, Ba2+, and Sr2+ on Alginate Microbeads, Biomacromolecules, 2006, vol. 7:1471-1480.

Haroldo Yukio Kawaguti et. al., Production of Isomaltulose Using *Erwinia* Sp. Cells: Culture Medium Optimization and Cell Immobilization in Alginate, Biochemical Engineering Journal, 2006, vol. 29:270-277.

Humberto M.S. Milagre et. al., Asymmetric Bioreduction of Ethyl 3-Halo-2-Oxo-4-Phenylbutanoate by *Saccharomyces cerevisiae* Immobilized in Ca-Alginate Beads with Double Gel Layer, Organic Process Research & Development, 2006, vol. 10:611-617.

M. Kierstan et. al., The Immobilization of Microbial Cells, Subcellular Organelles, and Enzymes in Calcium Alginate Gels, Biotechnology and Bioengineering, 1977, vol. 19:387-397.

Olav Smidsrod et. al., Alginate as Immobilization Matrix for Cells, Trends in Biotechnology, 1990, vol. 8:71-78.

(Continued)

*Primary Examiner* — Robert Mondesi
*Assistant Examiner* — Iqbal H Chowdhury

(57) ABSTRACT

TAL cell biocatalyst was immobilized in alginate cross-linked beads using low concentrations of glutaraldehyde. The biocatalyst beads have highly stable TAL activity and mechanical strength such that they withstand prolonged recycling in production of pHCA.

12 Claims, 10 Drawing Sheets

(56) References Cited

OTHER PUBLICATIONS

Evans, Christopher Thomas et al., Effect of glycerol, polyethylene glycol and glutaraldehyde on stability of phenylalanine ammonia-lyase activity in yeast, Journal of Industrial Microbiology, 1987, p. 53-58, vol. 2, Society for Industrial Microbiology.

Tosa, Tetsuya et al., Immobilization of Enzymes and Microbial Cells Using Carrageenan as Matrix, Biotechnology and Bioengineering, 1979, p. 1697-1709, vol. XXI, John Wiley & Sons, Inc.

Trotman, Robert J., Calcium Alginate Bead Immobilization of Cells Containing Tyrosine Ammonia Lyase Activity for Use in the Production of p-Hydroxycinnamic Acid, Biotechnol, Prog., 2007, p. 638-644, vol. 23, American Chemical Society and American Institute of Chemical Engineers.

International Search Report, International Application No. PCT/US2007/014882, International Filing Date Junl. 26, 2007.

* cited by examiner

IMMOBILIZED TAL BIOCATALYST FOR PRODUCTION OF PARA-HYDROXYCINNAMIC ACID

FIELD OF INVENTION

The present invention relates to the field of molecular biology and biochemistry. More specifically this invention relates to immobilization of biocatalysts expressing enzymes with tyrosine ammonia lyase activity for use in production of para-hydroxycinnamic acid (pHCA).

BACKGROUND OF INVENTION

Para-hydroxycinnamic acid (pHCA) is a high-value, aromatic chemical compound that may be used as a monomer for the production of Liquid Crystal Polymers (LCP). LCPs are used in liquid crystal displays, and in high speed connectors and flexible circuits for electronic, telecommunication, and aerospace applications. Because of their resistance to sterilizing radiation and their high oxygen and water vapor barrier properties, LCPs are used in medical devices, and in chemical and food packaging. Due to its importance as a high value, aromatic chemical compound, pHCA has been chemically synthesized (JP 2004231541; JP 2004149438; U.S. Pat. No. 5,705,618; JP 07017898). However, the chemical synthesis methods are expensive due to the high cost of the starting materials and the extensive product purification required. Moreover, the chemical synthesis methods generate large amounts of unwanted byproducts.

Biological production of pHCA may offer a low cost, simplified synthetic route. In plants, pHCA (also known as p-coumarate) is made as an intermediate for the synthesis of various secondary metabolites such as lignin [Plant Biochemistry, Ed. P. M. Dey, Academic Press, (1997)] and isoflavonoids. Phenylalanine ammonia-lyase (PAL) converts L-phenylalanine to trans-cinnamic acid (CA), which is then converted to pHCA. Methods of pHCA isolation and purification from plants are known [R. Benrief, et al., *Phytochemistry,* 47, 825-832; (1998)], however, these methods are time consuming and cumbersome and do not therefore provide an economical alternative to the current chemical synthesis route. PAL enzymes are also found in fungi (Bandoni et al., *Phytochemistry* 7:205-207 (1968)), yeast (Ogata et al., *Agric. Biol. Chem.* 31:200-206 (1967)), and *Streptomyces* (Emes et al., *Can. J. Microbiology* 48:613-622 (1970)), but not in *Escherichia coli* or mammalian cells (Hanson and Havir In *The Enzymes,* 3$^{rd}$ ed.; Boyer, P., Ed.; Academic: New York, 1967; pp 75-167).

Some PAL enzymes, in addition to their ability to convert phenylalanine to cinnamate, can accept tyrosine as a substrate (PAL/TAL enzymes). The tyrosine ammonia lyase (TAL) activity of these enzymes directly converts tyrosine to pHCA. PAL/TAL enzymes have been introduced into microorganisms for production of pHCA (U.S. Pat. No. 6,368,837, US20040059103 A1). These engineered microorganisms expressing TAL activity can be used in fermentation processes for production of pHCA. Yield and rate of pHCA production is enhanced at high pH, between 8 and 11, so that a two-step fermentation and production process is used for efficient pHCA production (US 20050260724). Extended reuse of the cells containing TAL enzyme, the biocatalyst, in pHCA synthesis would further enhance the economical productivity of the process. However, at the high pH used in the pHCA synthesis reaction, the engineered bacterial biocatalyst cells undergo lysis making reuse of the biocatalyst or catalytic enzyme difficult due to recovery issues.

Biocatalysts have been immobilized to provide a more stable or more easily manipulated enzyme source for enzyme catalyzed processes (Lindhardt, R. J., *Immobilized biocatalysts.* 1987. *Appl. Biochem. Biotechnol.,* 14, 121-145). Biocatalysts with PAL enzyme activity that are used for converting trans-cinnamic acid and ammonia to L-phenylalanine (reverse of the physiological reaction) have been immobilized. The commonly used PAL biocatalysts for phenylalanine production are yeasts such as *Rhodotorula glutinis* (also called *Rhodosporidium toruloides*). *Rhodotorula glutinis* cells with PAL enzyme activity were immobilized and used in production of L-phenylalanine methyl ester (D'Chuna et. al *Enzyme and Microbial Technology* 19:421-427 (1996)). Immobilization was carried out using various agents including immobilization in calcium alginate beads, agarose beads, and PEI-coated calcium alginate beads. In all cases, L-phenylalanine methyl ester production was decreased following immobilization.

U.S. Pat. No. 4,562,151 discloses a process for synthesis of L-phenylalanines using *R. glutinis* cells expressing PAL that are immobilized within glutaraldehyde (GA) cross-linked polyethyleneimine (PEI) coated alginate beads. The beads were prepared according to a method of Birnbaum et al. (*Biotechnology Letters* 3:393-400 (1981)), where PEI is added before GA is added and GA is introduced as a 1% (v/v) solution. In the disclosed synthesis process of U.S. Pat. No. 4,562,151, a polyhydric alcohol or polyethelene glycol-(400) is needed to desensitize the PAL enzyme, enhance the rate of reaction, and inhibit inactivation of the PAL enzyme which otherwise occurs after 12 hours.

L-phenylalanine production by immobilized mutant *Rhodotorula rubra* yeast cells with high PAL activity is described in Evans et. al. (*Biotechnology and Bioengineering,* 30, 1067-1072 (1987)). Cells were immobilized in beads of sodium alginate, polyethylene glycol (PEG), glycerol, glutamate, and sorbitol that were hardened with glutaraldehyde. PEG was needed to stabilize the biocatalyst, along with sorbitol and continuous nitrogen purging to remove oxygen. The reaction rate decreased after the first 10 hours and was further reduced in subsequent runs with reused biocatalyst.

Though enzymes with TAL activity as well as PAL activity are used in biocatalysts for production of pHCA, both the biocatalyst and the reaction have major differences with those used in phenylalanine production. Rather than yeast biocatalysts, bacterial cells engineered for high levels of accumulation of TAL activity are desirable as the biocatalyst. Rather than highly soluble substrates, the tyrosine substrate for TAL-mediated synthesis of pHCA is highly insoluble, and partially crystalline at concentrations used in production reactions. These factors provide additional challenges to preparing an immobilized TAL biocatalyst for use in pHCA production.

Efficient and economical production of pHCA would benefit from the use of immobilized cells having TAL activity that maintain high levels of activity and physical mechanical stability for a prolonged period of time under the high tyrosine solids reaction conditions, allowing use in multiple, extended production runs.

SUMMARY OF THE INVENTION

The invention relates to an improved method of producing pHCA using an immobilized TAL biocatalyst, and to the immobilized TAL biocatalyst. Cells having TAL activity are immobilized by impregnating and cross-linking cell-containing alginate beads with PEI and a low concentration of GA, such that the TAL activity remains high and the beads have sufficient mechanical strength to allow for prolonged use in many production runs.

Accordingly the invention provides an immobilized tyrosine ammonia lyase biocatalyst comprising:

a) a bacterial cell tolerant to pHCA and alkaline pH comprising a tyrosine ammonia lyase enzyme; and b) a cross-linked alginate bead comprising glutaraldehyde in a final concentration of between about $2.5\times10^{-4}$ g and about $6.3\times10^{-3}$ g glutaraldehyde per gram of bead;

wherein the bacterial cell is embedded in the alginate bead.

In another embodiment the invention provides A method of making an immobilized tyrosine ammonia lyase biocatalyst comprising the steps of:

a) providing a bacterial cell tolerant to pHCA and alkaline pH comprising a tyrosine ammonia lyase enzyme;

b) providing a population of alginate beads;

c) embedding the bacterial cell of (a) in the alginate beads of (b);

d) cross-linking the alginate beads of (c) with glutaraldehyde and polyethylenimine wherein the glutaraldehyde is in a final concentration of between about $2.5\times10^{-4}$ and about $6.3\times10^{-3}$ g glutaraldehyde per gram of beads, and wherein glutaraldehyde is added at a rate that is less than about $1\times10^{-4}$ g glutaraldehyde/g beads per minute, and wherein glutaraldehyde and polyethylenimine are added in either order to form an immobilized tyrosine ammonia lyase biocatalyst.

In another embodiment the invention provides a method for producing para-hydroxycinnamic acid comprising:

a) providing an tyrosine ammonia lyase biocatalyst according to claim 1;

b) providing a source of tyrosine;

c) contacting the biocatalyst or (a) with the tyrosine of (b) a suitable aqueous reaction mixture whereby p-hydroxycinnamic acid is produced;

d) recovering the p-hydroxycinnamic acid; and e) optionally repeating c) and d) at least one time.

DESCRIPTION OF THE FIGURES AND SEQUENCE DESCRIPTIONS

The invention can be more fully understood from the following detailed description, the figures, and the accompanying sequence descriptions that form a part of this application.

shows the results of a tBlastN search against translations in all 6 reading frames of the *P. chrysosporium* genomic sequence using the *Trichosporon cutaneum* PAL/TAL amino acid sequence (SEQ ID NO:3) as the query.

Figure 7:
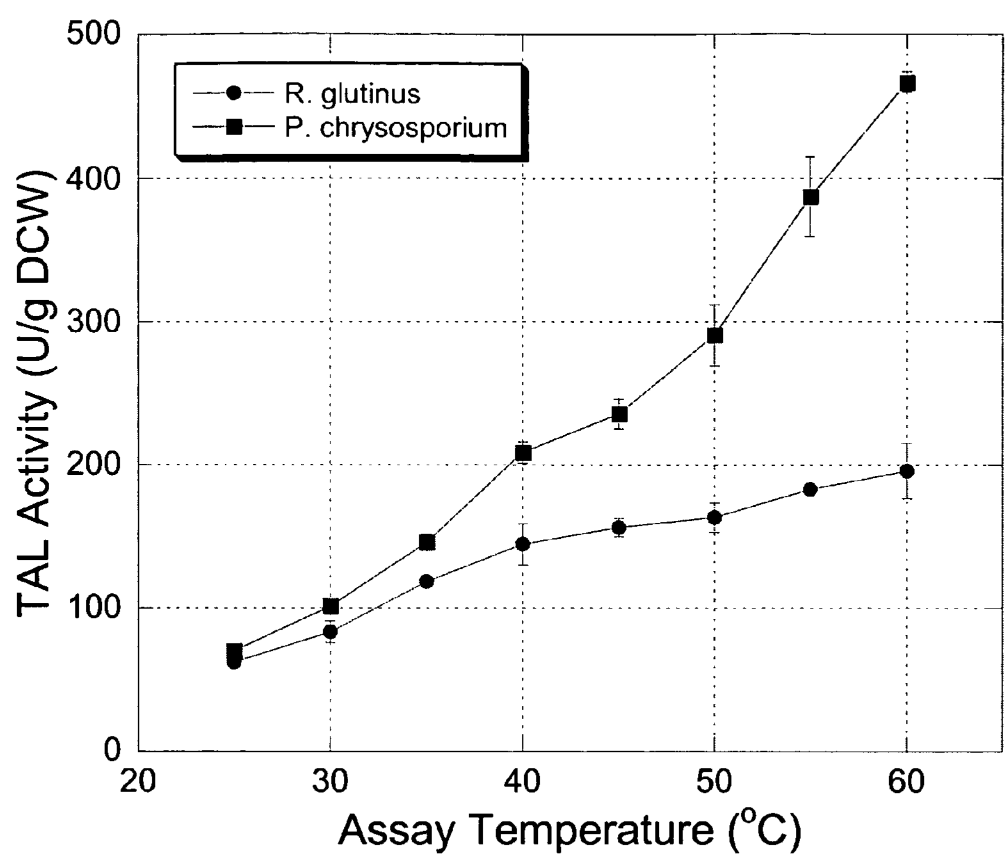

FIG. 7 shows a graph of thermostability of crude extracts of DPD5154 expressing PcTAL versus DPD5124 expressing RgTAL extracts at 60° C. The TAL activity was measured in U/g (soluble proteins).

Figure 8:
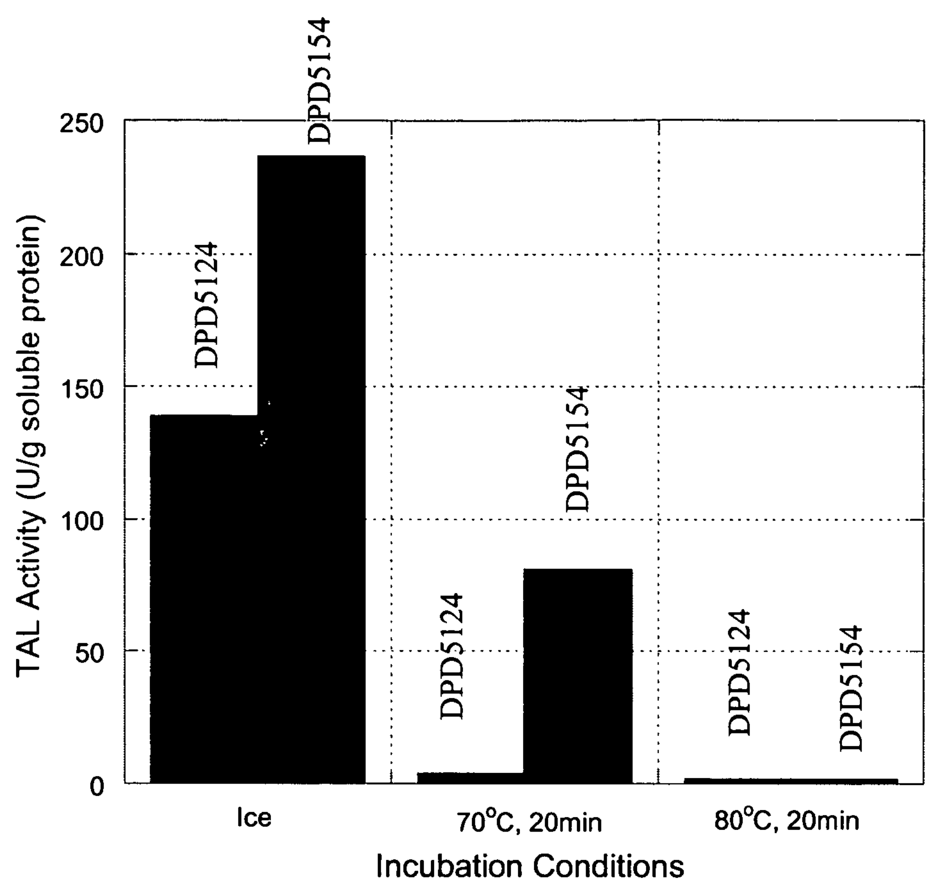

FIG. 8 shows the heat inactivation of TAL activity in crude extracts of DPD5154 strain expressing PcTAL and DPD5124 strain expressing RgTAL. The TAL activity was measured in U/g (soluble proteins).

Figure 9:
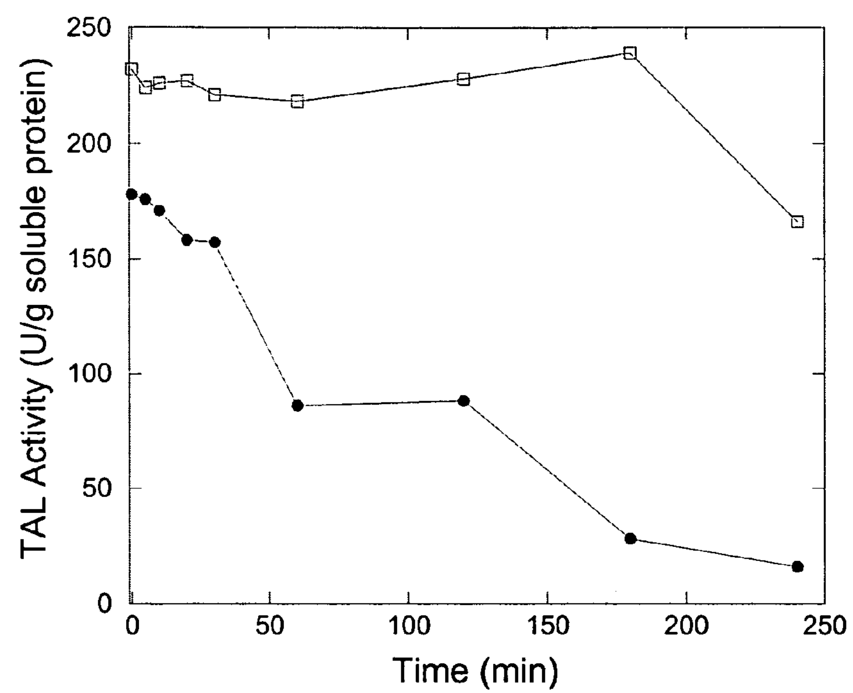

FIG. 9 shows a graph of thermostability of crude extracts of DPD5154 expressing PcTAL versus DPD5124 expressing RgTAL extracts at 60° C. The TAL activity was measured in U/g (soluble proteins).

Figure 10:
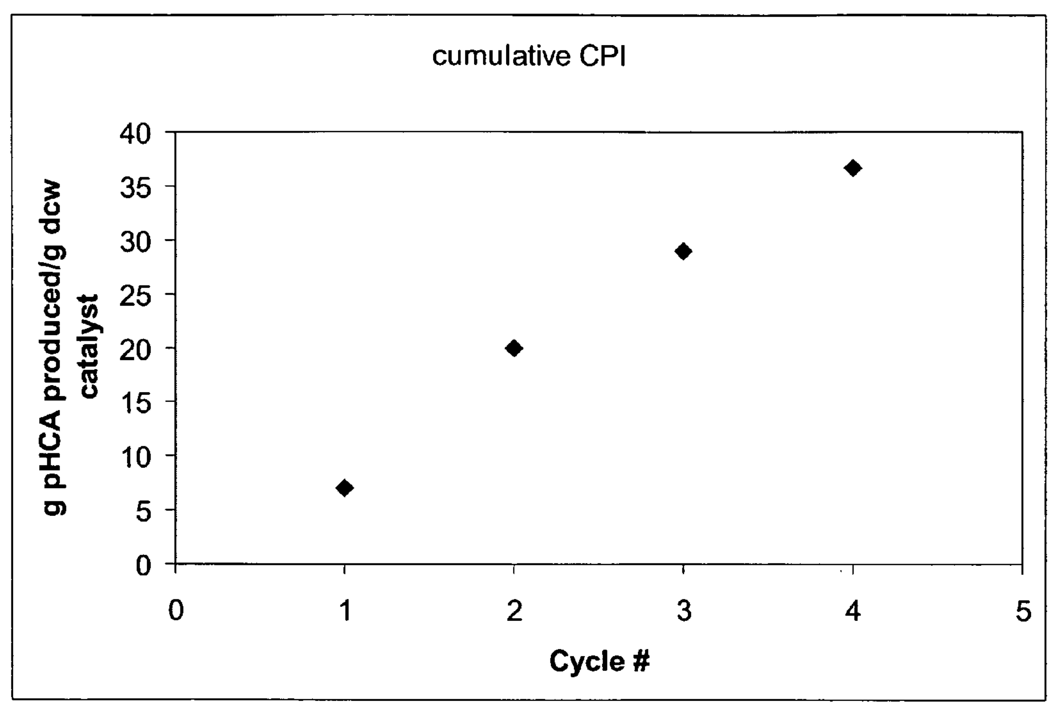

FIG. 10 shows a graph of the cumulative catalyst productivity index (CPI: gram pHCA produced per gram dcw TAL catalyst) in four pHCA production reactions at 45° C. that employed a PcTAL catalyst containing DPD5154 cells immobilized in calcium alginate beads.

The following sequences conform with 37 C.F.R. 1.821-1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

A Sequence Listing is provided herewith on Compact Disk. The contents of the Compact Disk containing the Sequence Listing are hereby incorporated by reference in compliance with 37 CFR 1.52(e). The Compact Disks are submitted in triplicate and are identical to one another. The disks are labeled "Copy 1—Sequence Listing", "Copy 2—Sequence listing", and "CRF—Sequence Listing". The disks contain the following file: CL3466.ST25 having the following size: 93,000 bytes and which were created Jul. 11, 2006.

SEQ ID NO:1 is the amino acid sequence of the *Rhodotorula glutinis* TAL protein.

SEQ ID NO:2 is the amino acid sequence of the *Phanerochaete chrysosporium* TAL protein.

SEQ ID NO:3 is the amino acid sequence of the *Trichosporon cutaneum* PAL/TAL protein.

SEQ ID NO:4 is the amino acid sequence of the *Rhodobacter sphaeroides* PAL/TAL protein.

SEQ ID NO:5 is the amino acid sequence of the *Ustilago maydis* PAL/TAL protein.

SEQ ID NO:6 is the amino acid sequence of the *Petroselinum crispum* PAL/TAL protein.

SEQ ID NO:7 is the amino acid of the mutant *R. glutinis* PAL enzyme having enhanced TAL activity.

SEQ ID NO:8 is the amino acid sequence encoded of the mutant TAL enzyme identified as RM120-1.

SEQ ID NO:9 is the amino acid sequence encoded of the mutant TAL enzyme identified as RM120-2.

SEQ ID NO:10 is the amino acid sequence encoded of the mutant TAL enzyme identified as RM120-4.

SEQ ID NO:11 is the amino acid sequence encoded of the mutant TAL enzyme identified as RM120-7.

SEQ ID NO:12 is the amino acid sequence encoded of the mutant TAL enzyme identified as RM492-1.

SEQ ID NO:13 is the DNA sequence of the coding region for *Rhodotorula glutinis* TAL.

SEQ ID NO:14 is the DNA sequence of the coding region for *Phanerochaete chrysosporium* TAL.

SEQ ID NO:15 is the *E. coli* codon optimized DNA sequence encoding *Phanerochaete chrysosporium* TAL.

SEQ ID NOs:16 and 17 are primers for PCR amplification of the RgTAL coding region from plasmid pKK223-PAL.

SEQ ID NOs:18 and 19 are primers for PCR amplification of the araC-araB region from *E. coli* strain FM5 (ATCC deposit no. 53911) genomic DNA.

SEQ ID NOs:20 and 21 are primers for PCR amplification of the transcription termination sequences rrnBT1 and rrnBT2 from plasmid pTrc99A (Pharmacia Biotech, Amersham, GE Healthcare, Piscataway, N.J.).

SEQ ID NOs:22 and 23 are oligonucleotides of a linker sequence added to pLH312

SEQ ID NOs:24 and 25 are primers for PCR amplification of the colE1 replication origin and rop (encodes a replication origin protein) gene locus of pBR322.

SEQ ID NOs:26 and 27 are primers for PCR amplification of the putative TAL encoding sequence from the cDNA of *P. chrysosporium*.

SEQ ID NO:28 is the amino acid sequence of the mutant *Rhodotorula glutinis* TAL protein encoded by pBAD.PAL3c.

SEQ ID NO:29 is the DNA sequence of the coding region for the mutant *Rhodotorula glutinis* TAL protein in pBAD.PAL3c.

DETAILED DESCRIPTION

The present invention describes an immobilized bacterial TAL biocatalyst and a method for producing pHCA from tyrosine using the immobilized biocatalyst. Conditions were developed for preparing the immobilized TAL biocatalyst, a bacterial cell engineered for high accumulation of TAL activity, that preserve the TAL activity for prolonged time periods and provide sufficient mechanical strength for extended recycling of the biocatalyst in pHCA production runs. pHCA produced by the present method may be used as a monomer for production of Liquid Crystal Polymers (LCP), which may be used in electronic connectors, and telecommunication and aerospace applications. LCP resistance to sterilizing radiation has also enabled these materials to be used in medical devices as well as in chemical, and food packaging applications.

In this disclosure, a number of terms and abbreviations are used. The following definitions are provided.

"Glutaraldehyde" is abbreviated GA.

"Polyethylenimine" is abbreviated PEI

"Polymerase chain reaction" is abbreviated PCR.

"Ampicillin" is abbreviated amp.

"Phenyl ammonia-lyase" is abbreviated PAL.

"Tyrosine ammonia-lyase" is abbreviated TAL.

"para-Hydroxycinnamic acid" is abbreviated pHCA.

As used herein the terms "cinnamic acid" and "cinnamate" are used interchangeably.

The term "invention" or "present invention" as used herein is meant to apply generally to all embodiments of the invention as described in the claims as presented or as later amended and supplemented, or in the specification.

The term "TAL activity" refers to the ability of a protein to catalyze the direct conversion of tyrosine to pHCA. A "TAL enzyme" refers to an enzyme having TAL activity. An enzyme with TAL activity may also have PAL activity.

The term "PAL activity" refers to the ability of a protein to catalyze the conversion of phenylalanine to cinnamic acid. An enzyme with PAL activity may also have TAL activity.

The term "PAL/TAL enzyme" refers to a protein which contains both PAL and TAL activity. Such a protein has at least some specificity for both tyrosine and phenylalanine as an enzymatic substrate.

The term "PAL/TAL activity" refers to ammonia lyase enzymatic activity that is able to use both phenylalanine and tyrosine as substrates.

The term "RgTAL" refers to the *Rhodotorula glutinis* ammonia lyase enzyme that has both PAL and TAL activities. Previously this enzyme has been called *Rhodosporidium toruloides* PAL (U.S. Pat. No. 6,521,748) and *Rhodotorula glutinis* PAL or PAL/TAL. Since TAL activity is the focus in the present method, the enzyme is called RgTAL herein. Some names of genetic constructs containing DNA sequences encoding RgTAL use PAL in the name due to the PAL/TAL activity of the enzyme.

The term "thermostable TAL" refers herein to an enzyme with tyrosine ammonia lyase activity whose activity remains substantially unchanged in a crude extract, at pH8, following one hour incubation at 60° C.

The term "immobilization" refers to any technique to restrict the degrees of freedom of a protein or cell and thus affords some protection from environmental insult (Bickerstaff, Gordon, Editor. *Methods in Biotechnology: Immobilization of Enzymes and Cells*, Humana Press, Totowa, N.J., 1997). Immobilization provides some immediate process benefit such as ease of separation or preserves or prolongs a desired activity.

The term "pHCA and alkaline pH tolerant strain" refers to a strain that undergoes less cell lysis than cells of the MG1655 strain in the presence of about 80 g/L pHCA and a pH of about 10.

The term "gene" refers to a nucleic acid fragment that expresses a specific protein, including regulatory sequences preceding (5' non-coding sequences) and following (3' non-coding sequences) the coding sequence. "Native gene" or "wild type gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes.

The term "gene construct" refers to a nucleic acid fragment that encodes for expression of one or more specific proteins. In the gene construct the gene may be native, chimeric, or foreign in nature.

"Coding sequence" refers to a DNA sequence that codes for a specific amino acid sequence.

The term "expression", as used herein, refers to the transcription and stable accumulation of sense (mRNA) or antisense RNA derived from the nucleic acid fragment of the invention. Expression may also refer to translation of mRNA into a polypeptide.

The term "over-expression" as used herein, refers to the production of a gene product in transgenic organisms that exceeds levels of production in normal or non-transformed organisms.

The term "messenger RNA (mRNA)" as used herein, refers to the RNA that is without introns and that can be translated into protein by the cell.

The term "transformation" as used herein, refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The terms "plasmid", and "vector" as used herein, refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Expression cassette" refers to a chimeric gene having elements in addition to the coding region that allow for expression of that coding region in a host cell. The expression elements are operably linked to the coding region.

The term "host cell" refers to a cell that contains a plasmid or a vector and supports the replication or expression of the plasmid or the vector. Alternatively, foreign DNA may be may be integrated into the genome of a host cell.

"Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites, and stem-loop structures.

"Promoter" or "initiation control region" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments.

The term "regulated promoter" refers to a promoter that is not expressed under normal growth conditions, and is capable of being activated under specified conditions characteristic to the promoter.

The "3' non-coding sequences" or "termination control region" or "terminator" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "codon degeneracy" refers to the nature in the genetic code permitting variation of the nucleotide sequence without effecting the amino acid sequence of an encoded polypeptide. The skilled artisan is well aware of the "codon-bias" exhibited by a specific host cell in usage of nucleotide codons to specify a given amino acid. Therefore, when synthesizing a coding region for improved expression in a host cell, it is desirable to design the sequence such that its frequency of codon usage approaches the frequency of preferred codon usage of the host cell. The resulting sequence is codon-optimized.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: the GCG suite of programs (Wisconsin Package, Genetics Computer Group (GCG), Madison, Wis.), BLASTP, BLASTN, BLASTX (Altschul et al., *J. Mol. Biol.* 215:403-410 (1990)), DNASTAR (DNASTAR, Inc., Madison, Wis.), and the FASTA program incorporating the Smith-Waterman algorithm (W. R. Pearson, *Comput. Methods Genome Res*., [Proc. Int. Symp.] (1994), Meeting Date 1992, 111-20. Editor(s): Suhai, Sandor. Publisher: Plenum, New York, N.Y.). Within the context of this application it will be understood that where sequence analysis software is used for analysis, the results of the analysis will be based on the "default values" of the program referenced, unless otherwise specified. As used herein "default values" will mean any set of values or parameters that originally load with the software when first initialized. More preferred amino acid fragments are those that are at least about 90% identical to the sequences herein using a BLASTP analysis, where about 95% is preferred. Similarly, preferred nucleic acid sequences corresponding to the sequences herein are those encoding active proteins and which are at least 90% identical to the nucleic acid sequences reported herein. More preferred nucleic acid fragments are at least 95% identical to the sequences herein.

Standard recombinant DNA and molecular cloning techniques used here are well known in the art and are described by Sambrook, J., Fritsch, E. F. and Maniatis, T. *Molecular Cloning: A Laboratory Manual,* $2^{nd}$ ed.; Cold Spring Harbor Laboratory: Cold Spring Harbor, N.Y., 1989 (hereinafter "Maniatis"); and by Silhavy, T. J., Bennan, M. L. and Enquist, L. W. *Experiments with Gene Fusions*; Cold Spring Harbor Laboratory: Cold Spring Harbor, N.Y., 1984; and by Ausubel, F. M. et al., In *Current Protocols in Molecular Biology*, published by Greene Publishing and Wiley-Interscience, 1987.

Engineered Bacterial TAL Biocatalyst

In the present method, bacterial strains that are engineered for the ability to express TAL enzyme and accumulate high levels of TAL activity are used in preparing an immobilized TAL biocatalyst for use in pHCA production. In preparing a TAL biocatalyst strain, the bacterial cells are transformed with a chimeric gene to provide expression of TAL enzyme, called a TAL expression gene. The TAL enzyme, which may also have PAL activity, may be from any source. TAL or TAL/PAL enzymes that may be used include, but are not limited to, those from *Rhodotorula glutinis* (SEQ ID NO; 1; U.S. Pat. No. 6,521,748) or a mutant thereof (SEQ ID NO:28), *Phanerochaete chrysosporium* (SEQ ID NO:2; disclosed in co-owned and co-pending U.S. application Ser. No. 11/485,558), *Trichosporon cutaneum* (SEQ ID NO:3; U.S. Pat. No. 6,951,751), *Rhodobacter sphaeroides* (SEQ ID NO:4; US20040059103), *Ustilago maydis* (SEQ ID NO:5; Kim et al. (2001) Curr. Genet. 40:40-48), and parsley (SEQ ID NO:6; (Lois et al. (1989) JOURNAL EMBO J. 8:1641-1648). In addition to natural tyrosine/phenylalanine ammonia lyases, altered enzymes may be used such as a mutagenized *Rhodosporidium toruloides* (*R. glutinis*) enzyme with an increased TAL/PAL activity ratio over that of the wild type enzyme (SEQ ID NO:7; U.S. Pat. No. 6,368,837), and several other mutant enzymes with enhanced TAL activities (SEQ ID NOs:8, 9, 10, 11, 12; U.S. Pat. No. 6,521,748) Several of these enzymes with high TAL activity have been introduced into microorganisms for production of pHCA (U.S. Pat. No. 6,368,837, US20040059103 A1). Preferred in engineered cells for immobilization in the present method are the TAL proteins from *Rhodotorula glutinis* and *Phanerochaete* chrysosporium as set forth in SEQ ID NOs:1, 28 and 2. Particularly suitable is *Phanerochaete chrysosporium* TAL (PcTAL), which is a thermostable enzyme that has increasing activity with increasing temperatures, reaching maximum activity in whole cells at about 60° C., as disclosed in co-owned and co-pending U.S. application Ser. No. 11/485,558, which is herein incorporated by reference.

In the chimeric gene for TAL expression, a DNA sequence encoding a TAL protein is operably linked to regulatory sequences. The DNA sequence encoding the desired TAL protein may be the natural coding sequence, or a synthetic sequence. A synthetic sequence may take advantage of codon degeneracy, such as to provide a codon-optimized coding sequence that is translated into the amino acids of the TAL protein. DNA sequences encoding any of the TAL proteins listed above may be used. Particularly suitable are the natural sequences encoding RgTAL (SEQ ID NO:13) or a mutant RgTAL (SEQ ID NO:29) and PcTAL (SEQ ID NO:14), as well as an *E. coli* codon-optimized sequence encoding PcTAL (SEQ ID NO:15; U.S. application Ser. No. 11/485, 558).

Regulatory sequences include promoters and terminators for transcription, as well as translation control regions. Especially useful are regulatory sequences that direct high level expression of foreign proteins and that allow control of the timing of expression. Particularly useful promoters are regulated promoters that are not expressed under normal growth conditions, and are capable of being activated under specified conditions, such as inducible promoters araB, rhaB, lac, tac, trc, T7, T5, tetracycline promoter, trp promoter, luxR promoter, tightly regulated synthetic promoters derived from lac/tac promoter, Int/att-mediated gene inversion-controlled promoters, acid-inducible promoters, salt inducible promoters, pHCA inducible promoters, and heat/cold inducible promoters. Particularly suitable is the araB promoter as disclosed in co-owned and co-pending U.S. application 11/485,577, which is herein incorporated by reference. Arabinose induction is particularly effective in a host cell having a deletion of the araBAD operon in the chromosome. The araBAD operon may be deleted by methods well known in the art, such methods include one-step inactivation of chromosomal genes in *E. coli* K12 strains using PCR products with homologous sequences as the chromosomal DNA region adjacent to the knockout target (e.g. araBAD) [Datsenko K A et al., *Proc Natl Acad Sci USA* 97: 6640-6645 (2000)].

Termination control regions may also be derived from various bacterial genes, as is know by one skilled in the art.

A chimeric gene for expression of a thermostable TAL enzyme is generally added to a vector that is used to make a recombinant host cell suitable for use in the present method. Vectors useful for the transformation of suitable host cells are well known by one skilled in the art. Typically the vector additionally contains sequences allowing autonomous replication or chromosomal integration and a marker. Autonomous replicating vectors are typically plasmids used in cloning and transformation procedures, which then are maintained within a recombinant cell. Vectors may also be used which promote the integration of the chimeric gene encoding a thermostable TAL into the host cell genome. Such vectors may be for either random or site-directed integration, or for homologous recombination. A vector may have features allowing single cross-over or double-crossover types of homologous recombination. Transformation of the vector into a host cell is by methods well know in the art such as uptake in calcium treated cells, electroporation, freeze-thaw uptake, heat shock, lipofection, electroporation, conjugation, fusion of protoplasts, and biolistic delivery.

The marker provides a trait for identifying cells by methods including selection and screening. The marker is used to identify those cells that receive the transforming plasmid. Types of usable markers include screening and selection markers. Many different selection markers available for recombinant cell selection may be used, including nutritional markers, antibiotic resistance markers, metabolic markers, and heavy metal tolerance markers. Some specific examples include, but are not limited to, thyA, serA, ampicillin resistance, kanamycin resistance, carbenicillin resistance, and mercury tolerance. In addition, a screenable marker may be used to identify recombinant cells. Examples of screenable markers include GFP, GUS, carotenoid production genes, and beta-galactosidase. Typically, a selectable marker is used.

TAL Biocatalyst Host Strain

TAL biocatalyst host strains used in the present method are bacterial strains that have tolerance to high levels of pHCA and alkaline pH. These are conditions experienced during the tyrosine to pHCA production reaction. Tolerance is exhibited by reduced cell lysis under these conditions, as compared to the MG1655 strain of *E. coli* K12, a strain well known to one skilled in the art. Strains that are pHCA and alkaline pH tolerant include, but are not limited to, *E. coli* K12 strains RFM443 (Drolet et al. (1995) Proc. Natl. Acad. Sci. USA. 92:3526-3530), W3110 (ATCC #27325), and BW25113 (CGSC#7636 from the *E. coli* Stock Center at Yale University, New Haven, Conn.).

Additional bacterial strains with tolerance to high pHCA concentration and alkaline pH may be readily identified by one skilled in the art using a screen. Cells may be incubated in the presence of a high concentration of pHCA at a high pH, and the amount of cell lysis that occurs is observed and compared to cell lysis in strain MG1655 (ATCC #700926). Cell lysis may be assayed by the presence in culture media of an internal cellular protein, for example by gel electrophoresis and protein staining, immunoassays, or other protein assays. pHCA at concentrations that are between about 40 g/L and 100 g/L, and a pH between about 8 and 10 may be used in screening. Particularly useful are bacterial strains that show reduced lysis as compared to MG1655 cells when incubated in the presence of 80 g/L pHCA at pH 10 for four hours. These strains are preferred for use in preparing TAL biocatalysts. In addition to screening bacterial strains, cells may be engineered, or mutagenized and selected for pHCA and high pH tolerance. Screening may be done either prior to or after the test strains are engineered for TAL expression as described above.

In addition to screening bacterial strains for tolerance to high levels of pHCA and alkaline pH, cells may be engineered, or mutagenized and selected for pHCA and high pH tolerance to develop a host strain for use in the present method. Methods for mutagenesis and selection are well known to one skilled in the art, such as by chemical mutagenesis and transposon insertion. In the latter method, genes may be identified that are involved in providing pHCA and alkaline pH tolerance, which may be genes targeted in engineering of these properties in other strains.

Biocatalyst Cell Growth

Bacterial cells engineered for production of high levels of TAL enzyme activity, that are pHCA and high pH tolerant, may be grown in fermentation processes that are known to one skilled in the art. Typically the cells are grown without TAL expression, then the regulated promoter controlling TAL expression is activated such that the TAL enzyme is expressed and accumulates in the cells.

The cells are grown in the presence of a fermentable carbon substrate. Fermentable carbon substrates may include but are not limited to monosaccharides such as glucose, raffinose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally the carbon substrate may also be organic acids such as acetate, pyruvate and glycerol as well as one-carbon substrates such as carbon dioxide, formaldehyde, formate or methanol.

A large scale fermentation process used for growing the bacterial cells may be a batch culture or a continuous culture. A classical batch fermentation is a closed system where the composition of the medium is set at the beginning of the fermentation and not subject to alterations during the fermentation. Thus, at the beginning of the fermentation the medium is inoculated with the desired microorganism(s) and fermentation is permitted to occur adding nothing to the system. Typically, however, the concentration of the carbon source in a “batch” fermentation is limited and attempts are often made at controlling factors such as pH and oxygen concentration. In batch systems the metabolite and biomass compositions of the system change constantly up to the time the fermentation is stopped. Within batch cultures cells moderate through a static lag phase to a high growth log phase and finally to a stationary phase where growth rate is diminished or halted. If untreated, cells in the stationary phase will eventually die.

A variation on the standard batch system is the Fed-Batch system, which may also be used. Fed-Batch fermentation processes comprise a typical batch system with the exception that the fermentable carbon substrate is added continuously or in increments as the fermentation progresses. Fed-Batch systems are useful when catabolite repression is apt to inhibit metabolism of the cells, where it is desirable to have limited amounts of substrate in the medium, or when growth to high densities is desirable. Measurement of the actual substrate concentration in Fed-Batch systems is difficult and therefore the rate of substrate consumption is estimated on the basis of the changes of measurable factors such as pH, dissolved oxygen and the partial pressure of waste gases such as CO2. Batch and Fed-Batch fermentations are common and well known in the art and examples may be found in [Brock, T. D.; *Biotechnology: A Textbook of Industrial Microbiology,* 2nd ed.; Sinauer Associates: Sunderland, Mass., 1989] or [Deshpande, M. V. *Appl. Biochem. Biotechnol.* 36:227, (1992)], herein incorporated by reference.

In addition, continuous fermentation may be used. Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in their log phase of growth. Continuous fermentation allows for modulation of any number of factors that affect cell growth or end product concentration. For example, one method will maintain a limiting nutrient such as the carbon source or nitrogen level at a limiting concentration and allow all other parameters to be in excess. In other systems a number of factors affecting growth can be altered continuously while the cell concentration, measured by the medium turbidity, is kept constant. Continuous systems strive to maintain steady state growth conditions and thus the cell loss due to the medium removal must be balanced against the cell growth rate in the fermentation. Methods of modulating nutrients and growth factors for continuous fermentation processes as well as techniques for maximizing the rate of product formation are well known in the art of industrial microbiology and a variety of methods are described by Brock, supra.

Expression of the TAL gene in the bacterial cells is activated following a period of cell growth, typically when further growth is not required. At this stage, conditions for expression of the TAL enzyme are applied to the culture. The conditions typically include adding an inducer that activates the regulated promoter that is operably linked to the coding region for the TAL so that the enzyme is produced. For example, when the coding region for TAL is linked to the araB promoter, cells are first grown without the arabinose inducer such that the promoter is not activated (in an araBAD host). Arabinose is added to activate the promoter for TAL enzyme production. TAL then accumulates in the cells.

Preparation of Immobilized TAL Biocatalyst

A process was developed for immobilizing bacterial cells with TAL activity that prolongs the TAL activity without the need for desensitizing agents that were required to prolong activity in immobilized PAL biocatalysts used for phenylalanine production. In preparing a biocatalyst with PAL activity for phenylalanine production, desensitizing of PAL activity was achieved by including polyhydric alcohols or polyethylene glycol in immobilized yeast cell preparations, as well as by purging with nitrogen to remove oxygen during catalysis (U.S. Pat. No. 4,562,151; Evans, supra). Surprisingly, applicants found that these agents and treatment are not required for maintaining high TAL activity in bacterial TAL cell biocatalysts when immobilized as described herein.

In addition, applicants found that TAL activity is very sensitive to GA such that enzyme activity is lost when bacterial cells with TAL activity are cross-linked with GA, or are embedded in alginate beads and cross-linked with the high GA concentration previously used in preparing immobilized PAL yeast cells (Birnbaum, supra). Active TAL biocatalyst could be prepared only by using much lower GA concentrations, that are between about 0.125% and about 3.15% of the standard conditions described by Birnbaum et. al., supra. Applicants surprisingly found that TAL biocatalyst immobilized using these low concentrations of GA showed prolonged high mechanical stability under the high solids, high pH reaction conditions used in tyrosine conversion to pHCA.

In the present immobilization process, bacterial TAL cells grown and induced for TAL expression as described above are harvested, typically by centrifugation, and used immediately or stored as a frozen paste at about −20° C. to −80° C. until use. In addition, cells may be stored for limited time periods of about 10 days at room temperature or about a month at 4° C. Thus either whole cells or cells potentially permeabilized by a freeze-thaw cycle may be used. The cells may as well become permeabilized during the alkaline pH conditions of the typical pHCA production run, or may be permeabilized by other methods which are well-known to those skilled in the art, including but not limited to, treatment with organic solvents or detergents (Felix, *Bioprocess. Technol.* 11:259-278 (1991); Felix, *Anal. Biochem.* 120:211-234 (1982)).

In preparing beads with immobilized TAL cells for use as a biocatalyst in the present method, first a suspension is made by dispersing the TAL cells in an alginate solution. The alginate may be any soluble form of alginate such as sodium alginate or alginic acid. Sodium alginate is particularly useful. Any strong divalent cation may be used in forming beads of alginate with embedded TAL cells. Examples include strontium, barium, and calcium. Particularly suitable is calcium, which may be provided by any soluble calcium salt such as calcium chloride, calcium nitrate, or calcium acetate. Particularly suitable is a calcium acetate solution. The beads of calcium alginate with embedded TAL cells may be formed by a particle preparation method, as generally described in Morch et. al. *Biomacromolecules* (2006) 7:1471; Kawaguti et. al., Biochemical Engineering Journal (2006) 29:270; Milagre et. al. *Organic Process Research & Development* (2006) 10:611; or Kierstan and Buck, *Biotechnology and Bioengineering* (1977) 19:387. Typically, alginate beads with embedded TAL cells are formed by dripping the alginate/cell suspension into a calcium acetate solution with stirring. Cell and alginate concentrations may vary for making beads. The alginate solution may be about 2% to about 4% alginate as described in Smidsrod and Skjakl-braek, *Trends in Biotechnology* (1990) 8:71. Particularly useful is an alginate solution that is about 2.25% to about 2.75% alginate. The amount of cells in the alginate beads may be up to about 12.5% dry cell weight. Particularly useful is 10% dry cell weight of TAL cells embedded within high gel strength alginate beads of about 2.75 wt % alginate formed using calcium.

The alginate beads with embedded TAL cells are further stabilized by chemical cross-linking. An electrophilic bis-functional cross-linking agent and a polymeric amine are used as chemical cross-linkers. Particularly suitable are glutaraldehyde (GA) and polyethyleneimine (PEI), either of which may be added first. However, GA followed by PEI is the preferred order as the beads made by first cross-linking with GA appeared more uniform during subsequent use in pHCA production. The low GA concentrations described above that are used to prepare an immobilized active TAL biocatalyst range between about $2.5\times10^{-4}$ and $6.3\times10^{-3}$ gram of GA per gram of alginate/TAL cell beads. Particularly useful is about $3\times10^{-3}$ gram of GA per gram of beads. The GA is added slowly over time to reduce exposure of the cells to GA. GA is added at a rate that does not exceed about $1\times10^{-4}$ g GA/g bead per minute. Typically, a 25% w/w GA solution is added dropwise to the beads that are in a calcium acetate solution. The time for GA cross-linking to prepare the immobilized TAL biocatalyst is typically from 5 minutes to 2 hours, preferably 30 minutes to 1 hour.

PEI is typically used in an amount that is 1× to 4× the amount of GA. Thus about $2.5\times10^{-4}$ to $25\times10^{-3}$ gram of PEI per gram of alginate/TAL cell beads may be used. Particularly useful is about $6.3\times10^{-3}$ gram of PEI per gram of alginate/TAL cell beads. The time for PEI cross-linking to prepare the immobilized TAL biocatalyst is typically from 30 minutes to 24 hours, preferably 1 hour to 18 hours.

pHCA Reaction Using Immobilized Biocatalyst pHCA is produced in the present method by contacting the TAL biocatalyst, immobilized using the method described above, with tyrosine under controlled conditions of pH and temperature for a period of time to allow conversion of tyrosine to pHCA by the enzyme. Tyrosine used in the present method may be made by a microorganism (further described below), synthesized through a chemical reaction, or made by other methods such as purifying from a natural source, an example of which is chicken feathers. Commercially available tyrosine, such as from J. T. Baker (Phillipsburg, N.J.), may be used. Tyrosine may be used as partially or fully purified tyrosine for addition to the thermostable TAL for a pHCA production run. Tyrosine is relatively insoluble in aqueous solution. Tyrosine may be added to the pHCA reaction in a low concentration where it is in solution, such as about 12 mM, or at higher concentrations where the tyrosine is partially in crystalline form, up to about 300 mM. Typically tyrosine is added as a slurry to produce a final concentration of about 275 mM which creates a viscous reaction mixture containing mostly tyrosine crystals and about 10-15 mM tyrosine in the liquid phase.

The optimal pH for TAL activity is about 8.0 to about 11.0, where a pH of about 9.5 to about 9.9 is preferred for use in the pHCA production reaction. Particularly useful is a pH of about 9.8, which supports efficient TAL activity and provides for enhanced stability of the immobilized biocatalyst. The temperature of the reaction is appropriate for the specific TAL enzyme used. For example, production using the RgTAL enzyme is typically run at about 30° C. to 35° C. The PcTAL is a thermostable enzyme and allows production of pHCA at elevated temperature as described in co-owned and co-pending U.S. application Ser. No. 11/485,558. With immobilized PcTAL biocatalyst, temperatures of about 35° C. to about 60° C. where temperatures that are at least 35° C. and up to about 55° C., are particularly suitable and where temperatures of between about 40° C. and about 50° C. are most suitable.

In the present method, the immobilized TAL biocatalyst is contacted with tyrosine in a suitable aqueous reaction mixture under the described conditions of temperature and pH which are maintained for a period of time during which pHCA is produced. The reaction mixture includes ions corresponding to those ions used in forming the alginate beads. For example, for alginate beads made with calcium, the reaction mixture includes calcium at a concentration between about 5 mM and about 20 mM to maintain bead integrity. The pH of the solution is adjusted to the desired alkalinity using a base such as potassium hydroxide, ammonium hydroxide, or sodium hydroxide. Sodium hydroxide is typically used.

Typically, the reaction is in a calcium ion solution that is agitated for about one hour to about 24 hours. The run is then terminated and the reaction solution is removed from the immobilized biocatalyst, which is optionally washed with calcium chloride solution. The pH and temperature controls are reactivated and tyrosine is added to the immobilized TAL biocatalyst for a second pHCA production run. The process for preparing the immobilized TAL biocatalyst described herein allows extensive reuse of this biocatalyst in multiple, extended pHCA production runs. TAL enzyme activity and bead catalyst physical integrity are maintained for up to at least about 41 pHCA production runs. Thus immobilization of the TAL biocatalyst allows extending the operational life of the catalyst for economical pHCA production.

Immobilized TAL biocatalyst may also be used in a continuous process for production of pHCA in which pHCA is removed from the process and additional tyrosine substrate is added. Any continuous process design may be used, an example of which is a fluidized bed reactor designed to accommodate a continuous pHCA production process with the addition of new solution with tyrosine and the removal of pHCA product solution.

Recombinant Cells Producing Tyrosine

As stated above, tyrosine used in the present method may be produced by a microorganism. The tyrosine may be recovered as partially or fully purified tyrosine prior to contacting the TAL biocatalyst. Strains of microbial cells, such as *Escherichia, Methylosinus, Methylomonas, Pseudomonas, Streptomyces, Corynebacterium, Brevibacteria, Microbacterium, Arthrobacter, Candida, Citrobacter*, and *Rhodobacter*, which are known to over-produce tyrosine, or may be genetically engineered to over-produce tyrosine, are suitable as a source of tyrosine. Examples of tyrosine over-producing strains that are suitable for the present method include, *Microbacterium ammoniaphilum* ATCC 10155, *Corynebactrium lillium* NRRL-B-2243, *Brevibacterium divaricatum* NRRL-B-2311, *Arthrobacter citreus* ATCC 11624, and *Methylomo-*

*nas* SD-20. Other suitable tyrosine over-producers are known in the art, see for example *Microbial production of L-tyrosine: A Review*, T. K. Maiti et al, Hindustan Antibiotic Bulletin, vol 37, 51-65, 1995. Additionally an example of an *Escherichia* tyrosine over-producing strain that may be used is *E. coli* TY1, available from OmniGene Bioproducts, Inc. Cambridge, Mass. New strains that over-produce tyrosine may be identified, produced through mutation or genetic engineering, or otherwise obtained. Any strain that overproduces tyrosine may be used in the present method.

Microbial cells that over-produce tyrosine may be grown in fermentation as described above for growth of TAL cells. Tyrosine may be recovered from fermentation broth using low speed centrifugation. The resulting pelleted material may be suspended in water and separated again using low speed centrifugation.

Recovery of pHCA

Methods for the recovery of pHCA from a growth medium are available. One preferred method is taught in the co-pending and commonly owned U.S. patent application Ser. No. 10/824,237, hereby incorporated by reference. Briefly the method involves first acidifying the fermentation broth containing either the pHCA to a pH or about 4.0 or below and then adding an extractant. Extractants useful for this purpose are water immiscible organic solvents and may include but are not limited to, diisopentyl ether, n-propyl benzoate, 2-undecanone, dibenzyl ether, 2-tridecanone, 2-decanone, 1-pentanone 1-phenyl, methyl decanoate, 1-undecanol, diisobutyl DBE-IB and mixtures thereof. The pHCA or CA is dissolved in the extractant and removed from the medium. The pHCA or CA may then be recovered from the extractant by well known means such as distillation, adsorption by resins, or separation by molecular sieves. Alternatively, the pHCA may be recovered by acidification of the growth medium to a pH below 2.0, followed by crystallization.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used here are well known in the art and are described by Sambrook, J., Fritsch, E. F. and Maniatis, T. *Molecular Cloning: A Laboratory Manual,* $2^{nd}$ ed.; Cold Spring Harbor Laboratory: Cold Spring Harbor, N.Y., 1989 (hereinafter "Maniatis"); and by Silhavy, T. J., Bennan, M. L. and Enquist, L. W. *Experiments with Gene Fusions*; Cold Spring Harbor Laboratory: Cold Spring Harbor, N.Y., 1984; and by Ausubel, F. M. et al., In *Current Protocols in Molecular Biology*, published by Greene Publishing and Wiley-Interscience, 1987.

The meaning of abbreviations is as follows: "s" means second(s), "min" means minute(s), "h" means hour(s), "psi" means pounds per square inch, "nm" means nanometers, "d" means day(s), "μL" means microliter(s), "mL" means milliliter(s), "L" means liter(s), "mm" means millimeter(s), "nm" means nanometers, "mM" means millimolar, "M" means molar, "mmol" means millimole(s), "μmole" means micromole(s)", "g" means gram(s), "μg" means microgram(s) and "ng" means nanogram(s), "U" means units, "mU" means milliunits and "U/g" means units per g, "OD" means optical density, "$OD_{600}$" means the optical density measured at a wavelength of 600 nm, "ppm" means parts per million, "kD" means kilodaltons, "rpm" means revolutions per minute, dcw" means dry cell weight, "dO" means dissolved oxygen. "SLPM" stands for standard liters per minute, "CA" is cinnamic acid, "GA" is glutaraldehyde, "PEI" is polyethyleneimine, "CAPS" is N-Cyclohexyl-3-aminopropanesulfonic acid.

Molecular Biology Techniques:

Restriction enzyme digestions, ligations, transformations, and methods for agarose gel electrophoresis were performed as described in Maniatis.supra. Polymerase Chain Reactions (PCR) techniques are described in White, B., *PCR Protocols: Current Methods and Applications*, Volume 15 (1993) Humana Press Inc, Totowa, N.J.

Deletion of the araBAD Operon

A two step transduction method was used to bring a deletion of the araBAD operon into several strains. In the first step, a leu::Tn10 marker, which is near the araBAD operon, was moved by P1clr100Cm mediated generalized transduction into several *E. coli* K12 strains. The donor strain was RFM793 [leu::Tn10 imp4213 rpsL galK2 Δ (lac74); available from Dupont Company, Wilmington, Del.]. The recipients were MG1655 [F-LAM-rph-1; ATCC#700926], RFM443 [rpsL galK2 Δ (lac74); Drolet et al. (1995) Proc. Natl. Acad. Sci. USA. 92:3526-3530], W3110 [F—rph-1, IN(rrnD-rrnE) 1; ATCC#27325], and pBAD.PAL3c/FM5 [pBAD.PAL3c/F-, lambda-, rph-1, tnaB::tetR insert c1857, phage resistant, rpoS396(Am); FM5 is ATCC#53911]. Following selection for resistance to 15 μg/ml tetracycline, transductants were purified at 42° C. then tested for leucine auxotrophy, sensitivity to chloramphenicol (test for P1 lysogen), and ability to grow on MacConkey agar (test for Imp+). Transductants with the desired phenotype were then used as recipients in the second P1clr100Cm-mediated transduction step for which the donor was BW25113 [Lambda-rph-1 lacIq rrnBT14 Δ (lacZ)WJ16 hsdR514 Δ (araBAD)AH33 Δ (rhaBAD)LD78; CGSC#7636 from the *E. coli* Stock Center at Yale University (New Haven, Conn.)] and selection was for protrophic growth on M9 glucose plates (Teknova). Transductant colonies were purified on M9 glucose minimal medium plates at 42° C. and tested for tetracycline sensitivity (all were tetracycline sensitive, as expected for Leu+ transductants) and the inability to metabolize arabinose (94% were Ara−, as expected for closely linked genes). Ara− transductants of each of the recipients were further verified to be CmS, and hence not lysogenic for phage P1.

HPLC Method

Analysis of mixtures of pHCA and tyrosine were performed by HPLC using an Agilent 1100 System (Agilent technologies, Palo Alto, Calif.) with a photodiode array detector and a Zorbax SB-C18 column (3.5 μm, 4.6×150 mm—rapid resolution) where separation is achieved by a gradient combining two solvents: Solvent A, 0.1% trifluoroacetic acid in water; Solvent B, 0.1% trifluoroacetic acid in acetonitrile. Conditions include a column flow rate of 1.0 mL/min, with a run time of 15 minutes and a post-run time of 5 minutes. The solvent gradient used is that given in Table 1 below. The pump ran within pressure limits defined as a minimum of 20 bar and a maximum of 400 bar. Solutions were filtered through a 0.45-micron nylon filtered before dilution in HPLC-grade water and transfer into HPLC vial and injection. The sample spectrum was scanned from 100 nm to 380 nm, with the signal for tyrosine being recorded at 278 nm and a retention time of 3.5±0.1 minutes. PHCA was detected at 312 nm, with a typical retention time of 5.3±0.1 min.

TABLE 1

| Solvent Gradient Used for HPLC | | |
|---|---|---|
| Time (min) | Solvent A | Solvent B |
| 0 | 95% | 5% |
| 8 | 20% | 80% |
| 10 | 20% | 80% |
| 15 | 95% | 5% |

TAL Whole Cell Spectrophotometric Cuvette Assay

The TAL assay measures formation of the product, para-hydroxycinnamic acid (pHCA), formed by the TAL or PAL/TAL enzyme when tyrosine is used as substrate. The extinction coefficient of pHCA at 315 nm is 16,800. The TAL enzyme suspension was prepared by placing a "chip" (200-500 mg) of frozen cell paste in a 50 ml disposable centrifuge tube. A volume of re-suspension buffer (10 mM Tris-HCl adjusted to pH 8.0) equal to 5× the weight of the cell paste was added to the chip and the tube was placed on wet ice and agitated gently to thaw the cells. The re-suspended cells were centrifuged (~6,000×g for 6 minutes) and the supernatant was discarded. The cell pellet was re-suspended in 1 ml of re-suspension buffer, transferred to a 1.5 ml eppendorf tube, and centrifuged (~14,000×g for 6 minutes). The supernatant was discarded and the steps of resuspending the pellet in buffer and centrifugation were repeated three (3) times so that the pellet was washed a total of four (4) times. After the final wash, the pellet was re-suspended in 1 ml of re-suspension buffer and the sample tube was stored on ice. The optical density was measured at 600 nm and the typical OD of the cell re-suspension was approximately 150 to 200. The cell suspension was diluted to 3.0±0.5 OD using the Tris re-suspension buffer. The assay buffer of 100 mM N-Cyclohexyl-3-aminopropanesulfonic acid (CAPS) was adjusted to pH 10.0 at room temperature (circa 22±3° C.) and was warmed to 35° C. for use in the assay. The substrate solution was 100 mM tyrosine in 200 mM NaOH (stored at −20° C. and warmed to 35° C. for use). All of the equipment (UV/VIS spectrophotometer cell holders, disposable methyl acrylate semi-micro cuvettes (VWR Cat. #58017-850), assay buffer, and the tyrosine solution) were stabilized at 35° C. prior to use because the assay is temperature sensitive. These reagents were added to the cuvette: 890 μL assay buffer, 100 μL tyrosine substrate solution. The two components were mixed prior to adding the 3 OD cell suspension (10 μL). Immediately after adding the TAL cell suspension, the contents were mixed, the spectrophotometer absorbance was zeroed and the absorbance was monitored at 315 nm for one to two minutes. The slope was observed for one to two minutes.

Using the above whole cell preparation and assay protocol a typical sample assayed in triplicate produces a standard deviation of approximately 10%. Due to temperature sensitivity and variations in individual manipulations, variabilities of approximately 15% have been observed for the reported activities (U/gr dcw).

TAL activity may be calculated as follows:

Total TAL activity (μM/min)=Δ315 nm/min×1,000,000 (μM/M) divided by pHCA extinction coefficient ($M^{-1}$ $cm^{-1}$)=Δ315 nm/min×1,000,000 (μmol/mol) divided by 16,800 ($M^{-1}$ $cm^{-1}$).

TAL specific activity (U/g)=total TAL activity (μM/min) divided by the amount of protein used in the assay.

Example 1

Construction of Arabinose Inducible Expression Vectors for RgTAL Enzyme (Strains DPD4574 & DPD5124)

The purpose of this example was to clone the gene encoding the PAL/TAL enzyme from *R. glutinis* into a medium copy expression vector for the high level inducible expression of *R. glutinis* PAL/TAL (abbreviated herein as RgTAL).

Figure 1:
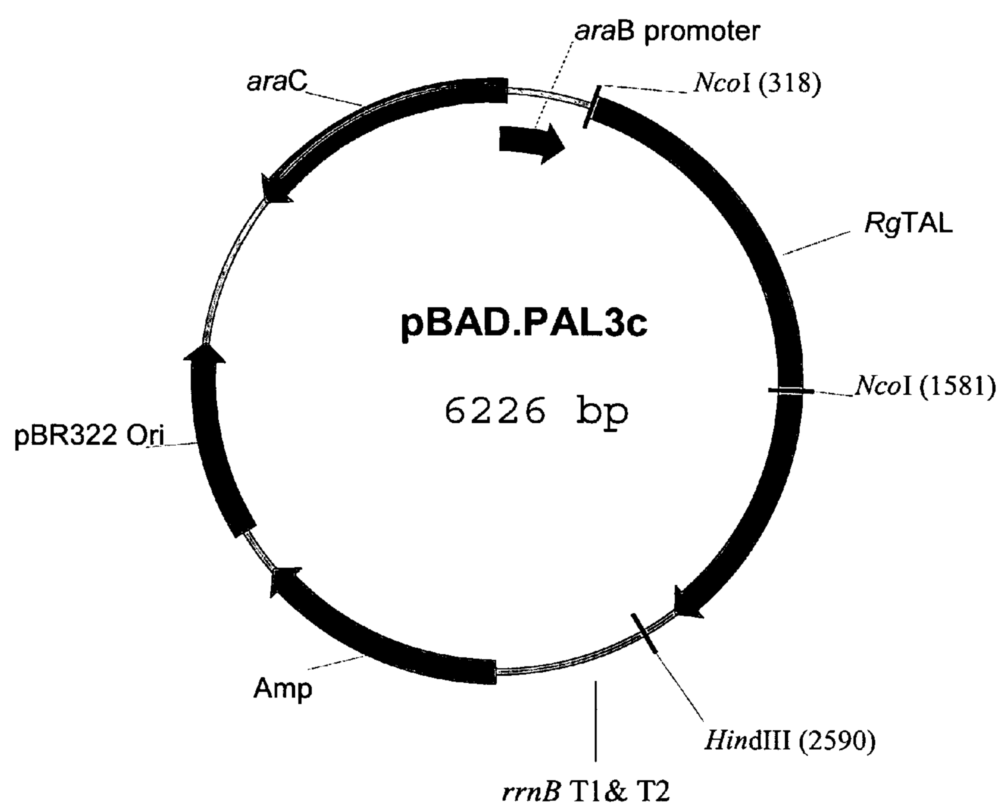
FIG. 1 shows a plasmid map of pBAD.PAL3c.

A RgTAL expression vector, pBAD.PAL3c, was constructed by subcloning the RgTAL coding region (SEQ ID NO:13) from pKK223-PAL, that is described in U.S. Pat. No. 6,521,748, which is herein incorporated by reference. The RgTAL coding region was PCR amplified from plasmid pKK223-PAL by primers of SEQ ID NOs:16 and 17. An NcoI site was introduced at the ATG start codon in the resulting PCR fragment, which was digested with NcoI (partial digestion) and HindIII, and ligated into the NcoI and HindIII sites in pBAD.HisB (Invitrogen), which are in a Multiple Cloning Site between an araB promoter and rrnB T1 and T2 terminators to generate plasmid pBAD.PAL3c (FIG. 1). pBAD.PAL3c allows direct expression of the RgTAL coding region from the *Salmonella typhimurium* araB promoter in pBAD.HisB. The pBAD.HisB vector also contains the *S. typhimurium* araC gene which encodes the transcriptional activator for the araB promoter, and ampicillin resistance marker, and the pBR322 origin of replication. *E. coli* K12 strain BW25113 was transformed with pBAD.PAL3c and the resulting strain was named DPD4574. A derivative of BW25113 that contained a plasmid was obtained from Professor Barry Warnner at Purdue University. The plasmid, which was temperature sensitive, was cured from the cells by growing at high temperature to provide the BW25113 strain. BW25113 is available as CGSC#7636 from the *E. coli* Stock Center at Yale University (New Haven, Conn.). Upon sequencing of the RgTAL coding region in pBAD.PAL3c (SEQ ID NO:29) it was found that a mutation had occurred during cloning such that the encoded amino acid at position 24 had asp in place of asn (SEQ ID NO:28). In addition, pBAD.PAL3c was transformed into the *E. coli* B strain BL21AI that has a deletion of the araBAD operon (Invitrogen) to make the RgTAL expressing strain DPD5056.

Figure 2:
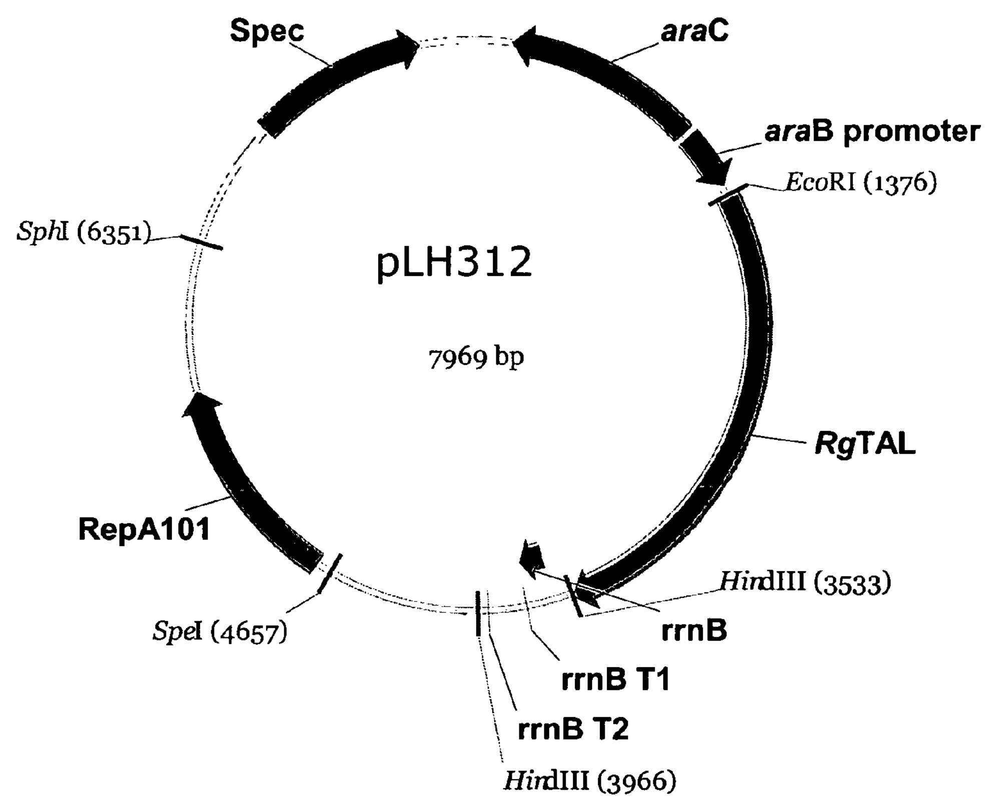
FIG. 2 shows a plasmid map of pLH312.
Figure 3:
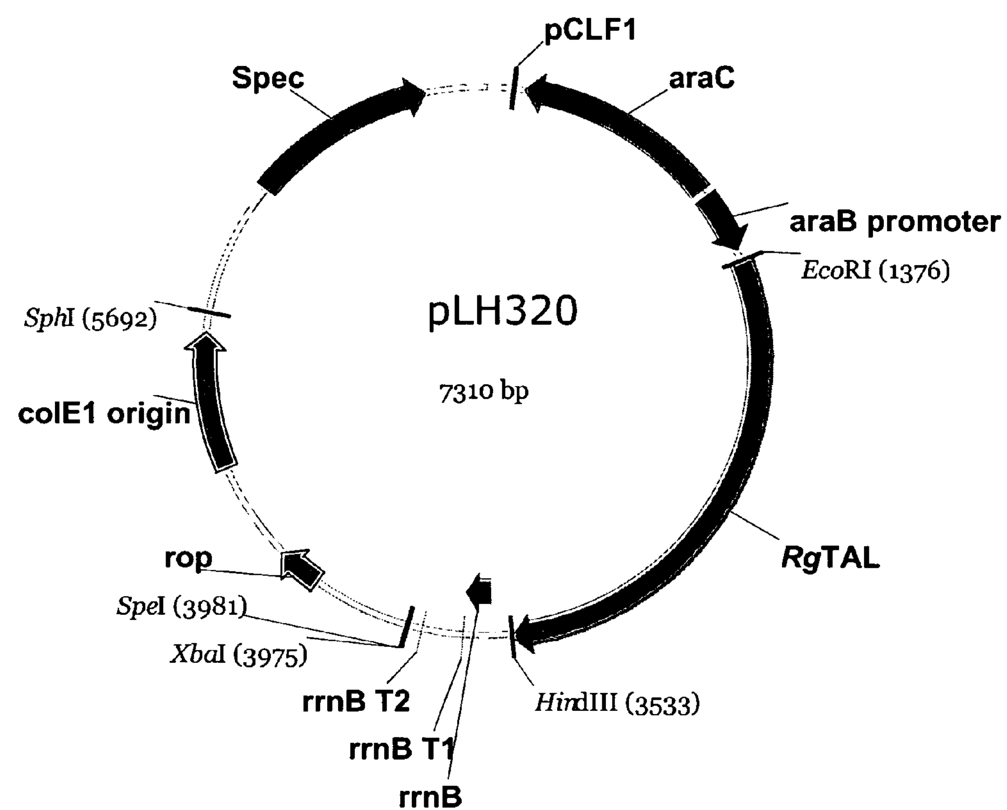
FIG. 3 shows a plasmid map of pLH320.

Strain DPD5124 carrying pLH320 was also prepared for expression of RgTAL. pLH320 is a medium copy number expression vector for the high level inducible expression of the Rg/TAL coding region. pLH320 was constructed starting with pCL1920, a low copy number plasmid with the SC101 origin of replication and spectinomycin resistance marker, obtained from Netherlands Culture Collection of Bacteria (NCCB). The *E. coli* K12 araC gene encoding the transcriptional activator for the araB promoter, and the araB promoter were cloned into pCL1920. The araC-araB region was PCR amplified as a cassette from *E. coli* strain FM5 (ATCC deposit no. 53911) genomic DNA using primers of SEQ ID NOs:18 and 19. The resulting PCR fragment was digested with AosI and HindIII, and ligated to pCL1920 digested with AosI and HindIII. Plasmid DNA of colonies resulting from transformation was isolated and assayed by restriction digestion and sequencing to confirm the desired construction, called pCL1920ara. A RgTAL coding region DNA fragment was excised from plasmid pKK223-PAL (described in U.S. Pat. No. 6,521,748) by EcoRI, HindIII digestion and ligated into EcoRI, HindIII digested pCL1920ara to give pCL1920ara.mcs.PAL. The transcription termination sequences rrnBT1 and rrnBT2 were PCR amplified from plasmid pTrc99A (Pharmacia Biotech, Amersham, GE Healthcare, Piscataway, N.J.) using primers of SEQ ID NOs: 20 and 21, and digested with HindIII, which cuts at both 5' and 3' ends of the PCR product. The rrnBT1&2 fragment was cloned into the HindIII site of pCL1920ara.mcs.PAL, 3' to the araB promoter to yield plasmid pLH312 (FIG. 2). This plasmid was converted to a medium copy number plasmid in two steps. First, a linker was inserted by site-directed mutagenesis to replace the HindIII site in pLH312 between the rrnBT2 transcription terminator and the SC101 origin of replication. This linker contains KpnI, XbaI and SpeI sites for the subsequent cloning of the colE1 replication origin. Two complementary oligonucleotides encoding the linker sequence (SEQ ID NOs:22 and 23) were used to perform a site-directed mutagenesis reaction with pLH312 as template using the Quick Change Site-Directed Mutagenesis Kit (Stratagene, San Diego, Calif.). Upon sequencing confirmation, the new plasmid was named pLH319. The colE1 replication origin and rop (encodes a replication origin protein) gene locus of pBR322 were PCR amplified using primers of SEQ ID NOs: 24 and 25. The resulting 1.8 kb PCR fragment was digested with SphI and SpeI, and ligated with pLH319 which was digested with SphI and SpeI. This yielded plasmid pLH320 (FIG. 3), which contains the colE1 replication origin in place of SC101 origin. pLH320 was transformed into *E. coli* K12 strain BW25113 [Lambda-rph-1 lacIq rrnBT14 Δ(lacZ) WJ16 hsdR514 Δ(araBAD)AH33 Δ(rhaBAD)LD78) to generate strain DPD5124. A derivative of BW25113 that contained a plasmid was obtained from Professor Barry Warnner at Purdue University. The plasmid, which was temperature sensitive, was cured from the cells by growing at high temperature to provide the BW25113 strain. BW25113 is available as CGSC#7636 from the *E. coli* Stock Center at Yale University (New Haven, Conn.).

Example 2

Identification of Strains Tolerant to High pHCA Concentration and High pH

*E. coli* K12 strains RFM793 (available from Dupont Company, Wilmington, Del.), MG1655 (ATCC #700926), W3110 (ATCC #27325), RFM443 (Drolet et al. (1995) Proc. Natl. Acad. Sci. USA. 92:3526-3530), and BW25113 (CGSC#7636, supra) were tested for tolerance to a high concentration of pHCA and high pH, as well as for the ability to produce high amounts of induced TAL activity. A deletion of the araBAD operon was made in each strain as described in General Methods, except in strain BW25113, which was already araBAD$^-$ (Ara$^-$). Each strain was transformed with pBAD.PAL3c (described in Example 1). Transformants of each strains were grown in LB medium and induced with 0.2% arabinose overnight, then used for testing PAL expression and activity and pHCA induced lysis. The pHCA induced lysis test was done by incubating fresh cells with 80 g/L pHCA, 5 g/L tyrosine in unbuffered solution at pH10. Lysis was assessed by visually screening for the presence of the TAL protein on SDS-PAGE gels in culture supernatents filtered through 0.22 M spin filters (i.e. TAL released from cells due to lysis). Zero, 4 and 21 hours of incubation were tested. Results from the 4 hour gels, given in Table 2, were that two host strains, MG1655:Ara$^-$ and FM5:Ara$^-$ had greater lysis under these conditions than the other host strains.

TABLE 2

Activity, solubility and lysis-susceptibility of TAL-expressing host strains

| Host strain, each transformed with pBAD.PAL3c | Whole cell TAL activity, Vmax/OD | Soluble extract TAL activity, Units/g protein | Insoluble total protein, μg/μL | Release of PAL at pH10, 80 g/L pHCA, 4 hr |
|---|---|---|---|---|
| RFM443: Ara+ | 0 | 7 | 0.6 | Not applicable |
| RFM793: Ara− | 413 | 172 | 0.5 | no |
| MG1655: Ara− | 440 +/− 25 | 198 +/− 3 | 0.2 | Yes |
| W3110: Ara$^-$ | 422 +/− 26 | 200 +/− 4 | 0.0 | no |
| RFM443: Ara$^-$ | 406 +/− 24 | 222 +/− 1 | 0.4 | no |
| FM5: Ara$^-$ | 464 +/− 18 | 182 +/− 12 | 0.8 | Yes |
| BW25113: Ara$^-$ | 491 | 229 | 0.2 | no |

The TAL activities in whole cell extracts, and soluble or insoluble fractions of each cell line given in Table 2 were determined as follows. The whole cell assay used cultures induced with arabinose overnight. Cell density of the overnight culture was measured before the assay was begun. One milliliter of the culture was transferred to a 15 mL tube and 20 μL of 10% Brij® 35 (Sigma) was added to permeabilize the cells. The samples were incubated at 35° C., 250 rpm for 30 mins. A 5 mM tyrosine solution was prepared by dilution of a 100 mM tyrosine stock in 100 mM CAPS, pH10. In a 96 well plate, 190 μL of the tyrosine solution was added to 10 μL of the permeabilized cells. The plates were read using a SpectraMax384 pate reader, prewarmed to 35° C. for 30 mins.

Overnight arabinose-induced cultures were harvested by centrifugation. The cells were resuspended in 50 mM Tris, pH 8.5. Four repeating cycles of 30 seconds sonicatation and 60 seconds rest were used to break open the cells. These samples were centrifuged to separate the soluble and insoluble fractions. The pellets were resuspended in 50 mM Tris, pH 8.5. The enzyme assay was then performed using UV grade cuvettes in a final volume of 1 mL. The assay buffer was the same 50 mM Tris at pH 8.5 used throughout the sample preparation. The substrate used was 1 mM tyrosine and the sample was 40 μg of crude cell free extract. The assay was performed at 25° C. and was run for 5 mins.

All results together identified three host strains having advantageous properties including high TAL activity in both assays, relatively low amounts of insoluble protein, and less lysis in the presence of high pHCA and high pH. These were W3110:Ara$^-$, the DPD4170 or DPD4171(Ara− of W3110), DPD4172 or DPD4173 (Ara− of RFM443), RFM443:Ara$^-$, and BW25113:Ara$^-$.

Example 3

Inactivation of Phenylalanine Ammonia Lyase Enzyme by GA and Lack of Biocatalyst Improvement with GA Treatment The purpose of this example was to determine the sensitivity of tyrosine ammonia lyase activity to GA and the impact of GA cross-linking of whole cells for repeated use in tyrosine to pHCA bioconversion reactions.

*E. coli* DPD5056 (RgPAL/TAL) cells expressing TAL were grown in a 200 liter Braun fermentor. Strain DPD5056 inoculum was grown in a 10 L seed tank fermentor containing the following medium $KH_2P0_4$ 2.0 g/L, $K_2HP0_4$ 13.0 g/L, $(NH4)_2HPO_4$ 4.0 g/L, $MgS0_4.7H_2O$ 1.0 g/L, yeast extract 2.0 g/L, Ferric Ammonium Citrate 0.1 g/L. The pH was adjusted to 7.0 and the medium was steam/sterilized. Post sterilization, glucose 30.0 g/L and ampicillin 50 mg/L were added. The seed tank was grown at 35° C. to about 34 $OD_{550}$ and then the entire contents was used to inoculate the 200-L fermenter. The contents of the seed tank were transferred to the larger tank with medium containing (in grams per liter): $(NH_4)_2SO_4$, 165 g; casamino acids, 3200 g; Mazu antifoam, 200 mL; $MgSO_4.7H_2O$, 160 g, yeast extract (Amberfer 40001—Marcor) 1600 g; phosphate solution, 4 L (420 g $K_2HPO_4$, 220 g $KH_2PO_4$ in 4 L deionized, distilled water); trace elements 3.2 L. Trace elements solution per L DI water contained 0.1 mL conc. $H_2SO_4$, 0.1417 g $CoSO_4.7H_2O$, 0.0782 g $NaMoO_4*2H_2O$, 0.1265 g $MnSO_4*H_2O$, 0.2263 g $CuSO_4.7H_2O$ and 0.6095 g $ZnCl_2$. Post sterilization the pH was adjusted to 7.0 and 5.3 kg glucose 60% w/w and 640 mL ampicillin at 25 mg/L were added. pH was controlled with 40% w/v $NH_4OH$ and 20% w/v $H_3PO_4$. The fermenter was controlled at 36° C., pH 6.8, dissolved oxygen (DO) tension of 25% controlled with cascade of agitation and air flow with agitation from 500 rpm and airflow from 92 to 191 SLPM. When the glucose level fell below 4 g/L a glucose feed program with 60% glucose (w/w) was initiated, first 4 h at 0.36 g/min, next 12 h at 0.73 g/min and to the end of run at 0.56 g/min. When the culture reached an $OD_{550}$ of 40, arabinose was added to final concentration of 0.5 g/L to induce TAL expression. The run ended 24.1 h after inoculation. The final cell density in the fermentation broth was an $OD_{550}$ of 120. The cells (11.8 kg) were harvested by centrifugation and stored as a frozen paste at −80° C. The TAL activity, measured as described in General Methods, was ca. 160-300 Units per g protein.

Six 50 mL centrifuge tubes were charged with *E. coli* DPD5056 paste (500 mg wet cell weight) suspended in 10 mL 50 mM HEPES, pH 7.0 buffer at ambient temperature. Each vessel received one of six specific GA treatments (weight/volume): 0.0%, 0.001%, 0.01%, 0.1%, 0.5% and 1%). The small-scale reactions were sampled and monitored for up to four hours. Aliquots (10 μL) from each of the GA-treated reactions were added to individual cuvettes containing 890 μL assay buffer, 100 μL tyrosine substrate solution and the absorbance was monitored at 315 nm as described in General Methods to determine TAL activity by the whole cell spectrophotometric cuvette assay. Only three of the reactions had any residual TAL activity after four hours of treatment: the 0% GA sample had 191 Units/g dcw; the 0.001% GA sample had 182 Units/g dcw, and the 0.01% GA sample had 19 Units/g dcw.

Following the GA treatment, the cells were washed three times with 0.1 M CAPS buffer adjusted to pH 10 and the cells were recovered by centrifugation after each wash. Following the washes, the recovered cell pellets were resuspended in 5 mL 50 mM tyrosine in water adjusted to pH 10. One milliliter of this suspension (containing 100 mg wet cell weight, ca. 28 mg dcw TAL cells) was added to a 50 mL polypropylene centrifuge tube charged with 19 mL of 50 mM tyrosine solution adjusted to pH 10. The reaction tubes were secured in an incubator/shaker and rotated at 200 rpm and 35° C. The tube reactions were sampled by HPLC analysis to determine their initial rate of tyrosine conversion to pHCA. The reactions were allowed to continue reacting for 24 hours, then sampled again to ensure full consumption of the tyrosine substrate. The cells were harvested by centrifugation, rewashed with 0.1 M CAPS buffer, pH 10, then transferred to the original reaction tubes containing 20 mL of fresh tyrosine substrate and returned to the incubator/shaker for another reaction cycle. This process was repeated for a total of six cycles. There was no realized enhancement in the recycle stability with the use of 0.01 or 0.001 wt % GA pre-treated TAL cells as the catalyst in the tyrosine bioconversion reactions.

Example 4

TAL Biocatalyst Inactivation Using Standard Methods for GA/PEI Cross-Linking of Biocatalyst/Alginate Beads The purpose of this example is to illustrate the sensitivity of the TAL biocatalyst to immobilization in alginate beads using standard GA cross-linking conditions.

Cells were grown as described in Example 3 above. The immobilization was conducted following the conditions described in WOP2002072856A2, which is herein incorporated by reference. The levels of GA and PEI per gram of beads were $1.3\times10^{-2}$ g GA per gram of beads and $2.5\times10^{-2}$ g PEI per gram of beads. The beads were assayed by placing 20 beads (20 beads ~0.0998 g wet cell weight of TAL cells) in both 90 mL 2 mM phenylalanine, 50 mM Tris, pH 8.5 buffer and 90 mL 2 mM tyrosine, 50 mM Tris, pH 8.5 buffer. Two additional control reactors were run along with the bead reactors: a second vessel was charged with 0.1 g (wet cell weight) of whole, unimmobilized TAL cells from the same source as the cells in the beads; a third reaction vessel was charged with a solution containing TAL cell-free extract (100 mg protein). The reaction contents were uniformly suspended by stirring at a moderate rate. Every few minutes, a 0.40 mL sample from each reaction bottle was removed. The samples from the "bead" reaction and "whole cell" TAL reaction bottles were immediately micro-filtered using Eppendorf filter centrifuge tubes to separate the catalyst from the substrate and terminate the reaction. For the "cell-free extract" reaction, the 0.40 mL assay samples were incubated in a 90° C. water bath for 5 minutes, then micro-filtered (the high heat quickly inactivates TAL activity in the cell-free extract). The filtered samples were then diluted and analyzed by HPLC as described in General Methods. Enzyme activity was measured by monitoring the depletion of the substrate and the formation of the product. The HPLC results showed that the reaction bottles with whole TAL cells and TAL cell-free extract had high activity within the first few minutes of the reaction, which is typical for these forms of the TAL catalyst. The GA and PEI treated calcium alginate TAL beads of this specific example showed no activity, even after one hour in contact with the phenylalanine or tyrosine substrate.

Example 5

Preparation of Active, Lightly Cross-Linked 2.75 wt. % Alginate Beads with 7.5% Dry Cell Weight (dcw) Strain DPD4574 with Accumulated RgTAL This Example illustrates the preparation of calcium alginate beads containing cells of RgTAL-expressing strain DPD4574 with low levels of GA cross-linking. The GA is used at 2% of the amount used in Example 4, and PEI is used at 25% of the amount used in Example 4.

Part A: Preparation of DPD4574 Cells with TAL Activity

*E. coli* DPD4574 cells were grown in a 10 liter Braun BiostatC fermentor with an initial volume post inoculation of 8.0 liters of medium containing (in grams per liter): $K_2HPO_4$, 3.3 g/L; $MgSO_4.7H_2O$, 2.0 g/L; $(NH_4)_2NO_3$, 0.3 g/L, Ferric Ammonium Citrate, 0.10 g/L; yeast extract (Amberfer 40001—Marcor) 2.00 g/L, Trace Elements, 1.6 mL/L; and Biospumex153K (100%), 0.5 mL/L. Post sterilization, the pH was adjusted to 7.0 and 212 g glucose 60% w/w and ampicillin 50 mg/L were added. pH was controlled with 40% $NH_4OH$ and 20% w/v $H_3PO_4$. Trace elements solution: In 1 L D water, 0.1 mL conc. $H_2SO_4$, 0.1417 g $CoSO_4.7H_2O$, 0.0782 g $NaMoO_4*2H_2O$, 0.1265 g $MnSO_4*H_2O$, 0.2263 g $CuSO_4.7H_2O$ and 0.6095 g $ZnCl_2$.

Strain DPD4574 inoculum was grown in a 2.0 L shake flask containing 500 ml of the following medium (in grams per liter) $KH_2PO_4$ 2.0 g/L, $K_2HP0_4$ 13.0 g/L., $(NH_4)_2HPO_4$ 4.0 g/L, $MgS0_4.7H_2O$ 1.0 g/L, yeast extract 2.0 g/L, Ferric Ammonium Citrate 0.1 g/L. pH was adjusted to 7.0 and the medium was steam/sterilized. Post sterilization glucose 30.0 g/L and ampicillin 50 mg/L were added. The culture growth was in 2 L flasks with 500 mL medium and 35° C. to about 2 $OD_{550}$ and then the entire contents was used to inoculate the fermenter.

The fermenter was controlled at 36° C., pH 6.8, dissolved oxygen (DO) tension of 25% controlled with cascade of agitation and air flow with agitation from 400 to 1000 vrpm and airflow from 2 to 16 SLPM, the overhead pressure was 0.5. When the glucose level fell below 4 g/L a glucose feed program with 60% glucose (w/w) was initiated, first 4 h at 0.36 g/min, next 12 h at 0.73 g/min and to the end or run at 0.56 g/min. When the culture reached an $OD_{550}$ of 35, arabinose was added to a final concentration of 0.5 g/L The run ended 20 h after arabinose addition. The final cell density in the fermentation broth was an $OD_{550}$ of 90 and the final volume was about 9 liter. The g dcw/L was determined assuming that 1.0 $OD_{550}$ contained 0.33 g dcw/L=30 g dcw/L.

The cells were harvested by centrifugation and stored as a frozen paste at −80° C. The TAL activity was assayed as described in General Methods and the result was about 118 Units per g dcw.

Part B: Preparation of Alginate/*E. coli* Cell Suspension at 2.75 wt. % Alginate, 7.5% dcw Cells.

A 2 L waste jug equipped with an overhead stirrer was placed in a water bath at room temperature and charged with 1373 mL distilled, deionized $H_2O$. 75.9 g of sodium alginate (FMC Protanal LF 10/60 FMC-Biopolymers, Norway) was slowly added to the briskly stirred solution (1449 mL total volume, 5.24% alginate). The jug was covered with a cap (but not sealed) and heated until the water bath temperature reached 80° C. The suspension was mixed at the highest rate possible until the alginate was completely dissolved. After the alginate was dissolved, the solution was allowed to cool to 25° C. Previously frozen *E. coli* DPD4574 (588 g, where 28% equals dry cell weight) was added along with 723 mL distilled, deionized water (1311 mL total volume, 15.79% dcw cell suspension) to the alginate mixture stirring at 25° C. The mixture was stirred until the cells were uniformly suspended in the alginate solution.

Part C: Bead-Making.

Calcium acetate solution (14.72 L of 0.2 M $Ca(OAc)_2.xH_2O$, adjusted to pH 7.0 using acetic acid) was poured and divided evenly into four 6 L capacity pails. A pail was placed on a stand and equipped with an overhead stirrer. A peristaltic pump, equipped with Masterflex® tubing (Part #: L/S 16, Cole Parmer 06508-16), was attached to a 17-needle die (ESI 304-26791) via a hose clamp adaptor. The die was clamped to a stand and was set up so that the distance between the needles and 0.2 M $Ca(OAc)_2$.xH2O solution in the pail was at least 8 inches. The die needles were offset from the center of the pail and the solution vortex while stirring. The multi-needle die contained 18-gauge needles that were cut down to ca. 5 mm in length with the tips squared off. The overhead stirrer was used to stir the solution at a rate fast enough to keep the forming beads suspended in solution (this rate was determined while the beads were being produced). The tubing line was filled with the alginate/cell suspension and the syringe pump was turned on, so that the suspension dripped into the calcium acetate hardening buffer at a pump setting equivalent to 2.0 mL/min per needle (with a MasterFlex® digital pump Model # LS2, this corresponded to a flow rate of ~35 mL/min). Beads formed as the alginate/cell suspension contacted the calcium acetate solution, forming a suspension of alginate beads containing cells. After one-fourth volume of the alginate/cell suspension was consumed and beads were made in a single bucket, the bucket was transferred to an incubator/shaker and anchored so the vessel was stable to gentle agitation (ca. 75 rpm). The alginate/cell suspension was dripped into the second, third and fourth pails until the solution was consumed. The agitation of suspension in the pail was just sufficient to keep the beads suspended without damaging the resultant beads. After all additions were completed, the beads were allowed to remain in 0.2 M $Ca(OAc)_2.xH_2O$, pH 7.0 solution for 2 h at 25° C. under gentle agitation.

Part D: Crosslinking

The 0.2M calcium acetate, pH 7.0 solution was decanted and approximately 50 percent of the volume was retained. Using a large coarse, glass-fritted funnel, the beads (2001 g) were recovered, then resuspended in the decanted buffer, using approximately 2.44 mL buffer/g beads. While the bead-containing solution was stirred by the overhead stirrer, two grams of 25% (w/w) GA in water (JT Baker M752-07, 25% in water) was added dropwise to the beads (corresponds to adding 0.02 g of 25 w/w % GA per 20 g beads). The mixture was stirred for 1 h at 25° C. With stirring, 100 g of 12.5% (w/w) polyethylenimine (PEI; BASF Lupasol PR971L, 25% in water) in water was added dropwise. This is 1 g of 12.5% w/w PEI solution per 20 g beads. The mixture was stirred overnight (16-18 h) at 25° C. The buffer was decanted from the beads, then the beads were washed twice with 5 mM $CaCl_2.2H_2O$ buffer (calcium chloride, dihydrate, FW 147; Sigma 223506) for 15 min, using 3.0 mL buffer per gram of beads. The beads were transferred into two plastic 8-L jugs that contained sufficient volume of 5 mM $CaCl_2.2H_2O$ such that beads were covered by a 2-inch height of buffer and stored at 5° C.

This bead biocatalyst preparation was denoted as T4574-A. The diameter of the formed beads was about 3.0 mm. The bead cross-linking treatment used $2.5\times10^{-4}$ g GA and $6.3\times10^{-3}$ g PEI per gram of beads. The GA treatment of T4574-A was 0.13% of the GA treatment of beads described in Birnbaum et. al, supra; the PEI treatment of T4574-A was 6.3% of the PEI treatment of beads described in Birnbaum et al.

Example 6

Recycle Experiments to Evaluate TAL Catalyst Stability Upon Immobilization

This Example demonstrates significantly improved stability upon immobilization of the pHCA tolerant TAL biocatalyst DPD4574. Stability was evaluated by measuring the recovered TAL activity yields after successive bioconversion reactions. A comparison of free whole TAL cells and immobilized TAL cells was performed for both TAL catalysts *E. coli* DPD5056 and *E. coli* DPD4574. The free whole TAL cells were grown, harvested and stored as described in Examples 3 and 5. The immobilized DPD5056 cells were grown as described in Example 3 and immobilized using the low GA/PEI conditions described in Example 5. The immobilized DPD4574 TAL cells were T4546-A beads as described in Example 5.

Cel-Stir® reactors (Wheaton) provided the best stirring efficiency as the overhead stirring mitigated crushing of immobilized beads. General steps for pHCA production involved pre-warming of the tyrosine substrate buffer, the transfer of the solution to a pre-warmed reactor, and addition of TAL catalyst where a fixed concentration of cells at 2.5 wet cell wt % was maintained. Cells (frozen at −80° C.) were suspended in 50 mM N-Cyclohexyl-2-aminoethanesulfonic acid (CHES). CHES buffer was used because it had good buffering capacity in the region between pH 9.0 and 10.5, a range that brackets the range of interest for the TAL biocatalyst. The buffer composition was 12.5 mM tyrosine and 50 mM CHES, pH 9.8 for use at 30° C. A 50 mL CelStir® jacketed reactor (Wheaton) was charged with 22-23 mL of the buffer solution (pre-warmed to 30° C.) and allowed to equilibrate with stirring. When whole cells were used as the catalyst, a pellet of frozen cells (circa 100 mg) was weighed into a 50 mL centrifuge tube, suspended in 2-3 mL of 50 mM CHES, pH 9.8 buffer and added to the reactor; the final reaction volume was 25 mL. 50 μL suspensions at specific time intervals (circa 30, 60, 90 and 120 min) were removed from the CelStir® reactors and the samples were immediately centrifuged to separate the cell catalyst from the medium; the filtrate was processed for HPLC analyses. The initial rate of pHCA production was determined and was used as a measure of TAL catalyst activity. For the whole cell reactors, there was a loss of ~2% cell weight in each cycle due to reaction sampling and the change was noted in calculating TAL activity (Units per gram dcw). At end of each pHCA production cycle: after recovery of cells by centrifugation (16,000×g, 20 min, 4° C.), the cells were incubated in 0.25 M pHCA, pH 10.01 for at least 1 hour to simulate the higher pHCA endpoint concentrations achieved in large scale bioconversion reactors where pH control can be managed. The cells were washed twice with EPPS, pH 9.0 buffer before repeating another reaction cycle in the CHES and tyrosine solution. These steps were repeated until the TAL activity was greatly reduced. When the above reaction was conducted at 35° C., the measurement of TAL activity by HPLC analyses was typically consistent with the TAL whole cell spectrophotometric activity assay. For example, the HPLC method yielded an activity of ca. 200 Units per g dcw for TAL cells DPD5056; the whole cell spectrophotometric assay yielded an activity ranged between 150 and 300 Units per gram dcw.

When the recycle reactions were performed with immobilized TAL beads, the reactors were nearly identical to those described above for free whole cell catalyst except for the following differences: the beads were blotted free of solution and weighed to represent about 100 mg wet cell weight TAL cells (circa 260 to 345 mg beads) and transferred to a 12.5 mM tyrosine, 50 mM CHES, pH 9.8 solution containing 5 mM calcium chloride. At the conclusion of the reaction cycle, the solution was simply decanted from the beads, the beads were washed in 5 mM calcium chloride solution and the cycle was repeated. Since the beads were never removed in the reaction sampling for HPLC analyses, it was not necessary to correct for catalyst loss between cycles.

Figure 4:
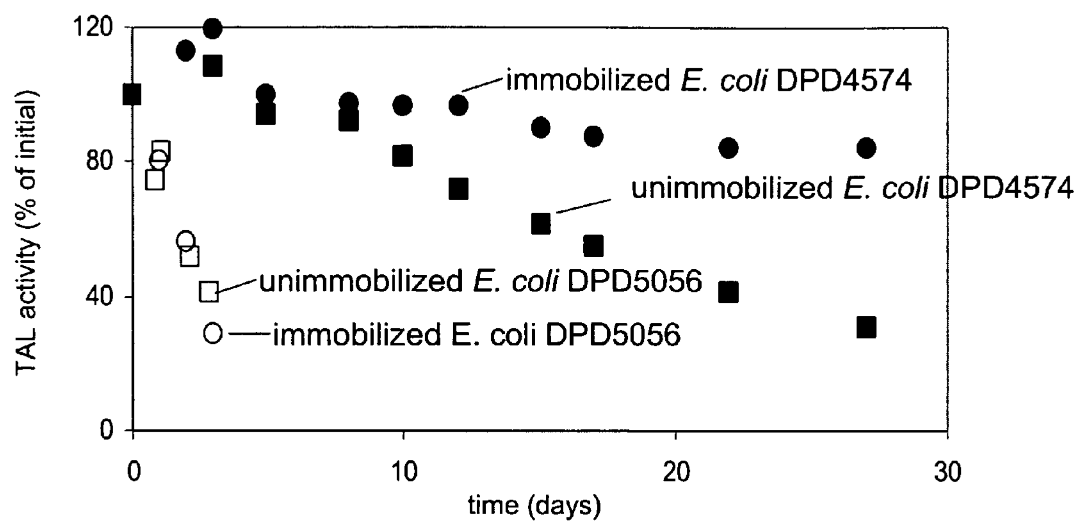
FIG. 4 shows a graph of the % of initial TAL activity present over extended times in immobilized and unimobilized strains DPD5056 and DPD4574.

A graph of the % of initial TAL activity present over extended times in immobilized and unimobilized strains DPD5056 and DPD4574 is shown in FIG. 4.

Example 7

Production of Repeated pHCA Batches from 50 g/L Tyrosine using Immobilized DPD4574 Containing RgTAL (T4574-A) at 30° C.

Figure 5:
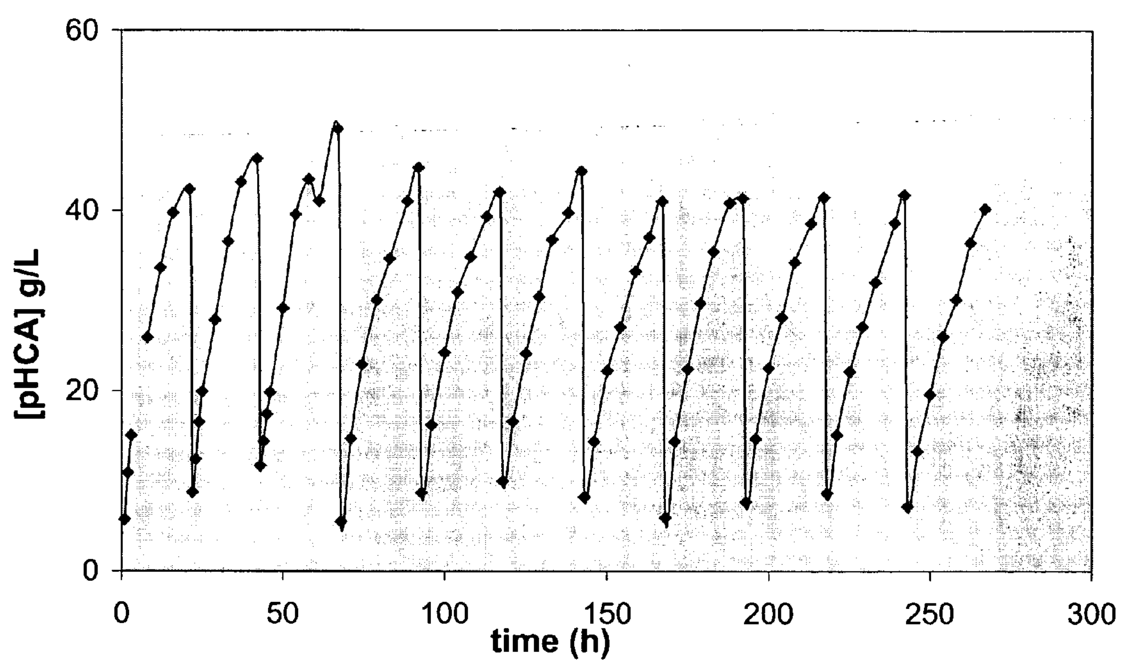
FIG. 5 shows a graph of pHCA production in successive recycles of RgTAL catalyst calcium alginate immobilized DPD4574, pH 9.9, T=30° C.

This Example illustrates the repeated use of the GA/PEI calcium alginate immobilized DPD4574 biocatalyst to convert a reaction mixture with high tyrosine solids to a high pHCA concentration at an elevated pH. The reaction vessel used was an Applikon Biotechnology (Foster City, Calif.) BioBundle™ glass autoclavable bioreactor system containing a 3 L fermentation vessel, ADI 1010 Controller, 10225 Cabinet, a fixed speed pump, pH/DO probes and a heating blanket. The run parameters were at the following settings: temperature, 30° C.; pH, 9.9; agitation rate, 200 rpm; working volume, 1.0 L; TAL cell catalyst, 13 g dcw; gas outlet open. The reactor was charged with 500 mL 10 mM calcium chloride solution and titrated to pH 9.8 using 50% w/w sodium hydroxide. TAL catalyst (188 g beads T4574-A that were prepared as described in Example 5) was added and rinsed into the reactor with 112 mL distilled, deionized water. The bead solution was mixed for 15 minutes and equilibrated to the set temperature before addition of a tyrosine slurry (50 g tyrosine, 100 mL water). The vessel containing the tyrosine-slurry was rinsed with 50 mL water to capture any residual tyrosine and to bring the initial working volume to 1.0 L. The pH control was turned on, and the reactor was set for operations at pH 9.9 using 25% w/w sodium hydroxide as the titrant. This marked the start of the reaction cycle. Aliquots (circa 1-2.5 mL) were removed by a 5 mL serological pipet through the sample port at 1 h, 2 h, 3 h, 4 h, 8 h, 12 h, 16 h, 21 h. The aliquots were centrifuge-filtered and diluted with water (25×, initial times; 500× later time points) for HPLC analyses to measure pHCA production and soluble tyrosine in the reactor. The reactor was terminated and turned over for another cycle by shutting down the temperature and pH controls. The clear supernatant was transferred out of the reactor either by peristaltic pump or removed by pipetting. The supernatant was transferred into a 1 L centrifuge bottle for storage. The beads were washed with 300 mL 5 mM calcium chloride. After 15 minutes, the wash solution was removed and the bead reactor was re-charged with fresh 5 mM calcium chloride solution (500 mL). Every step-except for loading of beads—was repeated in the same order as described for the first cycle. This was repeated ten times for a total of eleven reaction cycles using the same 188 g beads in all 11 cycles. FIG. 5 shows the pHCA concentration accumulation in each of the eleven cycles. In nearly every reaction cycle, the final concentration of pHCA equaled or exceeded 40 g/L. This Example demonstrated the superior stability of the immobilized TAL catalyst and the greater simplicity of a process employing immobilized TAL beads as compared to recycling whole cells which typically could be reused for five reaction cycles, as non-immobilized cells quickly lost TAL activity and the process to recover and reuse the whole cell catalyst was complex.

Example 8

Preparation of Active, Low-Level Cross-Linked 2.75 wt. % Alginate Beads with 8.6% dcw Strain DPD5124 with Accumulated RgTAL This Example illustrates the preparation of calcium alginate beads containing cells of RgPAL expressing strain DPD4574 with levels of GA cross-linking that are 12.5% higher than used in Example 5, but still only 1.625% of levels used in Birnbaum et al, supra. The retention of activity in the TAL-containing biocatalyst upon exposure to the higher GA levels was achieved by controlling the rate of GA addition to the beads. GA was added at a rate that did not exceed about $1\times10^{-4}$ g GA/g bead per min.

Part A: Preparation of *E. coli* K12 DPD5124 Cells.

The fermentation was carried out in a 10 L Braun BiostatC fermenter. A vial lot of DPD5124 was prepared and frozen from a single colony of DPD5124 grown on a plate with LB medium containing spectinomycin (50 μg/mL). The general protocol was as follows: The fermentation seed was grown in 500 mL seed medium ($KH_2PO_4$, 2 g/L; $K_2HPO_4$, 13 g/L; $(NH_4)_2SO_4$, 4 g/L; $MgSO_4.7H_2O$, 1 g/L, yeast extract (Amberferm 4001), 2 g/L, ferric ammonium citrate, 0.1 g/L; glucose, 15 g/L and spectinomycin, 50 μg/mL) in a 2 L flask, at 35° C. and 300 rpm, to a final $OD_{550}$ of ~2.0. The entire seed culture was transferred to the fermenter to start the experiment. The fermenter contained 8 L (post inoculation) of medium ($H_2SO_4$, 0.5 mL/L; $H_3PO_4$, 2.9 mL/L; KOH, 0.3 mL/L; citric acid monohydrate, 1.9 g/L; $MgSO_4.7H_2O$, 1.1 g/L; $FeSO_4\,7H_2O$, 0.2 g/L; $CaCl_2\,2H_2O$, 0.1 g/L; yeast extract (Amberferm 40001) 2 g/L, antifoam, 0.5 mL/L, trace element solution, glucose and spectinomycin, 50 μg/mL) and was controlled at 25% dO, pH 6.8 (controlled with $NH_4OH$), and 36° C. Glucose was fed by a controlled specific growth rate of μ=0.2 to maintain limiting concentrations. At the time of TAL induction by arabinose the temperature was shifted from 36° C. to 30° C. Arabinose was added (to a final concentration of 0.3 g/L) to the fermenter when the optical density (OD) was 35. Samples were removed from the fermenter in 3 hour intervals, and analyzed for OD (at 550 nm) and glucose by enzymatic assay. The final OD was 79. Samples were centrifuged, and pellets frozen for later TAL activity analyses. The TAL activity was 206 Units per g dcw.

Part B: Preparation of Alginate and *E. coli* Cell Suspensions.

Frozen DPD5124 cell paste (640 g) was pre-weighed and placed in a large polyethylene bag, sealed and kept at −70° C. until needed. On the morning of the bead preparation, the cells were transferred to the refrigerator to soften and thaw for use. A large magnetic stir bar and 896 mL of distilled deionized water were placed in a large wide-mouth jar. The vessel was transferred into a water bath atop a heater/stirrer. While the water solution was stirred briskly, alginate (49.5 g Protanal®) was slowly added over a 28 minute period. During this period the temperature rose from ambient to 65° C. After the alginate was completely added (945 mL total volume, 5.24% alginate), the water bath was heat to 80° C. The suspension was mixed at the maximum rate possible and with vigorous hand mixing with a spatula until the alginate was completely dissolved. The solution was allowed to slowly cool to ambient temperature. Chunks of the 640 g of wet cell paste of *E. coli* strain DPD5124 (24% dry cell weight, dcw=153.6 g) were added to the cooled alginate solution. The thawing cell chunks were broken and blended with the alginate solution using a spatula when necessary. After all of the large chunks were added, the remaining cell paste was suspended in 215 mL distilled deionized water and transferred to the jar. The alginate solution and cell paste were homogenized (855 mL total volume, 13.53% dcw cell suspension) until a smooth slurry was achieved and the cells were fully suspended in the alginate solution. This mixture was kept at 25° C. until the bead-making step. Complete homogenization of the cell paste into the alginate solution took ~60 minutes.

Part C: Set-Up and Bead-Making.

Calcium acetate buffer (10 L, 0.2 M calcium acetate, pH 7.0) was divided into 3 lots of 3.2 L each and poured into three secondary pails. The bead-making die, described in Example 5, was set up with L/S 16 Masterflex® Tubing (Cole Parmer 06508-16), circa 2.5 feet length feeding from the cell paste suspension. The needle was offset from the solution vortex, with the left-most edge of the die about 1 inch away from the edge of the pail containing the calcium acetate hardening buffer. The distance between the end of the needles and the surface of the hardening buffer was initially 12 inches. It was re-adjusted to a 15-inch height after 5 minutes so that the cell/alginate paste formed a nice drop prior to contacting the calcium acetate solution. The tubing was connected through a Masterflex® LSII Pump head and set for 35 mL/min flow rate out of the #16 tubing. One third of the cell paste was dripped in (circa 20 minutes) before stopping the pump and switching to another bucket with 0.2 M calcium acetate, pH 7.0 buffer and continuing with the bead making. This was repeated a third time until all of the cell/alginate paste was consumed. The agitation of the beads in the pail with the hardening bucket was just sufficient to keep the beads suspended. Beads were allowed to harden in the 0.2 M calcium acetate, pH 7.0 buffer solution for 2 hours.

Part D: Cross-Linking.

Using a large coarse glass-sintered filter, the hardened beads were filtered to obtain a crude wet yield of 1480 g. A portion of the beads (200 g) was removed immediately to evaluate the effect of reversing the reagent addition order (see Part D below for description of these bead preparations). The remaining 1280 g of beads were resuspended in 3123 mL of decanted spent calcium acetate, pH 7.0 buffer (using 2.44 mL buffer/g beads) and slowly stirred to keep the beads suspended. GA solution (18.5 g of 25% (w/w) solution, this represents 0.25 g of 25 w/w % GA solution per 20 gram beads) was diluted with 5.5 g calcium acetate buffer for a final volume of ~25 mL solution. This solution was added dropwise via a pump at a rate of 0.3 mL/min over 69 minutes to the 1280 g beads. At 10', 20' and 40' an aliquot of beads (circa 65 g) was removed, filtered and transferred to a smaller wide-mouth jar with a magnetic stir bar and ~160 mL spent calcium acetate, pH 7.0 buffer. The GA exposures of these three bead preparations were $3.8\times10^{-4}$ g GA per g bead, $7.5\times10^{-4}$ g GA per g bead and $1.7\times10^{-3}$ g GA per g bead, respectively. Each jar was set on a stirrer and stirred gently until the GA addition in the large bead batch was completed. After the completion of the GA addition to the larger batch of beads, all bead-GA-containing solutions were allowed to stir for an additional 1 hour before adding PEI solution (at 12.5 wt %). Each bead preparation had the PEI solution added as indicated below (PEI quantity equal to 1 g of 12.5% w/w PEI solution per 20 g beads). All reaction mixtures were allowed to stir overnight for 16 h. After the overnight PEI treatment, the buffer was decanted and the beads were washed twice with 5 mM calcium chloride solution, for 15 minutes. The beads were split into 2 secondary jugs and suspended in 5 mM calcium chloride. All storage jars/jugs were capped and stored cold at 5° C. until use. The resulting bead preparation samples are listed below.

a. T5124-A added 3.1 g PEI solution to 62 g beads treated with $3.8\times10^{-4}$ g GA per gram of beads
b. T5124-B added 3.35 g PEI solution to 67 g beads treated with $7.5\times10^{-4}$ g GA per gram of beads
c. T5124-C added 3.75 g PEI solution to 75 g beads treated with $1.7\times10^{-3}$ g GA per gram bead
d. T5124-D added 54 g PEI solution to 1080 g beads treated with $3.4\times10^{-3}$ g GA per gram bead Part E: Reversed Reagent Addition PEI solution (12.5%, 10 g) was added to the jar with 200 g beads in 480 mL spent calcium acetate, pH 7.0 buffer. The mixture was allowed to stir overnight at ambient temperature. This PEI-treated bead preparation was split into three aliquots, and transferred to separate jars that were labeled e, f and g. A magnetic stir bar was added to each jar and the quantity of GA (25 wt % solution) indicated below was added to each sample over a period of 60 minutes:

e. T5124-E 0.91 g GA solution (25 w/w %) was added to 62 g PEI-treated beads; this corresponds to $3.4\times10^{-3}$ g GA/g beads f. T5124-F 1.68 g GA solution (25 w/w %) was added to 57 g PEI-treated beads; this corresponds to $7.4\times10^{-3}$ g GA/g beads g. T5124-G 3.25 g GA solution (25 w/w %) was added to 55 g PEI-treated beads; this corresponds to $1.5\times10^{-2}$ g GA/g beads The GA-treated PEI-coated beads were allowed to continue reaction overnight at 5° C. before washing with 10 mM calcium chloride solution. Beads were then placed in jars containing 10 mM calcium chloride and stored at 5° C. until use in pHCA-producing reactions as described in Example 6. The diameter of the formed beads was about 3.0 mm.

All seven bead preparations were assayed for tyrosine ammonia lyase activity by mixing 300 mg bead catalyst in 25 mL volume of assay buffer (12.5 mM tyrosine, 50 mM N-Cyclohexyl-2-aminoethanesulfonic acid (CHES), pH 9.8 buffer, 10 mM calcium chloride, for use at T=35° C.). Rates of pHCA formation at 35° C. were measured by HPLC analyses on aliquots removed at time intervals between 15 and 120 minutes and results are given in Table 3. The results indicate that careful, metered reagent addition can overcome TAL sensitivity to GA and achieve high activity in alginate immobilized bead preparations of higher GA cross-linking density than in Example 5, but still much lower than used in the art.

TABLE 3

TAL activities in different DPD5124 strain bead preparations.

| Sample Label | First Cross-linker | GA g/g beads | PEI g/g beads | TAL activity (g pHCA produced/L/h per g dcw bead catalyst |
|---|---|---|---|---|
| TAL5124-A | GA | $3.8 \times 10^{-4}$ | 0.0063 | 7.97 |
| TAL5124-B | GA | $7.5 \times 10^{-4}$ | 0.0063 | 7.82 |
| TAL5124-C | GA | $1.7 \times 10^{-3}$ | 0.0063 | 7.23 |
| TAL5124-D | GA | $3.4 \times 10^{-3}$ | 0.0063 | 6.08 |
| TAL5124-E | PEI | $3.4 \times 10^{-3}$ | 0.0063 | 7.96 |
| TAL5124-F | PEI | $7.8 \times 10^{-3}$ | 0.0063 | 6.95 |
| TAL5124-G | PEI | $1.5 \times 10^{-2}$ | 0.0063 | 1.95 |

Example 9

Production of Repeated pHCA Batches from 50 g/L Tyrosine Using Calcium Alginate Bead Immobilized DPD5124 Containing RgTAL (T5124-D)

This example illustrates the use of GA/PEI cross-linked calcium alginate beads containing RgTAL in 41 reaction cycles for 980 hours of continuous use in the bioconversion of tyrosine to pHCA.

Figure 6:
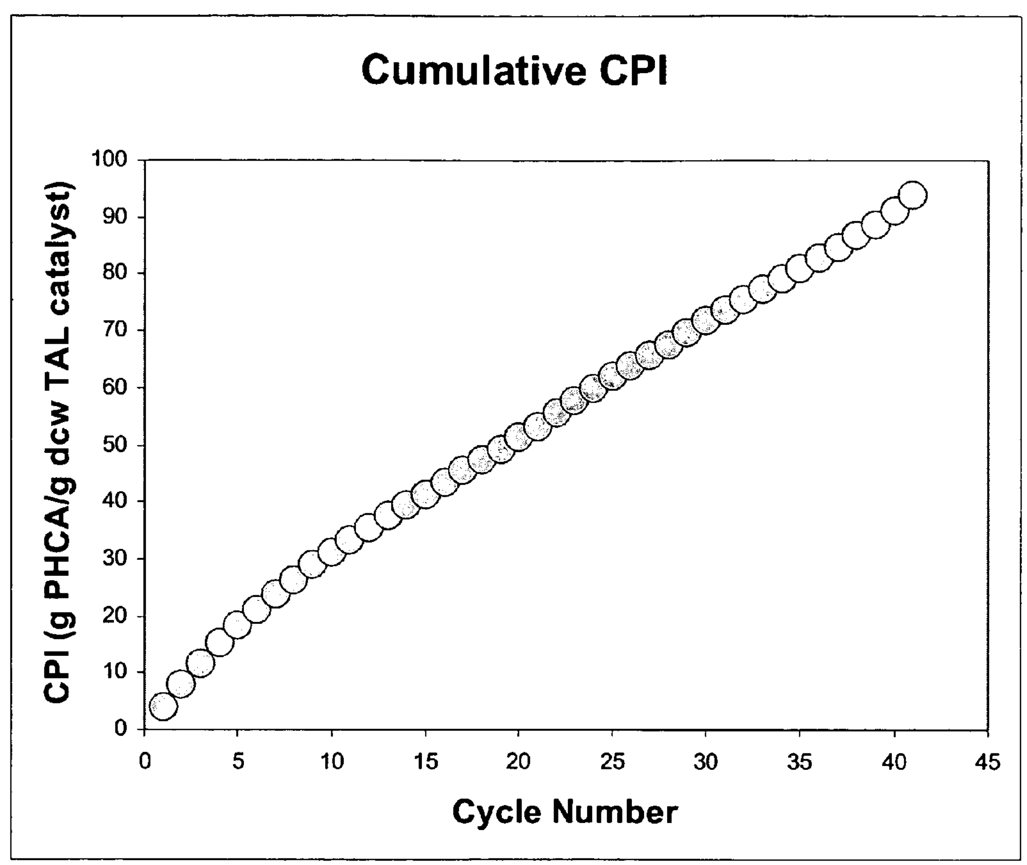
FIG. 6 shows a graph of cumulative cell productivity index (CPI: g pHCA produced per g dcw TAL catalyst) in forty-one cycles of RgTAL catalyst calcium alginate immobilized DPD5124.

The reaction vessel used was an Applikon Biotechnology (Foster City, Calif.) BioBundle™ glass autoclavable bioreactor system containing a 3 L fermentation vessel, ADI 1010 Controller, 10225 Cabinet, a fixed speed pump, pH/DO probes and a heating blanket. The run parameters were at the following settings: temperature, 30° C.; pH, 9.8; agitation rate, 125 rpm; working volume, 1.5 L; TAL cell catalyst, 16.6 g dcw; gas outlet open. The reactor was charged with 900 mL prewarmed (30° C.) 10 mM calcium chloride solution and titrated to pH 9.8 using 25% w/w sodium hydroxide. Tyrosine (75 g tyrosine) was added as a slurry in 300 mL water and the residual tyrosine in the transfer beaker was rinsed with 160 mL water and added to the Applikon reactor. The reactor was set for operations at pH 9.8, temperature=30° C. When the pH and temperature were stable, the TAL catalyst (192 g beads T5124-D as prepared in Example 8) was added to initiate the reaction. Aliquots (circa 1-2.5 mL) were removed by a 5 mL serological pipet through the sample port at run times of 3 min, 30 min, 60 min, 90 min, 120 min and end-of-run (circa 24 h). The aliquots were centrifuge-filtered and diluted for HPLC analyses to quantify pHCA production and soluble tyrosine in the reactor. The reactor was terminated and turned over for another cycle by shutting down temperature and pH control. The clear supernatant was transferred out of the reactor either by peristaltic pump or removed by pipetting. The beads were not washed between cycles except after cycles 29, 32, 33 and 39. After those four cycles, the beads were washed with 300 mL 10 mM calcium chloride. Every step, except for loading of beads,—was repeated in the same order as described for the first cycle; the beads remained in the Applikon bioreactor and were reused. This process was repeated forty times for a total of forty-one reaction cycles to achieve a cumulative cell productivity index of 100. The following process parameters were altered during the 980 hours of continuous operation: the base titrant was changed to 50% w/w sodium hydroxide for cycles 2-41; the temperature was changed several times: between cycles 11 and 30, the temperature was set at 30° C.; between cycles 31 and 35, the temperature was increased to 32° C. and between cycles 36 and 41, the operating temperature was increased to 35° C.; the agitation rate was altered to 175 rpm for cycles 5-18 and 200 rpm for cycles 19-41; the working reaction volume changed from 1.5 L in cycles 1 to 9; 1.25 L in cycles 10 and 11 and 1.01 L in cycles 12 to 41. FIG. 6 shows the cumulative pHCA produced per cycle per g dcw catalyst (9.2 g dcw DPD5124 in 192 g beads). After 41 cycles, the cumulative CPI was 94±10 g pHCA per g dcw DPD5124. The beads after forty-one cycles looked physically similar to unused beads. The results in this Example demonstrated the extraordinary long-term operating stability of the immobilized TAL catalyst. The lifetime far exceeds extended times described previously by others using PAL/TAL catalysts.

Example 10

Identification of TAL Open Reading Frame in *P. chrysosporium* Genome

This example describes the identification of a DNA sequence from the fungus *Phanerochaete* chrysosporium that encodes a new PAL/TAL protein, which is the subject of co-owned and co-pending U.S. patent application Ser. No. 11/485,558, herein incorporated by reference.

The amino acid sequence of the PAL/TAL protein from the fungus *Trichosporon cutaneum* (*T. cutaneum*; SEQ ID NO:3; disclosed in U.S. Pat. No. 6,951,751) was used in a tBLASTN search of the genomic sequence of *P. chrysosporium. P. chrysosporium* is a fungus with an optimum growth temperature of 40° C. The genome of *P. chrysosporium* has been sequenced and is available at; DOE Joint Genome Institute, US Dept. of Energy; Martinez et al. (2004) Nature Biotechnology 22, 695-700). The results revealed a region on contig 12 (1144981-1147415, on the complementary strand) that encodes amino acid fragments having extensive sequence similarity with the PAL/TAL enzyme of *T. cutaneum*. The probability that this alignment is random is $e^{-128}$, suggesting a very high level of confidence for the sequence alignment. A tBlastN (Altschul et al., *J. Mol. Biol.* 215:403-410 (1990)) analysis of the comparison of translations in all 6 reading frames of the *P. chrysosporium* genomic sequence using the

*Trichosporon cutaneum* PAL/TAL amino acid sequence (SEQ ID NO:3) as the query was done. With introns removed, the identified *P. chrysosporium* genomic region contained a single open reading frame (e_gwh2.12.71.1) that had been annotated as a potential PAL/TAL gene based on sequence similarities to other ammonia lyases. This ORF (SEQ ID NO: 14) encodes a protein having 40.7% identity to the amino acid sequence of the *T. cutaneum* PAL/TAL enzyme. The protein is referred to as PcTAL herein.

Example 11

Cloning of DNA Fragment Encoding TAL from *P. chrysosporium*

Total RNA was prepared from 100 mL of *P. chrysosporium* cells (strain ME-446, obtained from the USDA Forest Products Laboratory) grown for 3 days in 15 g/L Difco Malt Extract Broth (Becton Dickinson Microbiology Systems, Sparks, Md.). supplemented with 2.0 mM tyrosine (added to induce PAL/TAL activities). Cells were harvested by centrifugation (3500 rpm, 5 min) in a Beckman CS-6R centrifuge with GH3.8 rotor (Beckman Coulter, Inc. Fullerton, Calif.), washed once with water, resuspended in 1.0 mL of Trizol reagent (Invitrogen, Carlsbad, Calif.), mixed with an equal volume of 0.5 mm glass beads, transferred to two 2.0 mL screw cap tubes and homogenized at maximum speed in a Biospec Mini beadbeater (Biospec Products, Bartlesville, Okla.) for three minutes. The homogenized cells were transferred to microfuge tubes and centrifuged at 14000 rpm in an Eppendorf centrifuge (Westbury, N.Y.). The supernatant was combined into one tube and allowed to sit for 5 minutes at room temperature. Chloroform/isoamylalcohol (0.2 mL, 25/1 mixture) was added and the tube shaken for 15 sec by hand. The solution was then incubated for 5 min at room temperature followed by centrifugation for 5 min at 14000 rpm at 4° C. The aqueous upper phase was transferred to a new tube and isopropanol (0.5 mL) was added. After 10 min at room temperature the solution was centrifuged at 14000 rpm for 5 min at 4° C., the supernatent was removed, and the RNA pellet allowed to air dry and then was dissolved in RNase free water (0.5 mL).

The total RNA sample was directly used for polyA(+)RNA isolation using the Qiagen oligoTex kit (Qiagen, Valencia, Calif.) following the manufacturer's protocol. Total RNA (0.5 mL) was mixed with 0.5 ml of buffer OBB from the kit. The Oligotex suspension (50 μL) was added, and the sample incubated at 72° C. for 5 minutes. It was then allowed to cool at room temperature for 10 min and the Oligotex:mRNA complex pelleted by centrifugation at 14000 rpm in a microfuge for 2 minutes after which the supernatant was removed, and the pellet resuspended in 400 μl of buffer OW2 from the kit. The resuspended sample was transferred into the kit's spin column and centrifuged at 14000 rpm for one minute, and washed one more time with 400 μl of buffer OW2 by resuspending the pellet and centrifugation. The mRNA was eluted by adding 25 μl of 75° C. buffer OEB from the kit followed by centrifugation for one minute. The elution step was repeated one more time. The total amount of mRNA obtained was 1.75 μg.

A first strand of cDNA was prepared from the mRNA sample using the Invitrogen 3'-RACE kit. The mRNA sample (50 ng in 11 μl) was mixed with AP primer (1.0 μl of 10 μM) from the kit, heated to 72° C. for 10 minutes followed by chilling on ice for 2 minutes. At this time 2.0 μl each of kit components, [10×PCR buffer, 25 mM $MgCl_2$, and 0.1 M DTT] and 1.0 μl of 10 mM dNTP was added and the mixture placed in a 42° C. air incubator for two minutes. To this solution, superscript II reverse transcriptase (1.0 μl) was added, and the mixture incubated at 42° C. for one h. The resulting first strand cDNA was directly used as a PCR template.

The following primers (SEQ ID NOs:26 and 27) were designed for amplification of the putative TAL encoding sequence from the cDNA of *P. chrysosporium*:

```
                                        (SEQ ID NOs: 26)
PCPAL-F:    GATCGAATTCATGCCGCCCCTTCAACAGAG

                                        (SEQ ID NOs: 27)
PCPAL-R:    GATCAAGCTTCTACGCCTTGATAGACTTGAC
```

The forward primer started at residue 33 of the putative ORF such that the codons for the first 11 amino acids were omitted. Because of the high GC content of the sequence, BD Bioscience Advantage GC-cDNA polymerase mix was used for amplification (Clontech, Mountain View, Calif.). The reaction mixture contained 1.0 μl of $1^{st}$ strand cDNA as template, 1.0 μl each of the 20 μM primers, 10 μl of 5.0 M G melt, 10 μl of 5×PCR buffer, 1.0 μl of 50× dNTP mix, 1.0 μl of Advantage GC cDNA polymerase mix, and 25 μl of water. The PCR conditions used were: 94° C. 1 min30 sec, followed by 30 cycles of 94° C. 30 sec and 68° C. 4 min. A final incubation at 68° C. for 7 minutes was added at the end. The PCR product was analyzed by agarose gel electrophoresis and a ~2.1 kb band was observed. The PCR product was then diluted 1:50, and 1.0 μl of the diluted product used as template for a second round of PCR, using TaKaRa ExTaq 2× premix and the same set of primers. The reaction volume was 50 μl and the PCR conditions were: 94° C. one min 30 sec, followed by 30 cycles of 94° C. 30 sec, 55° C. 30 sec and 72° C. two min, ending with 7 min at 72° C.

The PCR product from the second round was purified with a Qiagen PCR purification kit according to the manufacturer's protocol. The purified PCR product was digested with EcoRI and HindIII, and ligated with pBAD-HisB (Invitrogen) that was digested with the same enzymes. The EcoRI and HindIII sites in the pBAD-HisB vector are in the Multiple Cloning Site between an araB promoter and rrnB T1 and T2 terminators. The pBAD-HisB vector additionally contains a gene encoding the araC transcriptional activator, located upstream from the araB promoter, and an ampicillin resistance marker. The ligated DNA was used to transform *E. coli* Top10' competent cells (Invitrogen).

Seven colonies resulting from plating the transformed cells on LB+50 μg/mL Amp medium were chosen to inoculate 2.0 mL cultures of LB+Amp 50+0.2% arabinose, which were grown overnight at 37° C., and centrifuged at 14000 rpm for two min. Typically the pHCA product produced by the TAL enzyme intracellularly can diffuse across the cell membrane, therefore the presence of pHCA in culture supernatants is an indication that the TAL enzyme is expressed in an active form in the cells. The supernatants were analyzed by HPLC as described in the General Methods for the presence of pHCA and CA. Four samples contained significant amounts of both compounds, indicating the presence of PAL/TAL activity, as shown in Table 4. These results confirmed that the cloned DNA fragment encoded a TAL enzyme.

TABLE 4

The pHCA and CA levels in the supernatants of induced *P. chrysosporium* TAL expression clones.

| Sample | pHCA (ppm) | CA (ppm) |
|---|---|---|
| Clone 1 | 22 | 24 |
| Clone 2 | 1 | 1 |
| Clone 3 | 0 | 0 |
| Clone 4 | 48 | 93 |
| Clone 5 | 35 | 50 |
| Clone 6 | 28 | 36 |
| Clone 7 | 1 | 1 |

Example 12

Synthesis and Subcloning of Codon Optimized DNA Sequence Encoding PcTAL

Analysis of the sequence of the cloned PcTAL encoding DNA fragment showed that the codon usage was not optimal for expression in *E. coli*. An *E. coli* codon optimized PcTAL coding region fragment was designed and synthesized by DNA2.0 (Palo Alto, Calif.). EcoRI and HindIII sites were included at the 5' and 3' ends of the designed PcTAL coding sequence, respectively. The sequence of the codon optimized coding region is given in SEQ ID NO:15. A DNA fragment containing this sequence was cloned into the vector pJ2 (DNA2.0).

The DNA fragment containing the codon optimized PcTAL coding region was substituted for the fragment encoding RgTAL in pLH320, described in Example 1 herein, using EcoRI and HindIII restriction sites, to generate plasmid pLH344. Plasmid pLH344 was transformed into *E. coli* K12 strain BW25113, described in Example 1 herein, to generate strain DPD5154.

Example 13

Temperature Profiles and Thermostability of PcTAL Enzyme in DPD5154 Strain

Cells required for this Example were grown in a 10 liter Braun BiostatC fermentor with an initial volume post inoculation of 8 liters of medium containing: yeast extract (2 g/L), $CaCl_2.2H_2O$ (0.8 g/L), citric acid.$H_2O$ (1.9 g/L), $FeSO_4.7H_2O$ (0.2 g/L), $MgSO_4.7H_2O$ (1.1 g/L), $MnSO_4.H_2O$ (0.03 g/L), NaCl (0.01 g/L), $ZnSO_4.7H_2O$ (1.0 mg/L), $H_3BO_3$ (0.1 mg/L), $CuSO_4.5H_2O$ (0.1 mg/L), $NaMoO_4.2H_2O$ (0.1 mg/L), phosphoric acid, 85% (2.9 mL/L), sulfuric acid, 98% (0.5 mL/L), KOH, 50% (0.275 mL/L), and antifoam (0.5 mL/L). Prior to inoculation, glucose and spectinomycin were added to final concentrations of 5 g/L and 50 mg/L respectively. The inoculum was grown in a 2 L shake flask containing 500 mL of the following medium: $KH_2PO_4$ (2.0 g/L), $K_2HPO_4$ (13.0 g/L), $(NH_4)_2PO_4$ (4.0 g/L), $MgSO_4.7H_2O$ (1.0 g/L), yeast extract (2.0 g/L), ferric ammonium citrate (0.1 g/L), glucose (5.0 g/L) and spectinomycin (50 mg/L), with pH adjusted to 6.8. The shake flask was incubated at 36° C. and 300 rpm to an $OD_{550}$ of 3 and the entire contents used to inoculate the fermenter. The fermenter was controlled at 36° C., pH 6.8 (with $NH_4OH$, 40% (w/v)), airflow of 4.0 SLPM, pressure of 0.5 barg, and dissolved oxygen tension of 25%. A solution of glucose (50% (w/w)) was fed to the fermenter to maintain a specific growth rate of 0.2 g/g h. When the culture reached an $OD_{550}$ of 35, arabinose was added at a final concentration of 0.3 g/L and the glucose feed rate held at 0.85 g/min for 12 hours until harvest. The final cell density in the recovered broth was an $OD_{550}$ of 92 (30 g/L dry cell weight) and the final volume was 8.7 L. The cells were harvested by centrifugation forming a cell paste.

The TAL activity of the strain was measured in a cell-based assay at different temperatures. The fermentation cell paste was resuspended in water, and diluted to $OD_{600}$ of 3.0. Formation of pHCA was monitored in a 1.0 mL reaction in a UV grade disposable cuvette (VWR) for three minutes at λ 315 nm, 35° C. with 0.03 $OD_{600}$ of DPD5154 cells, in 100 mM CAPS, pH10 with 10 mM tyrosine. The pH value of the CAPS buffer was adjusted according to the corresponding assay temperature, which was varied from 25° C. to 60° C. The TAL activity was calculated using the following equation based on the assumption that 1.0 $OD_{600}$ of *E. coli* cells is equivalent to 0.33 g/L dry cell weight (dcw). The extinction coefficient of pHCA at pH 10 at 315 nm had previously been experimentally determined to be 16,800 $M^{-1}$ $cm^{-1}$. One unit of enzyme activity is defined as the formation of 1.0 μM of pHCA product per minute reaction.

$$\text{The total } TAL \text{ Activity}(\mu\text{M/min}) = \text{Initial Slope}(/\text{min}) \times [1{,}000{,}000\,(\mu\text{M/M})/16{,}800\ \text{M}^{-1}\text{cm}^{-1}] = \text{Slope}(/\text{min}) \times 59.52\,(\mu\text{M})$$

$$TAL \text{ Specific Activity(U/g DCW)} = \frac{\text{Total } TAL \text{ Activity}(\mu\text{M/min})}{\text{OD}_{600} \times 0.33 \text{ g dry cell/L}}$$

The whole cell TAL activity of strain DPD5154 increased significantly as the temperature was raised from 25° C. to 60° C. as show in FIG. 7. At 60° C. (467 U/g dcw) the activity was approximately six times that observed at 25° C. (70 U/g dcw). The maximum TAL activity was observed at 60° C. The temperature profile of strain DPD5124 (RgTAL) is also shown in FIG. 7. RgTAL has similar activity as PcTAL at 25° C. (63 U/g DCW), and its activity increases to 200 U/g DCW at 60° C., which is significantly less increase compared to PcTAL over the same temperature range. These results indicated that the PcTAL enzyme is a highly thermostable enzyme.

The stability of TAL activity of PcTAL and RgTAL against heat denaturation was analyzed by extended heat treatment at various temperatures. The crude extracts of DPD5154 (PcTAL) and DPD5124 (RgTAL) strains were generated as described above. After incubation at 70° C. or 80° C. for 20 min in 50 mM Tris-HCl, pH 8.0, the TAL activity of each enzyme was determined and calculated based on soluble proteins in the crude extracts. With DPD5124 extract, 97% of the TAL activity was lost after 20 min at 70° C.; while DPD5154 lost only 34% of its TAL activity under the same conditions. Both extracts lost most activity after 20 min at 80° C. These results shown in FIG. 8 confirmed the thermostability of PcTAL as compared to RgTAL.

The thermostability of the PcTAL enzyme was further characterized at 60° C. The crude extracts of DPD5154 (PcTAL) and DPD5124 (RgTAL) strains were incubated at 60° C. in 50 mM Tris-HCl, pH 8.0, and the TAL activities were measured as described previously at several time points up to 4 h. The DPD5154 extract maintained its full TAL activity for 3 h, and retained 72% activity after 4 h, while DPD5154 extract lost 50% of its TAL activity after one hour, and only 9% of the activity remained after 4 h. These results shown in FIG. 9 substantiate the thermostability of PcTAL at 60° C. and at pH 8 as compared to RgTAL.

Example 14

Preparation of GA/PEI Cross-Linked Alginate Beads with Strain DPD5154 Having Accumulated PcTAL This example illustrates the stability of the thermostable PcTAL bearing *E. coli* strain to GA/PEI cross-linking conditions to prepare calcium alginate beads.

Part A: Preparation of Alginate and *E. coli* Cell Suspensions.

Strain DPD5154 cells were grown and prepared as described in Example 8 for DPD5124 except that at the time of arabinose addition for the induction of TAL enzyme, the temperature was maintained at 36° C. The final OD in the fermenter was 92; the TAL activity in the DPD5154 cells was 151±10 Units per g dcw. Preweighed 118 g frozen cell paste was transferred into a large polyethylene bag that was sealed and kept at −70° C. until needed. On the morning of the bead preparation, the cells were transferred to the refrigerator to soften until use. A large magnetic stir bar and 165.75 mL of distilled deionized water were placed in a large wide-mouth jar. The vessel was transferred into a water bath atop a heater/stirrer. While the water solution was stirred briskly, alginate (9.1 g Protanal) was slowly added over a 14 minute period. During this period the temperature rose from ambient to 65° C. After the alginate was completely added (174.8 mL total volume, 5.24% alginate), the water bath was heated to 80° C. The suspension was mixed at the maximum rate possible and with vigorous hand mixing with a spatula until the alginate was completely dissolved. The solution was allowed to slowly cool to ambient temperature. Chunks of the 118 g of wet cell paste of *E. coli* strain DPD5154 (27% dry cell weight, dcw=31.8 g) were added to the cooled alginate solution. The thawing cell chunks were broken and blended with the alginate solution using a spatula when necessary. After all of the large chunks were added, the remaining cell paste was suspended in 40 mL distilled deionized water and transferred to the alginate/cell paste mixture. The alginate/cell paste mixture was homogenized (158 mL total volume, 15.16% dcw cell suspension) until a smooth slurry was achieved and the cells were fully suspended in the alginate solution. This mixture was kept at 25° C. until the bead-making step. Complete homogenization of the cell paste into the alginate solution took ~60 minutes.

Part B: Set-Up and Bead-Making.

Calcium acetate buffer (1.85 L, 0.2 M calcium acetate, pH 7.0) was prepared and poured into a large 2.5 L plastic beaker. A single bead making 18-gauge needle was set up with L/S 14 Masterflex® Tubing (Cole Parmer 06508-14) and circa 2.5 feet length feeding from the cell paste through a Masterflex® LSII Pump head. The needle was offset from the solution vortex with the left-most edge of the die about 1 inch away from the edge of the pail containing the hardening buffer. The distance between the end of the needles and the surface of the hardening buffer was set at 14.5 inches. The flow rate out of the #14 tubing was set for 2 mL/min. When about one-third of the cell/alginate suspension was consumed, the flow rate was reduced to 1.8 mL/min. Beads formed as the alginate/cell suspension contacted the buffer solution. The beads were stirred in the pail containing the calcium acetate hardening buffer at a rate sufficient to keep the beads suspended. The beads were allowed to harden in the 0.2 M calcium acetate, pH 7.0 solution for 2 hours.

Part C: Cross-Linking.

Using a large coarse glass-sintered filter, the hardened beads were filtered to acquire a crude wet yield of 261 g. The beads were resuspended in 637 mL decanted spent calcium acetate, pH 7.0 buffer. "Floating" beads (30 g) were removed. The following quantity of 12.5% PEI solution was added to the beads: 13 g (equal to 1 g per 20 g beads) to the 261 g beads. The reaction mixture was allowed to stir overnight for 16 h. GA solution (3.4 g of 25% (w/w) solution, this is a quantity of 0.25 g per 20 gram beads) was diluted with 16.6 g water for a final volume of ~20 mL solution. This solution was added drop-wise via a syringe at a rate of 0.3 mL/min over 90 minutes to the PEI-treated 261 g bead preparation. The jar was set on a magnetic stir plate and stirred gently until the GA addition was completed. The cross-linked bead solution was allowed to stir for another 30 minutes at ambient temperature before transfer to cold room for overnight stirring. The pink-tinted buffer was decanted from the beads. The pink-colored beads were washed 3 times for 15 minutes with 170 mL 5 mM calcium chloride solution. Beads were filtered and weighed to measure a yield of 260 g. The bead preparation was labeled T5154-A. The bead preparation was placed in a separate storage jar, suspended in 5 mM calcium chloride, capped and stored cold (5° C.) until use in large scale pHCA-producing reactions as described in Example 9. The bead preparation was assayed for tyrosine ammonia lyase activity by mixing 300 mg of bead catalyst in 25 mL volume of assay buffer (12.5 mM tyrosine, 50 mM CHES, pH 9.8 buffer, 10 mM calcium chloride, T=35° C.). Rates of pHCA formation were measured by HPLC analyses on aliquots removed at time intervals between 15 and 120 minutes. TAL activity in the beads was 4.3 g pHCA produced/L/h per g dcw *E. coli* DPD5154 in T5154-A.

Example 15

Production of Repeated pHCA Batches from 60 g/l Tyrosine at 45° c. Using Calcium Alginate Bead Immobilized DPD5154 Containing PcTAL (T5154-A)

The reaction vessel used was an Applikon Biotechnology (Foster City, Calif.) BioBundle™ glass autoclavable bioreactor system containing a 3 L fermentation vessel, ADI 1010 Controller, 10225 Cabinet, a fixed speed pump, pH/DO probes and a heating blanket. The run parameters were at the following settings: temperature, 45° C.; pH 9.7; agitation rate, 225 rpm; working volume, 1.5 L; TAL cell catalyst, 9.2 g dcw; gas outlet open. The reactor was charged with _0.9 L pre-warmed (45° C.)_10 mM calcium chloride solution and titrated to pH 9.7 using 50% w/w sodium hydroxide. Tyrosine (90 g tyrosine) was added as a slurry in 300 mL water and the residual tyrosine in the transfer vessel was rinsed with 160 mL water and added to the Applikon reactor. The pH control was turned on, and the reactor was set for operations at pH 9.7 using 25% w/w sodium hydroxide as the titrant. The reactant suspension was mixed for 15 minutes and equilibrated to the set temperature before addition of the TAL catalyst (96 g beads T5154-A prepared in Example 14) to initiate the reaction. The initial working volume of the reactor was 1.5 L. Aliquots (circa 1-2.5 mL) were removed by a 5 mL serological pipet through the sample port at run times of 3 min, 30 min, 60 min, 90 min, 120 min and end-of-run (circa 12 h). The aliquots were centrifuge-filtered and diluted for HPLC analyses to quantify pHCA production and soluble tyrosine in the reactor. The reactor was terminated and turned over for another cycle by shutting down temperature and pH control. The clear supernatant was transferred out of the reactor by removed by pipetting. The beads were not washed between cycles. Every step, except for loading of beads, was repeated in the same order as described for the first cycle. This process was repeated three times for a total of four reaction cycles. After the first cycle, half of the beads were removed so that for cycles 2 through 4 only 48 g beads (4.6 g dcw) was present as catalyst. The reactor was terminated due to exceedingly long reaction cycle times for cycle four; however, after four cycles, a cumulative catalyst productivity index (CPI; g pHCA produced per g dcw DPD5154 TAL cell calcium alginate bead catalyst) of ca 37 was achieved (FIG. 10). Due to a combination of its higher activity and operation at a higher temperature, the T5154-A bead catalyst was able to reach a CPI that took eleven cycles for the T5124-D bead catalyst.

What is claimed is:

1. An immobilized tyrosine ammonia lyase biocatalyst comprising:

a) a bacterial cell tolerant to para-hydroxycinnamic acid and alkaline pH and transformed with a genetic construct comprising a gene, the gene encoding a tyrosine ammonia lyase (TAL) enzyme selected from the group of TAL enzymes having TAL enzyme activity from *Rhodotorula glutinis, Phanerochaete chrysosporium, Trichosporon cutaneum, Rhodobacter sphaeroides* and mutagenized *Rhodosporidium toruloides*; and b) a cross-linked alginate bead prepared by a process in which glutaraldehyde is used at a final concentration of between about $2.5\times10^{-4}$ g and about $6.3\times10^{-3}$ g glutaraldehyde per gram of bead;

wherein the bacterial cell is embedded in the alginate bead; and wherein the tyrosine ammonia lyase enzyme has an activity about 1.9 to about 8.0 measured as g pHCA produced/L/h per g dcw bead catalyst.

2. The immobilized tyrosine ammonia lyase biocatalyst of claim 1 wherein the cross-linked alginate bead is crosslinked with glutaraldehyde and polyethylenimine.

3. The immobilized tyrosine ammonia lyase biocatalyst of claim 2 wherein the alginate bead is crosslinked by a process where glutaraldehyde is added at a rate that is less than about $1\times10^{-4}$ g glutaraldehyde/g beads per minute, and wherein glutaraldehyde and polyethylenimine are added in either order.

4. The immobilized tyrosine ammonia lyase biocatalyst of claim 1 wherein the bacterial host cell is a strain of *E. coli.*

5. The immobilized tyrosine ammonia lyase biocatalyst of claim 4 wherein the *E. coli* strain is an *E. coli* K12 strain selected from the group consisting of RFM443, W3110 and BW25113.

6. The immobilized tyrosine ammonia lyase biocatalyst of claim 1 wherein the bacterial cell is in the form of whole or permeabilized bacterial cells.

7. The immobilized tyrosine ammonia lyase biocatalyst of claim 1 wherein the cross-linked alginate bead comprises calcium alginate.

8. A method for producing para-hydroxycinnamic acid comprising:

a) providing an tyrosine ammonia lyase biocatalyst according to claim 1;

b) providing a source of tyrosine;

c) contacting the biocatalyst or (a) with the tyrosine of (b) a suitable aqueous reaction mixture whereby p-hydroxycinnamic acid is produced;

d) recovering the p-hydroxycinnamic acid; and e) optionally repeating c) and d) at least one time.

9. The method of claim 8 wherein the source of tyrosine is a bacterial host that is overproducing for tyrosine.

10. The method of claim 8 wherein the contacting step (c) is a pH of about 8.0 to about 11.0.

11. The method of claim 10 wherein the pH is from about 9.5 to about 9.9.

12. The method of claim 8 wherein the aqueous reaction mixture comprises calcium at a concentration between about 5 mM and about 20 mM.

* * * * *

```
SEQUENCE LISTING

<160> NUMBER OF SEQ ID NOS: 29

<210> SEQ ID NO 1
<211> LENGTH: 716
<212> TYPE: PRT
<213> ORGANISM: Rhodotorula glutinis

<400> SEQUENCE: 1

Met Ala Pro Ser Leu Asp Ser Ile Ser His Ser Phe Ala Asn Gly Val
1               5                   10                  15

Ala Ser Ala Lys Gln Ala Val Asn Gly Ala Ser Thr Asn Leu Ala Val
            20                  25                  30

Ala Gly Ser His Leu Pro Thr Thr Gln Val Thr Gln Val Asp Ile Val
        35                  40                  45

Glu Lys Met Leu Ala Ala Pro Thr Asp Ser Thr Leu Glu Leu Asp Gly
    50                  55                  60

Tyr Ser Leu Asn Leu Gly Asp Val Val Ser Ala Ala Arg Lys Gly Arg
65                  70                  75                  80

Pro Val Arg Val Lys Asp Ser Asp Glu Ile Arg Ser Lys Ile Asp Lys
                85                  90                  95

Ser Val Glu Phe Leu Arg Ser Gln Leu Ser Met Ser Val Tyr Gly Val
            100                 105                 110

Thr Thr Gly Phe Gly Gly Ser Ala Asp Thr Arg Thr Glu Asp Ala Ile
        115                 120                 125

Ser Leu Gln Lys Ala Leu Leu Glu His Gln Leu Cys Gly Val Leu Pro
    130                 135                 140

Ser Ser Phe Asp Ser Phe Arg Leu Gly Arg Gly Leu Glu Asn Ser Leu
145                 150                 155                 160

Pro Leu Glu Val Val Arg Gly Ala Met Thr Ile Arg Val Asn Ser Leu
                165                 170                 175

Thr Arg Gly His Ser Ala Val Arg Leu Val Val Leu Glu Ala Leu Thr
            180                 185                 190

Asn Phe Leu Asn His Gly Ile Thr Pro Ile Val Pro Leu Arg Gly Thr
        195                 200                 205

Ile Ser Ala Ser Gly Asp Leu Ser Pro Leu Ser Tyr Ile Ala Ala Ala
    210                 215                 220

Ile Ser Gly His Pro Asp Ser Lys Val His Val Val His Glu Gly Lys
225                 230                 235                 240

Glu Lys Ile Leu Tyr Ala Arg Glu Ala Met Ala Leu Phe Asn Leu Glu
                245                 250                 255

Pro Val Val Leu Gly Pro Lys Glu Gly Leu Gly Leu Val Asn Gly Thr
            260                 265                 270

Ala Val Ser Ala Ser Met Ala Thr Leu Ala Leu His Asp Ala His Met
        275                 280                 285

Leu Ser Leu Leu Ser Gln Ser Leu Thr Ala Met Thr Val Glu Ala Met
    290                 295                 300

Val Gly His Ala Gly Ser Phe His Pro Phe Leu His Asp Val Thr Arg
```

```
305                 310                 315                 320

Pro His Pro Thr Gln Ile Glu Val Ala Gly Asn Ile Arg Lys Leu Leu
                325                 330                 335

Glu Gly Ser Arg Phe Ala Val His His Glu Glu Glu Val Lys Val Lys
            340                 345                 350

Asp Asp Glu Gly Ile Leu Arg Gln Asp Arg Tyr Pro Leu Arg Thr Ser
        355                 360                 365

Pro Gln Trp Leu Gly Pro Leu Val Ser Asp Leu Ile His Ala His Ala
    370                 375                 380

Val Leu Thr Ile Glu Ala Gly Gln Ser Thr Thr Asp Asn Pro Leu Ile
385                 390                 395                 400

Asp Val Glu Asn Lys Thr Ser His His Gly Gly Asn Phe Gln Ala Ala
                405                 410                 415

Ala Val Ala Asn Thr Met Glu Lys Thr Arg Leu Gly Leu Ala Gln Ile
            420                 425                 430

Gly Lys Leu Asn Phe Thr Gln Leu Thr Glu Met Leu Asn Ala Gly Met
        435                 440                 445

Asn Arg Gly Leu Pro Ser Cys Leu Ala Ala Glu Asp Pro Ser Leu Ser
    450                 455                 460

Tyr His Cys Lys Gly Leu Asp Ile Ala Ala Ala Ala Tyr Thr Ser Glu
465                 470                 475                 480

Leu Gly His Leu Ala Asn Pro Val Thr Thr His Val Gln Pro Ala Glu
                485                 490                 495

Met Ala Asn Gln Ala Val Asn Ser Leu Ala Leu Ile Ser Ala Arg Arg
            500                 505                 510

Thr Thr Glu Ser Asn Asp Val Leu Ser Leu Leu Leu Ala Thr His Leu
        515                 520                 525

Tyr Cys Val Leu Gln Ala Ile Asp Leu Arg Ala Ile Glu Phe Glu Phe
    530                 535                 540

Lys Lys Gln Phe Gly Pro Ala Ile Val Ser Leu Ile Asp Gln His Phe
545                 550                 555                 560

Gly Ser Ala Met Thr Gly Ser Asn Leu Arg Asp Glu Leu Val Glu Lys
                565                 570                 575

Val Asn Lys Thr Leu Ala Lys Arg Leu Glu Gln Thr Asn Ser Tyr Asp
            580                 585                 590

Leu Val Pro Arg Trp His Asp Ala Phe Ser Phe Ala Ala Gly Thr Val
        595                 600                 605

Val Glu Val Leu Ser Ser Thr Ser Leu Ser Leu Ala Ala Val Asn Ala
    610                 615                 620

Trp Lys Val Ala Ala Ala Glu Ser Ala Ile Ser Leu Thr Arg Gln Val
625                 630                 635                 640

Arg Glu Thr Phe Trp Ser Ala Ala Ser Thr Ser Ser Pro Ala Leu Ser
                645                 650                 655

Tyr Leu Ser Pro Arg Thr Gln Ile Leu Tyr Ala Phe Val Arg Glu Glu
            660                 665                 670

Leu Gly Val Lys Ala Arg Arg Gly Asp Val Phe Leu Gly Lys Gln Glu
        675                 680                 685

Val Thr Ile Gly Ser Asn Val Ser Lys Ile Tyr Glu Ala Ile Lys Ser
    690                 695                 700

Gly Arg Ile Asn Asn Val Leu Leu Lys Met Leu Ala
705                 710                 715
```

<210> SEQ ID NO 2
<211> LENGTH: 737

<212> TYPE: PRT
<213> ORGANISM: Phanerochaete chrysosporium

<400> SEQUENCE: 2

```
Met Pro Ser Arg Ile Asp Tyr Tyr Thr Ser Ser Gly Asn Gly Tyr Ala
1               5                   10                  15

Gln Ser Arg Lys Ser Ser Ala Ile Tyr Pro Ala Ser Ala Ser Thr Gly
            20                  25                  30

His Ala Ala Pro Ser Thr Glu Arg Lys Pro Glu Leu Leu Asp Lys Phe
        35                  40                  45

Val Glu Ala Tyr Asp Glu Leu Gln Ser Tyr Arg Glu Gly Lys Pro Val
    50                  55                  60

Ile Val Asp Gly His Asn Leu Ser Ile Pro Ala Val Ala Ala Thr Ala
65                  70                  75                  80

Arg Phe Gly Ala Ala Val Val Leu Asp Glu Asn Pro Glu Thr His Glu
                85                  90                  95

Arg Val Leu Gln Ser Arg Arg Val Ile Val Asp Lys Val Ser Thr Gln
            100                 105                 110

Arg Ser Val Tyr Gly Val Ser Thr Gly Phe Gly Gly Ser Ala Asp Thr
        115                 120                 125

Arg Thr Ser Asp Pro Leu Gln Leu Gly His Ala Leu Leu Gln His Gln
    130                 135                 140

His Val Gly Val Leu Pro Thr Gln Thr Glu Ser Pro Leu Pro Ala Leu
145                 150                 155                 160

Pro Leu Gly Asp Pro Leu Ala Thr Thr Ser Met Pro Glu Ala Trp Val
                165                 170                 175

Arg Gly Ala Ile Leu Ile Arg Met Asn Ser Leu Ile Arg Gly His Ser
            180                 185                 190

Gly Val Arg Trp Glu Leu Ile Glu Lys Met Gly Glu Leu Leu Arg Glu
        195                 200                 205

Asn Ile Thr Pro Leu Val Pro Leu Arg Gly Ser Ile Ser Ala Ser Gly
    210                 215                 220

Asp Leu Ser Pro Leu Ser Tyr Ile Ala Gly Thr Leu Ile Gly Ser Pro
225                 230                 235                 240

Ala Ile Arg Val Phe Asp Gly Pro Ala Ser Tyr Gly Ala Arg Arg Ile
                245                 250                 255

Leu Pro Ser Asn Ile Ala Leu Ala Asn His Gly Val Ala Pro Ile Pro
            260                 265                 270

Leu Ser Ser Lys Glu His Leu Gly Ile Leu Asn Gly Thr Ala Phe Ser
        275                 280                 285

Ala Ser Val Gly Ala Leu Ala Leu Asn Glu Ala Val His Leu Ser Leu
    290                 295                 300

Leu Ala Gln Val Cys Thr Ala Met Gly Thr Glu Ala Met Ile Gly Ala
305                 310                 315                 320

Val Gly Ser Phe Asp Ala Phe Ile His Asp Thr Ala Arg Pro His Pro
                325                 330                 335

Gly Gln Val Glu Val Ala Arg Asn Val Arg Thr Leu Leu Glu Asp Ser
            340                 345                 350

Gln Met Ala Val Lys Ala Glu Asp Glu Val His Ile Ala Glu Asp Glu
        355                 360                 365

Gly Glu Leu Arg Gln Asp Arg Tyr Pro Leu Arg Thr Ala Ala Gln Phe
    370                 375                 380

Leu Gly Pro Gln Ile Glu Asp Ile Leu Ser Ala His Glu Thr Val Thr
385                 390                 395                 400
```

```
Leu Glu Cys Asn Ser Thr Thr Asp Asn Pro Leu Ile Asp Gly Glu Thr
                405                 410                 415

Gly Thr Val His His Gly Gly Asn Phe Gln Ala Met Ala Val Thr Asn
            420                 425                 430

Ala Met Glu Lys Thr Arg Leu Ala Ile His His Ile Gly Lys Leu Leu
        435                 440                 445

Phe Ala Gln Ala Thr Glu Leu Ile Asn Pro Met Met Asn Arg Gly Leu
    450                 455                 460

Pro Pro Asn Leu Ala Ala Thr Asp Pro Ser His Asn Tyr Phe Ala Lys
465                 470                 475                 480

Gly Val Asp Ile His Leu Ala Ala Tyr Val Gly Glu Leu Gly Phe Leu
                485                 490                 495

Ala Ser Pro Val Ser Ser His Ile Gln Ser Ala Glu Met His Asn Gln
            500                 505                 510

Ala Val Asn Ser Leu Ala Leu Val Ser Ala Arg Tyr Thr Ile Ser Ala
        515                 520                 525

Leu Asp Val Leu Ser Leu Leu Thr Ala Ala Tyr Leu Tyr Val Leu Cys
    530                 535                 540

Gln Ala Leu Asp Leu Arg Ala Met His Asn Asp Leu Gln Ser Ser Leu
545                 550                 555                 560

Ser Ala Ile Val Arg Glu Leu Leu Pro Lys His Phe Pro Ser Ala Ala
                565                 570                 575

Lys Arg Ala Asp Ala Leu Leu Pro Ile Leu Glu Arg Thr Ile Phe Arg
            580                 585                 590

Ala Leu Asn Ser Ser Ser Ser Ala Asp Cys Lys Ala Arg Met Val Ser
        595                 600                 605

Val Ala Ala Ser Thr Thr Thr Pro Leu Val Asp Phe Leu Ser Ala Asp
    610                 615                 620

Ala Ala Leu Ala Ser Glu Leu Ala Asn Ile Thr Ala Phe Arg Thr Glu
625                 630                 635                 640

Leu Ala Thr Arg Ala Ala Asp Ala Leu Thr Thr Leu Arg Thr Gln Tyr
                645                 650                 655

Leu Glu Gly Ala Arg Gly Ala Ala Pro Ala Ser Lys Tyr Leu Gly Lys
            660                 665                 670

Thr Arg Pro Val Tyr Glu Phe Val Arg Val Thr Leu Asn Val Pro Met
        675                 680                 685

His Gly Arg Glu Asn Leu His Asn Phe Glu Met Gly Pro Gly Val Glu
    690                 695                 700

Asp Gly Ile Ile Gly Asn Asn Ile Ser Thr Ile Tyr Glu Ala Ile Arg
705                 710                 715                 720

Asp Gly Lys Met Gln Asn Val Val Met Gln Leu Val Lys Ser Ile Lys
                725                 730                 735

Ala


<210> SEQ ID NO 3
<211> LENGTH: 689
<212> TYPE: PRT
<213> ORGANISM: Trichosporon cutaneum

<400> SEQUENCE: 3

Met Phe Ile Glu Thr Asn Val Ala Lys Pro Ala Ser Thr Lys Ala Met
1               5                   10                  15

Asn Ala Gly Ser Ala Lys Ala Ala Pro Val Glu Pro Phe Ala Thr Tyr
            20                  25                  30

Ala His Ser Gln Ala Thr Lys Thr Val Ser Ile Asp Gly His Thr Met
```

```
        35                  40                  45

Lys Val Gly Asp Val Val Ala Val Ala Arg His Gly Ala Lys Val Glu
    50                  55                  60

Leu Ala Ala Ser Val Ala Gly Pro Val Arg Ala Ser Val Asp Phe Lys
65                  70                  75                  80

Glu Ser Lys Lys His Thr Ser Ile Tyr Gly Val Thr Thr Gly Phe Gly
                85                  90                  95

Gly Ser Ala Asp Thr Arg Thr Ser Asp Thr Glu Ala Leu Gln Ile Ser
            100                 105                 110

Leu Leu Glu His Gln Leu Cys Gly Phe Leu Pro Thr Asp Ala Thr Tyr
        115                 120                 125

Glu Gly Met Leu Leu Ala Ala Met Pro Ile Pro Ile Val Arg Gly Ala
    130                 135                 140

Met Ala Val Arg Val Asn Ser Cys Val Arg Gly His Ser Gly Val Arg
145                 150                 155                 160

Leu Glu Val Leu Gln Ser Phe Ala Asp Phe Ile Asn Arg Gly Leu Val
                165                 170                 175

Pro Cys Val Pro Leu Arg Gly Thr Ile Ser Ala Ser Gly Asp Leu Ser
            180                 185                 190

Pro Leu Ser Tyr Ile Ala Gly Ala Ile Cys Gly His Pro Asp Val Lys
        195                 200                 205

Val Phe Asp Thr Ala Ala Ser Pro Pro Thr Val Leu Thr Ser Pro Glu
    210                 215                 220

Ala Ile Ala Lys Tyr Gly Leu Lys Thr Val Lys Leu Ala Ser Lys Glu
225                 230                 235                 240

Gly Leu Gly Leu Val Asn Gly Thr Ala Val Ser Ala Ala Ala Gly Ala
                245                 250                 255

Leu Ala Leu Tyr Asp Ala Glu Cys Leu Ala Ile Met Ser Gln Thr Asn
            260                 265                 270

Thr Val Leu Thr Val Glu Ala Leu Asp Gly His Val Gly Ser Phe Ala
        275                 280                 285

Pro Phe Ile Gln Glu Ile Arg Pro His Ala Gly Gln Ile Glu Ala Ala
    290                 295                 300

Arg Asn Ile Arg His Met Leu Gly Gly Ser Lys Leu Ala Val His Glu
305                 310                 315                 320

Glu Ser Glu Leu Leu Ala Asp Gln Asp Ala Gly Ile Leu Arg Gln Asp
                325                 330                 335

Arg Tyr Ala Leu Arg Thr Ser Ala Gln Trp Ile Gly Pro Gln Leu Glu
            340                 345                 350

Ala Leu Gly Leu Ala Arg Gln Gln Ile Glu Thr Glu Leu Asn Ser Thr
        355                 360                 365

Thr Asp Asn Pro Leu Ile Asp Val Glu Gly Gly Met Phe His His Gly
    370                 375                 380

Gly Asn Phe Gln Ala Met Ala Val Thr Ser Ala Met Asp Ser Ala Arg
385                 390                 395                 400

Ile Val Leu Gln Asn Leu Gly Lys Leu Ser Phe Ala Gln Val Thr Glu
                405                 410                 415

Leu Ile Asn Cys Glu Met Asn His Gly Leu Pro Ser Asn Leu Ala Gly
            420                 425                 430

Ser Glu Pro Ser Thr Asn Tyr His Cys Lys Gly Leu Asp Ile His Cys
        435                 440                 445

Gly Ala Tyr Cys Ala Glu Leu Gly Phe Leu Ala Asn Pro Met Ser Asn
    450                 455                 460
```

```
His Val Gln Ser Thr Glu Met His Asn Gln Ser Val Asn Ser Met Ala
465                 470                 475                 480

Phe Ala Ser Ala Arg Arg Thr Met Glu Ala Asn Glu Val Leu Ser Leu
                485                 490                 495

Leu Leu Gly Ser Gln Met Tyr Cys Ala Thr Gln Ala Leu Asp Leu Arg
            500                 505                 510

Val Met Glu Val Lys Phe Lys Met Ala Ile Val Lys Leu Leu Asn Glu
        515                 520                 525

Thr Leu Thr Lys His Phe Ala Ala Phe Leu Thr Pro Glu Gln Leu Ala
    530                 535                 540

Lys Leu Asn Thr His Ala Ala Ile Thr Leu Tyr Lys Arg Leu Asn Gln
545                 550                 555                 560

Thr Pro Ser Trp Asp Ser Ala Pro Arg Phe Glu Asp Ala Ala Lys His
                565                 570                 575

Leu Val Gly Val Ile Met Asp Ala Leu Met Val Asn Asp Asp Ile Thr
            580                 585                 590

Asp Leu Thr Asn Leu Pro Lys Trp Lys Lys Glu Phe Ala Lys Glu Ala
        595                 600                 605

Gly Asn Leu Tyr Arg Ser Ile Leu Val Ala Thr Thr Ala Asp Gly Arg
    610                 615                 620

Asn Asp Leu Glu Pro Ala Glu Tyr Leu Gly Gln Thr Arg Ala Val Tyr
625                 630                 635                 640

Glu Ala Val Arg Ser Glu Leu Gly Val Lys Val Arg Arg Gly Asp Val
                645                 650                 655

Ala Glu Gly Lys Ser Gly Lys Ser Ile Gly Ser Ser Val Ala Lys Ile
            660                 665                 670

Val Glu Ala Met Arg Asp Gly Arg Leu Met Gly Ala Val Gly Lys Met
        675                 680                 685

Phe


<210> SEQ ID NO 4
<211> LENGTH: 526
<212> TYPE: PRT
<213> ORGANISM: Rhodobacter sphaeroides

<400> SEQUENCE: 4

Val Lys Pro Met Leu Ala Met Ser Pro Pro Lys Pro Ala Val Glu Leu
1               5                   10                  15

Asp Arg His Ile Asp Leu Asp Gln Ala His Ala Val Ala Ser Gly Gly
            20                  25                  30

Ala Arg Ile Val Leu Ala Pro Pro Ala Arg Asp Arg Cys Arg Ala Ser
        35                  40                  45

Glu Ala Arg Leu Gly Ala Val Ile Arg Glu Ala Arg His Val Tyr Gly
    50                  55                  60

Leu Thr Thr Gly Phe Gly Pro Leu Ala Asn Arg Leu Ile Ser Gly Glu
65                  70                  75                  80

Asn Val Arg Thr Leu Gln Ala Asn Leu Val His His Leu Ala Ser Gly
                85                  90                  95

Val Gly Pro Val Leu Asp Trp Thr Thr Ala Arg Ala Met Val Leu Ala
            100                 105                 110

Arg Leu Val Ser Ile Ala Gln Gly Ala Ser Gly Ala Ser Glu Gly Thr
        115                 120                 125

Ile Ala Arg Leu Ile Asp Leu Leu Asn Ser Glu Leu Ala Pro Ala Val
    130                 135                 140

Pro Ser Arg Gly Thr Val Gly Ala Ser Gly Asp Leu Thr Pro Leu Ala
```

```
145                 150                 155                 160

His Met Val Leu Cys Leu Gln Gly Arg Gly Asp Phe Leu Asp Arg Asp
                165                 170                 175

Gly Thr Arg Leu Asp Gly Ala Glu Gly Leu Arg Arg Gly Arg Leu Gln
            180                 185                 190

Pro Leu Asp Leu Ser His Arg Asp Ala Leu Ala Leu Val Asn Gly Thr
        195                 200                 205

Ser Ala Met Thr Gly Ile Ala Leu Val Asn Ala His Ala Cys Arg His
    210                 215                 220

Leu Gly Asn Trp Ala Val Ala Leu Thr Ala Leu Leu Ala Glu Cys Leu
225                 230                 235                 240

Arg Gly Arg Thr Glu Ala Trp Ala Ala Ala Leu Ser Asp Leu Arg Pro
                245                 250                 255

His Pro Gly Gln Lys Asp Ala Ala Ala Arg Leu Arg Ala Arg Val Asp
            260                 265                 270

Gly Ser Ala Arg Val Val Arg His Val Ile Ala Glu Arg Arg Leu Asp
        275                 280                 285

Ala Gly Asp Ile Gly Thr Glu Pro Glu Ala Gly Gln Asp Ala Tyr Ser
    290                 295                 300

Leu Arg Cys Ala Pro Gln Val Leu Gly Ala Gly Phe Asp Thr Leu Ala
305                 310                 315                 320

Trp His Asp Arg Val Leu Thr Ile Glu Leu Asn Ala Val Thr Asp Asn
                325                 330                 335

Pro Val Phe Pro Pro Asp Gly Ser Val Pro Ala Leu His Gly Gly Asn
            340                 345                 350

Phe Met Gly Gln His Val Ala Leu Thr Ser Asp Ala Leu Ala Thr Ala
        355                 360                 365

Val Thr Val Leu Ala Gly Leu Ala Glu Arg Gln Ile Ala Arg Leu Thr
    370                 375                 380

Asp Glu Arg Leu Asn Arg Gly Leu Pro Pro Phe Leu His Arg Gly Pro
385                 390                 395                 400

Ala Gly Leu Asn Ser Gly Phe Met Gly Ala Gln Val Thr Ala Thr Ala
                405                 410                 415

Leu Leu Ala Glu Met Arg Ala Thr Gly Pro Ala Ser Ile His Ser Ile
            420                 425                 430

Ser Thr Asn Ala Ala Asn Gln Asp Val Val Ser Leu Gly Thr Ile Ala
        435                 440                 445

Ala Arg Leu Cys Arg Glu Lys Ile Asp Arg Trp Ala Glu Ile Leu Ala
    450                 455                 460

Ile Leu Ala Leu Cys Leu Ala Gln Ala Ala Glu Leu Arg Cys Gly Ser
465                 470                 475                 480

Gly Leu Asp Gly Val Ser Pro Ala Gly Lys Lys Leu Val Gln Ala Leu
                485                 490                 495

Arg Glu Gln Phe Pro Pro Leu Glu Thr Asp Arg Pro Leu Gly Gln Glu
            500                 505                 510

Ile Ala Ala Leu Ala Thr His Leu Leu Gln Gln Ser Pro Val
        515                 520                 525
```

<210> SEQ ID NO 5
<211> LENGTH: 724
<212> TYPE: PRT
<213> ORGANISM: Ustilago maydis

<400> SEQUENCE: 5

```
Met Ala Pro Thr Ala Asp Val Leu Pro Pro Val Glu Ala Ser Thr Arg
```

-continued

```
1               5                   10                  15

Pro Gly Leu Leu Val Gln Pro Ser Asp Thr Lys Leu Arg Lys Ala Ser
            20                  25                  30

Ser Phe Arg Thr Glu Gln Val Val Ile Asp Gly Tyr Asn Leu Lys Ile
        35                  40                  45

Gln Gly Leu Val Ala Ser Ala Arg Tyr Gly His Val Thr Arg Pro Arg
    50                  55                  60

Pro Ser Ala Glu Thr Arg Lys Arg Ile Asp Asp Ser Val Gln Ser Leu
65                  70                  75                  80

Ile Ala Lys Leu Asp Gly Gly Glu Ser Ile Tyr Gly Ile Asn Thr Gly
                85                  90                  95

Phe Gly Gly Ser Ala Asp Ser Arg Thr Ala Asn Thr Arg Ala Leu Gln
            100                 105                 110

Leu Ala Leu Leu Gln Met Gln Gln Cys Gly Val Leu Pro Val Pro Ser
        115                 120                 125

Thr Phe Pro Thr Gly Glu Pro Ser Ser Ala Pro Phe Ala Leu Pro Leu
    130                 135                 140

Thr Asp Thr Glu Ser Ser Leu Ile Met Pro Glu Ala Trp Val Arg Gly
145                 150                 155                 160

Ala Ile Val Val Arg Leu Ser Ser Leu Met Arg Gly His Ser Gly Val
                165                 170                 175

Arg Trp Glu Val Leu Asp Lys Met Gln Lys Leu Phe Leu Gln Asn Asn
            180                 185                 190

Val Thr Pro Val Val Pro Val Arg Ser Ser Ile Ser Ala Ser Gly Asp
        195                 200                 205

Leu Ser Pro Leu Ser Tyr Val Ala Gly Ala Leu Ala Gly Gln Arg Gly
    210                 215                 220

Ile Tyr Cys Phe Val Thr Asp Gly Arg Gly Gln Arg Val Lys Val Thr
225                 230                 235                 240

Ala Asp Glu Ala Cys Arg Met His Lys Ile Thr Pro Val Gln Tyr Glu
                245                 250                 255

Pro Lys Glu Ala Leu Gly Leu Leu Asn Gly Thr Ala Phe Ser Ala Ser
            260                 265                 270

Val Ala Gly Leu Ala Thr Tyr Glu Ala Glu Asn Leu Ala Ser Leu Thr
        275                 280                 285

Gln Leu Thr Thr Ala Met Ala Val Glu Ala Leu Lys Gly Thr Asp Ala
    290                 295                 300

Ser Phe Ala Pro Phe Ile His Glu Ile Ala Arg Pro His Pro Gly Gln
305                 310                 315                 320

Ile Lys Ser Ala Lys Phe Ile Arg Ala His Leu Ser Gly Ser Arg Leu
                325                 330                 335

Ala Glu His Leu Glu Asn Glu Lys His Val Leu Phe Ser Glu Asp Asn
            340                 345                 350

Gly Thr Leu Arg Gln Asp Arg Tyr Thr Leu Gln Thr Ala Ser Gln Trp
        355                 360                 365

Val Gly Pro Gly Leu Glu Asp Ile Glu Asn Ala Lys Arg Ser Val Asp
    370                 375                 380

Phe Glu Ile Asn Ser Thr Thr Asp Asn Pro Met Ile Asp Pro Tyr Asp
385                 390                 395                 400

Gly Asp Gly Arg Ile His His Gly Gly Asn Phe Gln Ala Met Ala Met
                405                 410                 415

Thr Asn Ala Val Glu Lys Ile Arg Leu Ala Leu Cys Ala Met Gly Lys
            420                 425                 430
```

```
Met Thr Phe Gln Gln Met Thr Glu Leu Val Asn Pro Ala Met Asn Arg
        435                 440                 445

Gly Leu Pro Ala Asn Leu Ala Ser Thr Pro Asp Leu Ser Leu Asn Phe
    450                 455                 460

His Ala Lys Gly Ile Asn Ile Ala Leu Ala Ser Val Thr Ser Glu Leu
465                 470                 475                 480

Met Phe Leu Gly Asn Pro Val Ser Thr His Val Gln Ser Ala Glu Met
                485                 490                 495

Ala Asn Gln Ala Phe Asn Ser Leu Ala Leu Ile Ser Gly Arg Gln Thr
            500                 505                 510

Leu Gln Ala Ile Glu Cys Leu Ser Met Ile Gln Ala Trp Ser Leu Tyr
        515                 520                 525

Leu Leu Cys Gln Ala Leu Asp Ile Arg Ala Leu Gln Tyr Lys Val Ala
    530                 535                 540

Glu Gln Leu Pro Thr Leu Ile Leu Ala Ser Leu His Ser His Phe Gly
545                 550                 555                 560

Glu Trp Met Asp Glu Thr Lys Gln Gln Glu Ile Ala Ala Gln Val Leu
                565                 570                 575

Lys Ser Met Ser Lys Arg Leu Asp Glu Thr Ser Ser Lys Asp Leu Arg
            580                 585                 590

Asp Arg Leu Val Glu Thr Tyr Gln Asp Ala Ser Ser Val Leu Val Arg
        595                 600                 605

Tyr Phe Ser Glu Leu Pro Ser Gly Gly Gly Ala Asp Pro Leu Arg Asn
    610                 615                 620

Ile Val Lys Trp Arg Ala Thr Gly Val Ala Asp Thr Glu Lys Ile Tyr
625                 630                 635                 640

Arg Gln Val Thr Ile Glu Phe Leu Asp Asn Pro Tyr Ala Cys His Ala
                645                 650                 655

Ser His Leu Leu Gly Lys Thr Lys Arg Ala Tyr Glu Phe Val Arg Lys
            660                 665                 670

Thr Leu Gly Val Pro Met His Gly Lys Glu Asn Leu Asn Glu Phe Lys
        675                 680                 685

Gly Glu Phe Glu Gln Trp Asn Thr Thr Gly Gly Tyr Val Ser Val Ile
    690                 695                 700

Tyr Ala Ser Ile Arg Asp Gly Glu Leu Tyr Asn Met Leu Ser Glu Leu
705                 710                 715                 720

Glu Arg Asp Leu


<210> SEQ ID NO 6
<211> LENGTH: 716
<212> TYPE: PRT
<213> ORGANISM: Petroselinum crispum

<400> SEQUENCE: 6

Met Glu Asn Gly Asn Gly Ala Thr Thr Asn Gly His Val Asn Gly Asn
1               5                   10                  15

Gly Met Asp Phe Cys Met Lys Thr Glu Asp Pro Leu Tyr Trp Gly Ile
            20                  25                  30

Ala Ala Glu Ala Met Thr Gly Ser His Leu Asp Glu Val Lys Lys Met
        35                  40                  45

Val Ala Glu Tyr Arg Lys Pro Val Val Lys Leu Gly Gly Glu Thr Leu
    50                  55                  60

Thr Ile Ser Gln Val Ala Ala Ile Ser Ala Arg Asp Gly Ser Gly Val
65                  70                  75                  80

Thr Val Glu Leu Ser Glu Ala Ala Arg Ala Gly Val Lys Ala Ser Ser
```

-continued

```
                85                  90                  95

Asp Trp Val Met Asp Ser Met Asn Lys Gly Thr Asp Ser Tyr Gly Val
            100                 105                 110

Thr Thr Gly Phe Gly Ala Thr Ser His Arg Arg Thr Lys Gln Gly Gly
        115                 120                 125

Ala Leu Gln Lys Glu Leu Ile Arg Phe Leu Asn Ala Gly Ile Phe Gly
    130                 135                 140

Asn Gly Ser Asp Asn Thr Leu Pro His Ser Ala Thr Arg Ala Ala Met
145                 150                 155                 160

Leu Val Arg Ile Asn Thr Leu Leu Gln Gly Tyr Ser Gly Ile Arg Phe
                165                 170                 175

Glu Ile Leu Glu Ala Ile Thr Lys Phe Leu Asn Gln Asn Ile Thr Pro
            180                 185                 190

Cys Leu Pro Leu Arg Gly Thr Ile Thr Ala Ser Gly Asp Leu Val Pro
        195                 200                 205

Leu Ser Tyr Ile Ala Gly Leu Leu Thr Gly Arg Pro Asn Ser Lys Ala
    210                 215                 220

Val Gly Pro Thr Gly Val Ile Leu Ser Pro Glu Glu Ala Phe Lys Leu
225                 230                 235                 240

Ala Gly Val Glu Gly Gly Phe Phe Glu Leu Gln Pro Lys Glu Gly Leu
                245                 250                 255

Ala Leu Val Asn Gly Thr Ala Val Gly Ser Gly Met Ala Ser Met Val
            260                 265                 270

Leu Phe Glu Ala Asn Ile Leu Ala Val Leu Ala Glu Val Met Ser Ala
        275                 280                 285

Ile Phe Ala Glu Val Met Gln Gly Lys Pro Glu Phe Thr Asp His Leu
    290                 295                 300

Thr His Lys Leu Lys His His Pro Gly Gln Ile Glu Ala Ala Ala Ile
305                 310                 315                 320

Met Glu His Ile Leu Asp Gly Ser Ala Tyr Val Lys Ala Ala Gln Lys
                325                 330                 335

Leu His Glu Met Asp Pro Leu Gln Lys Pro Lys Gln Asp Arg Tyr Ala
            340                 345                 350

Leu Arg Thr Ser Pro Gln Trp Leu Gly Pro Gln Ile Glu Val Ile Arg
        355                 360                 365

Ser Ser Thr Lys Met Ile Glu Arg Glu Ile Asn Ser Val Asn Asp Asn
    370                 375                 380

Pro Leu Ile Asp Val Ser Arg Asn Lys Ala Ile His Gly Gly Asn Phe
385                 390                 395                 400

Gln Gly Thr Pro Ile Gly Val Ser Met Asp Asn Thr Arg Leu Ala Ile
                405                 410                 415

Ala Ala Ile Gly Lys Leu Met Phe Ala Gln Phe Ser Glu Leu Val Asn
            420                 425                 430

Asp Phe Tyr Asn Asn Gly Leu Pro Ser Asn Leu Ser Gly Gly Arg Asn
        435                 440                 445

Pro Ser Leu Asp Tyr Gly Phe Lys Gly Ala Glu Ile Ala Met Ala Ser
    450                 455                 460

Tyr Cys Ser Glu Leu Gln Phe Leu Ala Asn Pro Val Thr Asn His Val
465                 470                 475                 480

Gln Ser Ala Glu Gln His Asn Gln Asp Val Asn Ser Leu Gly Leu Ile
                485                 490                 495

Ser Ser Arg Lys Thr Ser Glu Ala Val Glu Ile Leu Lys Leu Met Ser
            500                 505                 510
```

```
Thr Thr Phe Leu Val Gly Leu Cys Gln Ala Ile Asp Leu Arg His Leu
        515                 520                 525

Glu Glu Asn Leu Lys Ser Thr Val Lys Asn Thr Val Ser Ser Val Ala
    530                 535                 540

Lys Arg Val Leu Thr Met Gly Val Asn Gly Glu Leu His Pro Ser Arg
545                 550                 555                 560

Phe Cys Glu Lys Asp Leu Leu Arg Val Val Asp Arg Glu Tyr Ile Phe
                565                 570                 575

Ala Tyr Ile Asp Asp Pro Cys Ser Ala Thr Tyr Pro Leu Met Gln Lys
            580                 585                 590

Leu Arg Gln Thr Leu Val Glu His Ala Leu Lys Asn Gly Asp Asn Glu
        595                 600                 605

Arg Asn Leu Ser Thr Ser Ile Phe Gln Lys Ile Ala Thr Phe Glu Asp
    610                 615                 620

Glu Leu Lys Ala Leu Leu Pro Lys Glu Val Glu Ser Ala Arg Ala Ala
625                 630                 635                 640

Leu Glu Ser Gly Asn Pro Ala Ile Pro Asn Arg Ile Glu Glu Cys Arg
                645                 650                 655

Ser Tyr Pro Leu Tyr Lys Phe Val Arg Lys Glu Leu Gly Thr Glu Tyr
            660                 665                 670

Leu Thr Gly Glu Lys Val Thr Ser Pro Gly Glu Glu Phe Glu Lys Val
        675                 680                 685

Phe Ile Ala Met Ser Lys Gly Glu Ile Ile Asp Pro Leu Leu Glu Cys
    690                 695                 700

Leu Glu Ser Trp Asn Gly Ala Pro Leu Pro Ile Cys
705                 710                 715


<210> SEQ ID NO 7
<211> LENGTH: 716
<212> TYPE: PRT
<213> ORGANISM: Rhodosporidium toruloides mutant

<400> SEQUENCE: 7

Met Ala Pro Ser Leu Asp Ser Ile Ser His Ser Phe Ala Asn Gly Val
1               5                   10                  15

Ala Ser Ala Lys Gln Ala Val Asn Gly Ala Ser Thr Asn Leu Ala Val
            20                  25                  30

Ala Gly Ser His Leu Pro Thr Thr Gln Val Thr Gln Val Asp Ile Val
        35                  40                  45

Glu Lys Met Leu Ala Ala Pro Thr Asp Ser Thr Leu Glu Leu Asp Gly
    50                  55                  60

Tyr Ser Leu Asn Leu Gly Asp Val Val Ser Ala Ala Arg Lys Gly Arg
65                  70                  75                  80

Pro Val Arg Val Lys Asp Ser Asp Glu Ile Arg Ser Lys Ile Asp Lys
                85                  90                  95

Ser Val Glu Phe Leu Arg Ser Gln Leu Ser Met Ser Val Tyr Gly Val
            100                 105                 110

Thr Thr Gly Phe Gly Gly Ser Ala Asp Thr Arg Thr Glu Asp Ala Ile
        115                 120                 125

Ser Leu Gln Lys Ala Leu Leu Glu His Gln Leu Cys Gly Val Leu Pro
    130                 135                 140

Ser Ser Phe Asp Ser Phe Arg Leu Gly Arg Gly Leu Glu Asn Ser Leu
145                 150                 155                 160

Pro Leu Glu Val Val Arg Gly Ala Met Thr Ile Arg Val Asn Ser Leu
                165                 170                 175
```

```
Thr Arg Gly His Ser Ala Val Arg Leu Val Val Leu Glu Ala Leu Thr
            180                 185                 190

Asn Phe Leu Asn His Gly Ile Thr Pro Ile Val Pro Leu Arg Gly Thr
        195                 200                 205

Ile Ser Ala Ser Gly Asp Leu Ser Pro Leu Ser Tyr Ile Ala Ala Ala
    210                 215                 220

Ile Ser Gly His Pro Asp Ser Lys Val His Val Val His Glu Gly Lys
225                 230                 235                 240

Glu Lys Ile Leu Tyr Ala Arg Glu Ala Met Ala Leu Phe Asn Leu Glu
                245                 250                 255

Pro Val Val Leu Gly Pro Lys Glu Gly Leu Gly Leu Val Asn Gly Thr
            260                 265                 270

Ala Val Ser Ala Ser Met Ala Thr Leu Ala Leu His Asp Ala His Met
        275                 280                 285

Leu Ser Leu Leu Ser Gln Ser Leu Thr Ala Met Thr Val Glu Ala Met
    290                 295                 300

Val Gly His Ala Gly Ser Phe His Pro Phe Leu His Asp Val Thr Arg
305                 310                 315                 320

Pro His Pro Thr Gln Ile Glu Val Ala Gly Asn Ile Arg Lys Leu Leu
                325                 330                 335

Glu Gly Ser Arg Phe Ala Val His His Glu Glu Glu Val Lys Val Lys
            340                 345                 350

Asp Asp Glu Gly Ile Leu Arg Gln Asp Arg Tyr Pro Leu Arg Thr Ser
        355                 360                 365

Pro Gln Trp Leu Gly Pro Leu Val Ser Asp Leu Ile His Ala His Ala
    370                 375                 380

Val Leu Thr Ile Glu Ala Gly Gln Ser Thr Thr Asp Asn Pro Leu Ile
385                 390                 395                 400

Asp Val Glu Asn Lys Thr Ser His His Gly Gly Asn Phe Gln Ala Ala
                405                 410                 415

Ala Val Ala Asn Thr Met Glu Lys Thr Arg Leu Gly Leu Ala Gln Ile
            420                 425                 430

Gly Lys Leu Asn Phe Thr Gln Leu Thr Glu Met Leu Asn Ala Gly Met
        435                 440                 445

Asn Arg Gly Leu Pro Ser Cys Leu Ala Ala Glu Asp Pro Ser Leu Ser
    450                 455                 460

Tyr His Cys Lys Gly Leu Asp Ile Ala Ala Ala Ala Tyr Thr Ser Glu
465                 470                 475                 480

Leu Gly His Leu Ala Asn Pro Val Thr Thr His Val Gln Pro Ala Glu
                485                 490                 495

Met Ala Asn Gln Ala Val Asn Ser Leu Ala Leu Ile Ser Ala Arg Arg
            500                 505                 510

Thr Thr Glu Ser Asn Asp Val Leu Ser Leu Leu Leu Ala Thr His Leu
        515                 520                 525

Tyr Cys Val Leu Gln Ala Ile Asp Leu Arg Ala Thr Glu Phe Glu Phe
    530                 535                 540

Lys Lys Gln Phe Gly Pro Ala Ile Val Ser Leu Ile Asp Gln His Phe
545                 550                 555                 560

Gly Ser Ala Met Thr Gly Ser Asn Leu Arg Asp Glu Leu Val Glu Lys
                565                 570                 575

Val Asn Lys Thr Leu Ala Lys Arg Leu Glu Gln Thr Asn Ser Tyr Asp
            580                 585                 590

Leu Val Pro Arg Trp His Asp Ala Phe Ser Phe Ala Ala Gly Thr Val
        595                 600                 605
```

```
Val Glu Val Leu Ser Ser Thr Ser Leu Ser Leu Ala Ala Val Asn Ala
    610                 615                 620

Trp Lys Val Ala Ala Ala Glu Ser Ala Ile Ser Leu Thr Arg Gln Val
625                 630                 635                 640

Arg Glu Thr Phe Trp Ser Ala Ala Ser Thr Ser Ser Pro Ala Leu Ser
                645                 650                 655

Tyr Leu Ser Pro Arg Thr Gln Ile Leu Tyr Ala Phe Val Arg Glu Glu
            660                 665                 670

Leu Gly Val Lys Ala Arg Arg Gly Asp Val Phe Leu Gly Lys Gln Glu
        675                 680                 685

Val Thr Ile Gly Ser Asn Val Ser Lys Ile Tyr Glu Ala Ile Lys Ser
    690                 695                 700

Gly Arg Ile Asn Asn Val Leu Leu Lys Met Leu Ala
705                 710                 715


<210> SEQ ID NO 8
<211> LENGTH: 670
<212> TYPE: PRT
<213> ORGANISM: Rhodotorula glutinis
<220> FEATURE:
<221> NAME/KEY: misc_feature
<222> LOCATION: (126)..(126)
<223> OTHER INFORMATION: Xaa can be any naturally occurring amino acid
<220> FEATURE:
<221> NAME/KEY: misc_feature
<222> LOCATION: (138)..(138)
<223> OTHER INFORMATION: Xaa can be any naturally occurring amino acid
<220> FEATURE:
<221> NAME/KEY: misc_feature
<222> LOCATION: (540)..(540)
<223> OTHER INFORMATION: Xaa can be any naturally occurring amino acid

<400> SEQUENCE: 8

Met Ala Pro Ser Leu Asp Ser Ile Ser His Ser Phe Ala Asn Gly Val
1               5                   10                  15

Ala Ser Ala Lys Gln Ala Val Asn Gly Ala Ser Thr Asn Leu Ala Val
            20                  25                  30

Ala Gly Ser His Leu Pro Thr Thr Gln Val Thr Gln Val Asp Ile Val
        35                  40                  45

Glu Lys Met Leu Ala Ala Pro Thr Asp Ser Thr Leu Glu Leu Asp Gly
    50                  55                  60

Tyr Ser Leu Asn Leu Gly Asp Val Val Ser Ala Ala Arg Lys Gly Arg
65                  70                  75                  80

Pro Val Arg Val Lys Asp Ser Asp Glu Ile Arg Ser Lys Ile Asp Lys
                85                  90                  95

Ser Val Glu Phe Leu Arg Ser Gln Leu Ser Met Ser Val Tyr Gly Val
            100                 105                 110

Thr Thr Gly Phe Gly Gly Ser Ala Asp Thr Arg Thr Glu Xaa Ala Ile
        115                 120                 125

Ser Leu Gln Lys Ala Leu Leu Glu His Xaa Leu Cys Gly Val Leu Pro
    130                 135                 140

Ser Ser Phe Asp Ser Phe Arg Leu Gly Arg Gly Leu Glu Asn Ser Leu
145                 150                 155                 160

Pro Leu Glu Val Val Arg Gly Ala Met Thr Ile Arg Val Asn Ser Leu
                165                 170                 175

Thr Arg Gly His Ser Ala Val Arg Leu Val Val Leu Glu Ala Leu Thr
            180                 185                 190

Asn Phe Leu Asn His Gly Ile Thr Pro Ile Val Pro Leu Arg Gly Thr
        195                 200                 205
```

```
Ile Ser Ala Ser Gly Asp Leu Ser Pro Leu Ser Tyr Ile Ala Ala Ala
    210                 215                 220

Ile Ser Gly His Pro Asp Ser Lys Val His Val Val His Glu Gly Lys
225                 230                 235                 240

Glu Lys Ile Leu Tyr Ala Arg Glu Ala Met Ala Leu Phe Asn Leu Glu
                245                 250                 255

Pro Val Val Leu Gly Pro Lys Glu Gly Leu Gly Leu Val Asn Gly Thr
            260                 265                 270

Ala Val Ser Ala Ser Met Ala Thr Leu Ala Leu His Asp Ala His Met
        275                 280                 285

Leu Ser Leu Leu Ser Gln Ser Leu Thr Ala Met Thr Val Glu Ala Met
    290                 295                 300

Val Gly His Ala Gly Ser Phe His Pro Phe Leu His Asp Val Thr Arg
305                 310                 315                 320

Pro His Pro Thr Gln Ile Glu Val Ala Gly Asn Ile Arg Lys Leu Leu
                325                 330                 335

Glu Gly Ser Arg Phe Ala Val His His Glu Glu Glu Val Lys Val Lys
            340                 345                 350

Asp Asp Glu Gly Ile Leu Arg Gln Asp Arg Tyr Pro Leu Arg Thr Ser
        355                 360                 365

Pro Gln Trp Leu Gly Pro Leu Val Ser Asp Leu Ile His Ala His Ala
    370                 375                 380

Val Leu Thr Ile Glu Ala Gly Gln Ser Thr Thr Asp Asn Pro Leu Ile
385                 390                 395                 400

Asp Val Glu Asn Lys Thr Ser His His Gly Gly Asn Phe Gln Ala Ala
                405                 410                 415

Ala Val Ala Asn Thr Met Glu Lys Thr Arg Leu Gly Leu Ala Gln Ile
            420                 425                 430

Gly Lys Leu Asn Phe Thr Gln Leu Thr Glu Met Leu Asn Ala Gly Met
        435                 440                 445

Asn Arg Gly Leu Pro Ser Cys Leu Ala Ala Glu Asp Pro Ser Leu Ser
    450                 455                 460

Tyr His Cys Lys Gly Leu Asp Ile Ala Ala Ala Ala Tyr Thr Ser Glu
465                 470                 475                 480

Leu Gly His Leu Ala Asn Pro Val Thr Thr His Val Gln Pro Ala Glu
                485                 490                 495

Met Ala Asn Gln Ala Val Asn Ser Leu Ala Leu Ile Ser Ala Arg Arg
            500                 505                 510

Thr Thr Glu Ser Asn Asp Val Leu Ser Leu Leu Leu Ala Thr His Leu
        515                 520                 525

Tyr Cys Val Leu Gln Ala Ile Asp Leu Arg Ala Xaa Glu Phe Glu Phe
    530                 535                 540

Lys Lys Gln Phe Gly Pro Ala Ile Val Ser Leu Ile Asp Gln His Phe
545                 550                 555                 560

Gly Ser Ala Met Thr Gly Ser Asn Leu Arg Asp Glu Leu Val Glu Lys
                565                 570                 575

Val Asn Lys Thr Leu Ala Lys Arg Leu Glu Gln Thr Asn Ser Tyr Asp
            580                 585                 590

Leu Val Pro Arg Trp His Asp Ala Phe Ser Phe Ala Ala Gly Thr Val
        595                 600                 605

Val Glu Val Leu Ser Ser Thr Ser Leu Ser Leu Ala Ala Val Asn Ala
    610                 615                 620

Trp Lys Val Ala Ala Ala Glu Ser Ala Ile Ser Leu Thr Arg Gln Val
```

```
625                 630                 635                 640

Arg Glu Thr Phe Trp Ser Ala Ala Ser Thr Ser Ser Pro Ala Leu Ser
                645                 650                 655

Tyr Leu Ser Pro Arg Thr Gln Ile Leu Tyr Ala Phe Val Arg
            660                 665                 670


<210> SEQ ID NO 9
<211> LENGTH: 680
<212> TYPE: PRT
<213> ORGANISM: Rhodotorula glutinis mutant
<220> FEATURE:
<221> NAME/KEY: misc_feature
<222> LOCATION: (198)..(198)
<223> OTHER INFORMATION: Xaa can be any naturally occurring amino acid
<220> FEATURE:
<221> NAME/KEY: misc_feature
<222> LOCATION: (540)..(540)
<223> OTHER INFORMATION: Xaa can be any naturally occurring amino acid

<400> SEQUENCE: 9

Met Ala Pro Ser Leu Asp Ser Ile Ser His Ser Phe Ala Asn Gly Val
1               5                   10                  15

Ala Ser Ala Lys Gln Ala Val Asn Gly Ala Ser Thr Asn Leu Ala Val
            20                  25                  30

Ala Gly Ser His Leu Pro Thr Thr Gln Val Thr Gln Val Asp Ile Val
        35                  40                  45

Glu Lys Met Leu Ala Ala Pro Thr Asp Ser Thr Leu Glu Leu Asp Gly
    50                  55                  60

Tyr Ser Leu Asn Leu Gly Asp Val Val Ser Ala Ala Arg Lys Gly Arg
65                  70                  75                  80

Pro Val Arg Val Lys Asp Ser Asp Glu Ile Arg Ser Lys Ile Asp Lys
                85                  90                  95

Ser Val Glu Phe Leu Arg Ser Gln Leu Ser Met Ser Val Tyr Gly Val
            100                 105                 110

Thr Thr Gly Phe Gly Gly Ser Ala Asp Thr Arg Thr Glu Asp Ala Ile
        115                 120                 125

Ser Leu Gln Lys Ala Leu Leu Glu His Gln Leu Cys Gly Val Leu Pro
    130                 135                 140

Ser Ser Phe Asp Ser Phe Arg Leu Gly Arg Gly Leu Glu Asn Ser Leu
145                 150                 155                 160

Pro Leu Glu Val Val Arg Gly Ala Met Thr Ile Arg Val Asn Ser Leu
                165                 170                 175

Thr Arg Gly His Ser Ala Val Arg Leu Val Val Leu Glu Ala Leu Thr
            180                 185                 190

Asn Phe Leu Asn His Xaa Ile Thr Pro Ile Val Pro Leu Arg Gly Thr
        195                 200                 205

Ile Ser Ala Ser Gly Asp Leu Ser Pro Leu Ser Tyr Ile Ala Ala Ala
    210                 215                 220

Ile Ser Gly His Pro Asp Ser Lys Val His Val Val His Glu Gly Lys
225                 230                 235                 240

Glu Lys Ile Leu Tyr Ala Arg Glu Ala Met Ala Leu Phe Asn Leu Glu
                245                 250                 255

Pro Val Val Leu Gly Pro Lys Glu Gly Leu Gly Leu Val Asn Gly Thr
            260                 265                 270

Ala Val Ser Ala Ser Met Ala Thr Leu Ala Leu His Asp Ala His Met
        275                 280                 285

Leu Ser Leu Leu Ser Gln Ser Leu Thr Ala Met Thr Val Glu Ala Met
    290                 295                 300
```

```
Val Gly His Ala Gly Ser Phe His Pro Phe Leu His Asp Val Thr Arg
305                 310                 315                 320

Pro His Pro Thr Gln Ile Glu Val Ala Gly Asn Ile Arg Lys Leu Leu
                325                 330                 335

Glu Gly Ser Arg Phe Ala Val His His Glu Glu Glu Val Lys Val Lys
            340                 345                 350

Asp Asp Glu Gly Ile Leu Arg Gln Asp Arg Tyr Pro Leu Arg Thr Ser
        355                 360                 365

Pro Gln Trp Leu Gly Pro Leu Val Ser Asp Leu Ile His Ala His Ala
    370                 375                 380

Val Leu Thr Ile Glu Ala Gly Gln Ser Thr Thr Asp Asn Pro Leu Ile
385                 390                 395                 400

Asp Val Glu Asn Lys Thr Ser His His Gly Gly Asn Phe Gln Ala Ala
                405                 410                 415

Ala Val Ala Asn Thr Met Glu Lys Thr Arg Leu Gly Leu Ala Gln Ile
            420                 425                 430

Gly Lys Leu Asn Phe Thr Gln Leu Thr Glu Met Leu Asn Ala Gly Met
        435                 440                 445

Asn Arg Gly Leu Pro Ser Cys Leu Ala Ala Glu Asp Pro Ser Leu Ser
    450                 455                 460

Tyr His Cys Lys Gly Leu Asp Ile Ala Ala Ala Ala Tyr Thr Ser Glu
465                 470                 475                 480

Leu Gly His Leu Ala Asn Pro Val Thr Thr His Val Gln Pro Ala Glu
                485                 490                 495

Met Ala Asn Gln Ala Val Asn Ser Leu Ala Leu Ile Ser Ala Arg Arg
            500                 505                 510

Thr Thr Glu Ser Asn Asp Val Leu Ser Leu Leu Leu Ala Thr His Leu
        515                 520                 525

Tyr Cys Val Leu Gln Ala Ile Asp Leu Arg Ala Xaa Glu Phe Glu Phe
    530                 535                 540

Lys Lys Gln Phe Gly Pro Ala Ile Val Ser Leu Ile Asp Gln His Phe
545                 550                 555                 560

Gly Ser Ala Met Thr Gly Ser Asn Leu Arg Asp Glu Leu Val Glu Lys
                565                 570                 575

Val Asn Lys Thr Leu Ala Lys Arg Leu Glu Gln Thr Asn Ser Tyr Asp
            580                 585                 590

Leu Val Pro Arg Trp His Asp Ala Phe Ser Phe Ala Ala Gly Thr Val
        595                 600                 605

Val Glu Val Leu Ser Ser Thr Ser Leu Ser Leu Ala Ala Val Asn Ala
    610                 615                 620

Trp Lys Val Ala Ala Ala Glu Ser Ala Ile Ser Leu Thr Arg Gln Val
625                 630                 635                 640

Arg Glu Thr Phe Trp Ser Ala Ala Ser Thr Ser Ser Pro Ala Leu Ser
                645                 650                 655

Tyr Leu Ser Pro Arg Thr Gln Ile Leu Tyr Ala Phe Val Arg Glu Glu
            660                 665                 670

Leu Gly Val Lys Ala Arg Arg Gly
        675                 680
```

<210> SEQ ID NO 10
<211> LENGTH: 716
<212> TYPE: PRT
<213> ORGANISM: Rhodotorula glutinis
<220> FEATURE:
<221> NAME/KEY: misc_feature
<222> LOCATION: (181)..(181)
<223> OTHER INFORMATION: Xaa can be any naturally occurring amino acid
<220> FEATURE:
<221> NAME/KEY: misc_feature
<222> LOCATION: (235)..(235)
<223> OTHER INFORMATION: Xaa can be any naturally occurring amino acid
<220> FEATURE:
<221> NAME/KEY: misc_feature
<222> LOCATION: (540)..(540)
<223> OTHER INFORMATION: Xaa can be any naturally occurring amino acid

<400> SEQUENCE: 10

```
Met Ala Pro Ser Leu Asp Ser Ile Ser His Ser Phe Ala Asn Gly Val
1               5                   10                  15

Ala Ser Ala Lys Gln Ala Val Asn Gly Ala Ser Thr Asn Leu Ala Val
            20                  25                  30

Ala Gly Ser His Leu Pro Thr Thr Gln Val Thr Gln Val Asp Ile Val
        35                  40                  45

Glu Lys Met Leu Ala Ala Pro Thr Asp Ser Thr Leu Glu Leu Asp Gly
    50                  55                  60

Tyr Ser Leu Asn Leu Gly Asp Val Val Ser Ala Ala Arg Lys Gly Arg
65                  70                  75                  80

Pro Val Arg Val Lys Asp Ser Asp Glu Ile Arg Ser Lys Ile Asp Lys
                85                  90                  95

Ser Val Glu Phe Leu Arg Ser Gln Leu Ser Met Ser Val Tyr Gly Val
            100                 105                 110

Thr Thr Gly Phe Gly Gly Ser Ala Asp Thr Arg Thr Glu Asp Ala Ile
        115                 120                 125

Ser Leu Gln Lys Ala Leu Leu Glu His Gln Leu Cys Gly Val Leu Pro
    130                 135                 140

Ser Ser Phe Asp Ser Phe Arg Leu Gly Arg Gly Leu Glu Asn Ser Leu
145                 150                 155                 160

Pro Leu Glu Val Val Arg Gly Ala Met Thr Ile Arg Val Asn Ser Leu
                165                 170                 175

Thr Arg Gly His Xaa Ala Val Arg Leu Val Val Leu Glu Ala Leu Thr
            180                 185                 190

Asn Phe Leu Asn His Gly Ile Thr Pro Ile Val Pro Leu Arg Gly Thr
        195                 200                 205

Ile Ser Ala Ser Gly Asp Leu Ser Pro Leu Ser Tyr Ile Ala Ala Ala
    210                 215                 220

Ile Ser Gly His Pro Asp Ser Lys Val His Xaa Val His Glu Gly Lys
225                 230                 235                 240

Glu Lys Ile Leu Tyr Ala Arg Glu Ala Met Ala Leu Phe Asn Leu Glu
                245                 250                 255

Pro Val Val Leu Gly Pro Lys Glu Gly Leu Gly Leu Val Asn Gly Thr
            260                 265                 270

Ala Val Ser Ala Ser Met Ala Thr Leu Ala Leu His Asp Ala His Met
        275                 280                 285

Leu Ser Leu Leu Ser Gln Ser Leu Thr Ala Met Thr Val Glu Ala Met
    290                 295                 300

Val Gly His Ala Gly Ser Phe His Pro Phe Leu His Asp Val Thr Arg
305                 310                 315                 320

Pro His Pro Thr Gln Ile Glu Val Ala Gly Asn Ile Arg Lys Leu Leu
                325                 330                 335

Glu Gly Ser Arg Phe Ala Val His His Glu Glu Glu Val Lys Val Lys
            340                 345                 350

Asp Asp Glu Gly Ile Leu Arg Gln Asp Arg Tyr Pro Leu Arg Thr Ser
```

```
        355                 360                 365

Pro Gln Trp Leu Gly Pro Leu Val Ser Asp Leu Ile His Ala His Ala
    370                 375                 380

Val Leu Thr Ile Glu Ala Gly Gln Ser Thr Thr Asp Asn Pro Leu Ile
385                 390                 395                 400

Asp Val Glu Asn Lys Thr Ser His His Gly Gly Asn Phe Gln Ala Ala
                405                 410                 415

Ala Val Ala Asn Thr Met Glu Lys Thr Arg Leu Gly Leu Ala Gln Ile
            420                 425                 430

Gly Lys Leu Asn Phe Thr Gln Leu Thr Glu Met Leu Asn Ala Gly Met
        435                 440                 445

Asn Arg Gly Leu Pro Ser Cys Leu Ala Ala Glu Asp Pro Ser Leu Ser
    450                 455                 460

Tyr His Cys Lys Gly Leu Asp Ile Ala Ala Ala Ala Tyr Thr Ser Glu
465                 470                 475                 480

Leu Gly His Leu Ala Asn Pro Val Thr Thr His Val Gln Pro Ala Glu
                485                 490                 495

Met Ala Asn Gln Ala Val Asn Ser Leu Ala Leu Ile Ser Ala Arg Arg
            500                 505                 510

Thr Thr Glu Ser Asn Asp Val Leu Ser Leu Leu Leu Ala Thr His Leu
        515                 520                 525

Tyr Cys Val Leu Gln Ala Ile Asp Leu Arg Ala Xaa Glu Phe Glu Phe
    530                 535                 540

Lys Lys Gln Phe Gly Pro Ala Ile Val Ser Leu Ile Asp Gln His Phe
545                 550                 555                 560

Gly Ser Ala Met Thr Gly Ser Asn Leu Arg Asp Glu Leu Val Glu Lys
                565                 570                 575

Val Asn Lys Thr Leu Ala Lys Arg Leu Glu Gln Thr Asn Ser Tyr Asp
            580                 585                 590

Leu Val Pro Arg Trp His Asp Ala Phe Ser Phe Ala Ala Gly Thr Val
        595                 600                 605

Val Glu Val Leu Ser Ser Thr Ser Leu Ser Leu Ala Ala Val Asn Ala
    610                 615                 620

Trp Lys Val Ala Ala Ala Glu Ser Ala Ile Ser Leu Thr Arg Gln Val
625                 630                 635                 640

Arg Glu Thr Phe Trp Ser Ala Ala Ser Thr Ser Ser Pro Ala Leu Ser
                645                 650                 655

Tyr Leu Ser Pro Arg Thr Gln Ile Leu Tyr Ala Phe Val Arg Glu Glu
            660                 665                 670

Leu Gly Val Lys Ala Arg Arg Gly Asp Val Phe Leu Gly Lys Gln Glu
        675                 680                 685

Val Thr Ile Gly Ser Asn Val Ser Lys Ile Tyr Glu Ala Ile Lys Ser
    690                 695                 700

Gly Arg Ile Asn Asn Val Leu Leu Lys Met Leu Ala
705                 710                 715
```

<210> SEQ ID NO 11
<211> LENGTH: 716
<212> TYPE: PRT
<213> ORGANISM: Rhodotorula glutinis mutant
<220> FEATURE:
<221> NAME/KEY: misc_feature
<222> LOCATION: (149)..(149)
<223> OTHER INFORMATION: Xaa can be any naturally occurring amino acid
<220> FEATURE:
<221> NAME/KEY: misc_feature
<222> LOCATION: (202)..(202)

```
<223> OTHER INFORMATION: Xaa can be any naturally occurring amino acid
<220> FEATURE:
<221> NAME/KEY: misc_feature
<222> LOCATION: (540)..(540)
<223> OTHER INFORMATION: Xaa can be any naturally occurring amino acid

<400> SEQUENCE: 11

Met Ala Pro Ser Leu Asp Ser Ile Ser His Ser Phe Ala Asn Gly Val
1               5                   10                  15

Ala Ser Ala Lys Gln Ala Val Asn Gly Ala Ser Thr Asn Leu Ala Val
            20                  25                  30

Ala Gly Ser His Leu Pro Thr Thr Gln Val Thr Gln Val Asp Ile Val
        35                  40                  45

Glu Lys Met Leu Ala Ala Pro Thr Asp Ser Thr Leu Glu Leu Asp Gly
    50                  55                  60

Tyr Ser Leu Asn Leu Gly Asp Val Val Ser Ala Ala Arg Lys Gly Arg
65                  70                  75                  80

Pro Val Arg Val Lys Asp Ser Asp Glu Ile Arg Ser Lys Ile Asp Lys
                85                  90                  95

Ser Val Glu Phe Leu Arg Ser Gln Leu Ser Met Ser Val Tyr Gly Val
            100                 105                 110

Thr Thr Gly Phe Gly Gly Ser Ala Asp Thr Arg Thr Glu Asp Ala Ile
        115                 120                 125

Ser Leu Gln Lys Ala Leu Leu Glu His Gln Leu Cys Gly Val Leu Pro
    130                 135                 140

Ser Ser Phe Asp Xaa Phe Arg Leu Gly Arg Gly Leu Glu Asn Ser Leu
145                 150                 155                 160

Pro Leu Glu Val Val Arg Gly Ala Met Thr Ile Arg Val Asn Ser Leu
                165                 170                 175

Thr Arg Gly His Ser Ala Val Arg Leu Val Val Leu Glu Ala Leu Thr
            180                 185                 190

Asn Phe Leu Asn His Gly Ile Thr Pro Xaa Val Pro Leu Arg Gly Thr
        195                 200                 205

Ile Ser Ala Ser Gly Asp Leu Ser Pro Leu Ser Tyr Ile Ala Ala Ala
    210                 215                 220

Ile Ser Gly His Pro Asp Ser Lys Val His Val Val His Glu Gly Lys
225                 230                 235                 240

Glu Lys Ile Leu Tyr Ala Arg Glu Ala Met Ala Leu Phe Asn Leu Glu
                245                 250                 255

Pro Val Val Leu Gly Pro Lys Glu Gly Leu Gly Leu Val Asn Gly Thr
            260                 265                 270

Ala Val Ser Ala Ser Met Ala Thr Leu Ala Leu His Asp Ala His Met
        275                 280                 285

Leu Ser Leu Leu Ser Gln Ser Leu Thr Ala Met Thr Val Glu Ala Met
    290                 295                 300

Val Gly His Ala Gly Ser Phe His Pro Phe Leu His Asp Val Thr Arg
305                 310                 315                 320

Pro His Pro Thr Gln Ile Glu Val Ala Gly Asn Ile Arg Lys Leu Leu
                325                 330                 335

Glu Gly Ser Arg Phe Ala Val His His Glu Glu Glu Val Lys Val Lys
            340                 345                 350

Asp Asp Glu Gly Ile Leu Arg Gln Asp Arg Tyr Pro Leu Arg Thr Ser
        355                 360                 365

Pro Gln Trp Leu Gly Pro Leu Val Ser Asp Leu Ile His Ala His Ala
    370                 375                 380
```

```
Val Leu Thr Ile Glu Ala Gly Gln Ser Thr Thr Asp Asn Pro Leu Ile
385                 390                 395                 400

Asp Val Glu Asn Lys Thr Ser His His Gly Gly Asn Phe Gln Ala Ala
                405                 410                 415

Ala Val Ala Asn Thr Met Glu Lys Thr Arg Leu Gly Leu Ala Gln Ile
            420                 425                 430

Gly Lys Leu Asn Phe Thr Gln Leu Thr Glu Met Leu Asn Ala Gly Met
        435                 440                 445

Asn Arg Gly Leu Pro Ser Cys Leu Ala Ala Glu Asp Pro Ser Leu Ser
    450                 455                 460

Tyr His Cys Lys Gly Leu Asp Ile Ala Ala Ala Ala Tyr Thr Ser Glu
465                 470                 475                 480

Leu Gly His Leu Ala Asn Pro Val Thr Thr His Val Gln Pro Ala Glu
                485                 490                 495

Met Ala Asn Gln Ala Val Asn Ser Leu Ala Leu Ile Ser Ala Arg Arg
            500                 505                 510

Thr Thr Glu Ser Asn Asp Val Leu Ser Leu Leu Leu Ala Thr His Leu
        515                 520                 525

Tyr Cys Val Leu Gln Ala Ile Asp Leu Arg Ala Xaa Glu Phe Glu Phe
    530                 535                 540

Lys Lys Gln Phe Gly Pro Ala Ile Val Ser Leu Ile Asp Gln His Phe
545                 550                 555                 560

Gly Ser Ala Met Thr Gly Ser Asn Leu Arg Asp Glu Leu Val Glu Lys
                565                 570                 575

Val Asn Lys Thr Leu Ala Lys Arg Leu Glu Gln Thr Asn Ser Tyr Asp
            580                 585                 590

Leu Val Pro Arg Trp His Asp Ala Phe Ser Phe Ala Ala Gly Thr Val
        595                 600                 605

Val Glu Val Leu Ser Ser Thr Ser Leu Ser Leu Ala Ala Val Asn Ala
    610                 615                 620

Trp Lys Val Ala Ala Ala Glu Ser Ala Ile Ser Leu Thr Arg Gln Val
625                 630                 635                 640

Arg Glu Thr Phe Trp Ser Ala Ala Ser Thr Ser Ser Pro Ala Leu Ser
                645                 650                 655

Tyr Leu Ser Pro Arg Thr Gln Ile Leu Tyr Ala Phe Val Arg Glu Glu
            660                 665                 670

Leu Gly Val Lys Ala Arg Arg Gly Asp Val Phe Leu Gly Lys Gln Glu
        675                 680                 685

Val Thr Ile Gly Ser Asn Val Ser Lys Ile Tyr Glu Ala Ile Lys Ser
    690                 695                 700

Gly Arg Ile Asn Asn Val Leu Leu Lys Met Leu Ala
705                 710                 715
```

<210> SEQ ID NO 12
<211> LENGTH: 716
<212> TYPE: PRT
<213> ORGANISM: Rhodotorula glutinis mutant
<220> FEATURE:
<221> NAME/KEY: misc_feature
<222> LOCATION: (502)..(502)
<223> OTHER INFORMATION: Xaa can be any naturally occurring amino acid
<220> FEATURE:
<221> NAME/KEY: misc_feature
<222> LOCATION: (540)..(540)
<223> OTHER INFORMATION: Xaa can be any naturally occurring amino acid

<400> SEQUENCE: 12

```
Met Ala Pro Ser Leu Asp Ser Ile Ser His Ser Phe Ala Asn Gly Val
```

-continued

```
1               5                   10                  15

Ala Ser Ala Lys Gln Ala Val Asn Gly Ala Ser Thr Asn Leu Ala Val
            20                  25                  30

Ala Gly Ser His Leu Pro Thr Thr Gln Val Thr Gln Val Asp Ile Val
        35                  40                  45

Glu Lys Met Leu Ala Ala Pro Thr Asp Ser Thr Leu Glu Leu Asp Gly
    50                  55                  60

Tyr Ser Leu Asn Leu Gly Asp Val Val Ser Ala Ala Arg Lys Gly Arg
65                  70                  75                  80

Pro Val Arg Val Lys Asp Ser Asp Glu Ile Arg Ser Lys Ile Asp Lys
                85                  90                  95

Ser Val Glu Phe Leu Arg Ser Gln Leu Ser Met Ser Val Tyr Gly Val
            100                 105                 110

Thr Thr Gly Phe Gly Gly Ser Ala Asp Thr Arg Thr Glu Asp Ala Ile
        115                 120                 125

Ser Leu Gln Lys Ala Leu Leu Glu His Gln Leu Cys Gly Val Leu Pro
    130                 135                 140

Ser Ser Phe Asp Ser Phe Arg Leu Gly Arg Gly Leu Glu Asn Ser Leu
145                 150                 155                 160

Pro Leu Glu Val Val Arg Gly Ala Met Thr Ile Arg Val Asn Ser Leu
                165                 170                 175

Thr Arg Gly His Ser Ala Val Arg Leu Val Val Leu Glu Ala Leu Thr
            180                 185                 190

Asn Phe Leu Asn His Gly Ile Thr Pro Ile Val Pro Leu Arg Gly Thr
        195                 200                 205

Ile Ser Ala Ser Gly Asp Leu Ser Pro Leu Ser Tyr Ile Ala Ala Ala
    210                 215                 220

Ile Ser Gly His Pro Asp Ser Lys Val His Val Val His Glu Gly Lys
225                 230                 235                 240

Glu Lys Ile Leu Tyr Ala Arg Glu Ala Met Ala Leu Phe Asn Leu Glu
                245                 250                 255

Pro Val Val Leu Gly Pro Lys Glu Gly Leu Gly Leu Val Asn Gly Thr
            260                 265                 270

Ala Val Ser Ala Ser Met Ala Thr Leu Ala Leu His Asp Ala His Met
        275                 280                 285

Leu Ser Leu Leu Ser Gln Ser Leu Thr Ala Met Thr Val Glu Ala Met
    290                 295                 300

Val Gly His Ala Gly Ser Phe His Pro Phe Leu His Asp Val Thr Arg
305                 310                 315                 320

Pro His Pro Thr Gln Ile Glu Val Ala Gly Asn Ile Arg Lys Leu Leu
                325                 330                 335

Glu Gly Ser Arg Phe Ala Val His His Glu Glu Glu Val Lys Val Lys
            340                 345                 350

Asp Asp Glu Gly Ile Leu Arg Gln Asp Arg Tyr Pro Leu Arg Thr Ser
        355                 360                 365

Pro Gln Trp Leu Gly Pro Leu Val Ser Asp Leu Ile His Ala His Ala
    370                 375                 380

Val Leu Thr Ile Glu Ala Gly Gln Ser Thr Thr Asp Asn Pro Leu Ile
385                 390                 395                 400

Asp Val Glu Asn Lys Thr Ser His His Gly Gly Asn Phe Gln Ala Ala
                405                 410                 415

Ala Val Ala Asn Thr Met Glu Lys Thr Arg Leu Gly Leu Ala Gln Ile
            420                 425                 430
```

```
Gly Lys Leu Asn Phe Thr Gln Leu Thr Glu Met Leu Asn Ala Gly Met
        435                 440                 445

Asn Arg Gly Leu Pro Ser Cys Leu Ala Ala Glu Asp Pro Ser Leu Ser
    450                 455                 460

Tyr His Cys Lys Gly Leu Asp Ile Ala Ala Ala Ala Tyr Thr Ser Glu
465                 470                 475                 480

Leu Gly His Leu Ala Asn Pro Val Thr Thr His Val Gln Pro Ala Glu
                485                 490                 495

Met Ala Asn Gln Ala Xaa Asn Ser Leu Ala Leu Ile Ser Ala Arg Arg
            500                 505                 510

Thr Thr Glu Ser Asn Asp Val Leu Ser Leu Leu Leu Ala Thr His Leu
        515                 520                 525

Tyr Cys Val Leu Gln Ala Ile Asp Leu Arg Ala Xaa Glu Phe Glu Phe
    530                 535                 540

Lys Lys Gln Phe Gly Pro Ala Ile Val Ser Leu Ile Asp Gln His Phe
545                 550                 555                 560

Gly Ser Ala Met Thr Gly Ser Asn Leu Arg Asp Glu Leu Val Glu Lys
                565                 570                 575

Val Asn Lys Thr Leu Ala Lys Arg Leu Glu Gln Thr Asn Ser Tyr Asp
            580                 585                 590

Leu Val Pro Arg Trp His Asp Ala Phe Ser Phe Ala Ala Gly Thr Val
        595                 600                 605

Val Glu Val Leu Ser Ser Thr Ser Leu Ser Leu Ala Ala Val Asn Ala
    610                 615                 620

Trp Lys Val Ala Ala Ala Glu Ser Ala Ile Ser Leu Thr Arg Gln Val
625                 630                 635                 640

Arg Glu Thr Phe Trp Ser Ala Ala Ser Thr Ser Ser Pro Ala Leu Ser
                645                 650                 655

Tyr Leu Ser Pro Arg Thr Gln Ile Leu Tyr Ala Phe Val Arg Glu Glu
            660                 665                 670

Leu Gly Val Lys Ala Arg Arg Gly Asp Val Phe Leu Gly Lys Gln Glu
        675                 680                 685

Val Thr Ile Gly Ser Asn Val Ser Lys Ile Tyr Glu Ala Ile Lys Ser
    690                 695                 700

Gly Arg Ile Asn Asn Val Leu Leu Lys Met Leu Ala
705                 710                 715
```

<210> SEQ ID NO 13
<211> LENGTH: 2148
<212> TYPE: DNA
<213> ORGANISM: Rhodotorula glutinis

<400> SEQUENCE: 13

```
atggcaccct cgctcgactc gatctcgcac tcgttcgcaa acggcgtcgc atccgcaaag     60

caggctgtca atggcgcctc gaccaacctc gcagtcgcag gctcgcacct gcccacaacc    120

caggtcacgc aggtcgacat cgtcgagaag atgctcgccg cgccgaccga ctcgacgctc    180

gaactcgacg gctactcgct caacctcgga gacgtcgtct cggccgcgag gaagggcagg    240

cctgtccgcg tcaaggacag cgacgagatc cgctcaaaga ttgacaaatc ggtcgagttc    300

ttgcgctcgc aactctccat gagcgtctac ggcgtcacga ctggatttgg cggatccgca    360

gacacccgca ccgaggacgc catctcgctc cagaaggctc tcctcgagca ccagctctgc    420

ggtgttctcc cttcgtcgtt cgactcgttc cgcctcggcc gcggtctcga gaactcgctt    480

cccctcgagg ttgttcgcgg cgccatgaca atccgcgtca acagcttgac ccgcggccac    540
```

```
tcggctgtcc gcctcgtcgt cctcgaggcg ctcaccaact tcctcaacca cggcatcacc     600

cccatcgtcc ccctccgcgg caccatctct gcgtcgggcg acctctctcc tctctcctac     660

attgcagcgg ccatcagcgg tcacccggac agcaaggtgc acgtcgtcca cgagggcaag     720

gagaagatcc tgtacgcccg cgaggcgatg gcgctcttca acctcgagcc cgtcgtcctc     780

ggcccgaagg aaggtctcgg tctcgtcaac ggcaccgccg tctcagcatc gatggccacc     840

ctcgctctgc acgacgcaca catgctctcg ctcctctcgc agtcgctcac ggccatgacg     900

gtcgaagcga tggtcggcca cgccggctcg ttccacccct tccttcacga cgtcacgcgc     960

cctcacccga cgcagatcga agtcgcggga aacatccgca agctcctcga gggaagccgc    1020

tttgctgtcc accatgagga ggaggtcaag gtcaaggacg acgagggcat tctccgccag    1080

gaccgctacc ccttgcgcac gtctcctcag tggctcggcc cgctcgtcag cgacctcatt    1140

cacgcccacg ccgtcctcac catcgaggcc ggccagtcga cgaccgacaa ccctctcatc    1200

gacgtcgaga acaagacttc gcaccacggc ggcaatttcc aggctgccgc tgtggccaac    1260

accatggaga agactcgcct cgggctcgcc cagatcggca agctcaactt cacgcagctc    1320

accgagatgc tcaacgccgg catgaaccgc ggcctcccct cctgcctcgc ggccgaagac    1380

ccctcgctct cctaccactg caagggcctc gacatcgccg ctgcggcgta cacctcggag    1440

ttgggacacc tcgccaaccc tgtgacgacg catgtccagc cggctgagat ggcgaaccag    1500

gcggtcaact cgcttgcgct catctcggct cgtcgcacga ccgagtccaa cgacgtcctt    1560

tctctcctcc tcgccaccca cctctactgc gttctccaag ccatcgactt gcgcgcgatc    1620

gagttcgagt tcaagaagca gttcggccca gccatcgtct cgctcatcga ccagcacttt    1680

ggctccgcca tgaccggctc gaacctgcgc gacgagctcg tcgagaaggt gaacaagacg    1740

ctcgccaagc gcctcgagca gaccaactcg tacgacctcg tcccgcgctg gcacgacgcc    1800

ttctccttcg ccgccggcac cgtcgtcgag gtcctctcgt cgacgtcgct ctcgctcgcc    1860

gccgtcaacg cctggaaggt cgccgccgcc gagtcggcca tctcgctcac ccgccaagtc    1920

cgcgagacct tctggtccgc cgcgtcgacc tcgtcgcccg cgctctcgta cctctcgccg    1980

cgcactcaga tcctctacgc cttcgtccgc gaggagcttg gcgtcaaggc ccgccgcgga    2040

gacgtcttcc tcggcaagca agaggtgacg atcggctcga acgtctccaa gatctacgag    2100

gccatcaagt cgggcaggat caacaacgtc ctcctcaaga tgctcgct                 2148
```

<210> SEQ ID NO 14
<211> LENGTH: 2129
<212> TYPE: DNA
<213> ORGANISM: Phanerochaete chrysosporium

<400> SEQUENCE: 14

```
atgccgcccc ttcaacagag cgcaagcccg aactcctgga caagttcgtc gaggcgtacg      60

acgagctgca atcctacagg gaaggcaagc cagtgatcgt cgacggacac aaccttagca     120

tccccgctgt cgcagcgacg gcgcgctttg gcgccgcggt ggccctcgac gagaaccccg     180

agacccacga gcgcgtcctg cagagcagac gcgtgattgt cgacaaggtc agcactcagc     240

gcagcgtata cggcgtcagc acgggcttcg gcggatccgg tacgttttgc gccgataccc     300

gcacaagcga cccgctccag ctcggccatg ccctcctcca gcaccagcac gtcggcgtgc     360

tgccgactca gaccgagtcg ccgctcccag ctctgcccct gggtgaccca ctcgcaacga     420

cgagcatgcc agaggcctgg gttcgtggtg caatccttat ccgcatgaac tcccttatcc     480

gggggcactc tggtgtccgt tgggagctta tcgagaagat gggcgagttg ctgcgcgaga     540
```

```
atatcacccc acttgttccc ctgcgcggca gcatctctgc ctcgggagat ctctcgccgc    600

tctcatacat tgccggaacg ctcattggca gcccggctat ccgtgtcttt gatggccccg    660

cctcctatgg agcccgccgc atcctgccct cgaatatcgc gctcgccaac cacggtgtag    720

ccccgatccc gctctcttcc aaggagcact tgggtattct caacggcaca gcattctccg    780

cgtcggtcgg cgcactggct ctcaatgagg ctgttcacct ttctcttctc gcgcaggtct    840

gcacggcaat gggcaccgaa gcgatgattg gtgcagttgg ctcgttcgac gcctttattc    900

acgataccgc tcgcccgcac cccggccaag tcgaggtcgc tcgcaacgtc cggactctcc    960

tcgaggactc gcagatggcg gtcaaggctg aggacgaagt tcacattgcc gaggatgagg   1020

gcgagctccg tcaggaccgc tacccactcc gcacggcggc acaattcctt ggcccccaga   1080

ttgaggacat cctgtctgcc cacgagacgg tcactcttga gtgcaactcg accaccgata   1140

accctcttat tgatggcgag actggcaccg tgcaccatgg tggtaacttc caggccatgg   1200

ctgtcacgaa cgcgatggag aagacccgcc ttgccattca ccacattggc aagctgctct   1260

ttgcccaggc aaccgagctc atcaacccca tgatgaaccg cggcctgcca cccaacctcg   1320

cggcgactga cccgtcccac aactacttcg ccaagggtat cgacattcac ctcgctgcct   1380

acgtcggcga gctcggcttc cttgccagcc cggtctcttc gcacatccag tccgcggaga   1440

tgcacaacca ggctgttaac tcgctcgccc tcgtgtctgc tcgctacacg atcagcgcgc   1500

tcgacgtcct ctctctcctc acggcggcgt acctttacgt cctctgccag gcgctcgacc   1560

tccgcgcgat gcacaacgac ctccagtcgt cgctctcggc gatcgtccgc gagctgctgc   1620

ccaagcattt cccgtctgcg gcgaagcgcg cggacgctct tttgcccatc ctcgagcgta   1680

ccatcttccg cgcactcaac tcctcgagct cggcagactg caaggcgcgc atggtcagcg   1740

tcgctgcctc gaccacgacg ccgctcgtcg acttcctctc tgcggacgct gcgctcgcat   1800

ccgagctcgc gaacatcact gccttccgca cggacctcgc gacgcgcgct gccgatgcac   1860

tcacgacgct gcgcacgcag taccttgagg gtgcccgtgg cgcggcacca gcgagcaagt   1920

acctcggcaa gacgcgccct gtgtacgagt tcgtgcgtgt caccctcaac gtgccgatgc   1980

acggccgcga gaacctgcac aacttcgaga tgggcccggg tgtcgaggac ggcatcatcg   2040

gcaacaacat ctcgacgatc tacgaggcca tccgcgacgg caagatgcag aacgtcgtca   2100

tgcagctcgt caagtctatc aaggcgtag                                     2129
```

<210> SEQ ID NO 15
<211> LENGTH: 2214
<212> TYPE: DNA
<213> ORGANISM: Artificial Sequence
<220> FEATURE:
<223> OTHER INFORMATION: Optimized coding region for Phanerochaete chrysosporium TAL

<400> SEQUENCE: 15

```
atgccgtccc gtatcgatta ctatacttct tctggtaacg gctacgcgca gagccgcaag     60

tcctccgcga tctacccggc tagcgcgtct accggtcatg ctgcaccgtc cacggagcgc    120

aagccggagc tgctggacaa gtttgttgaa gcgtatgatg aactgcagtc ttaccgtgaa    180

ggtaagccgg ttatcgttga cggccacaac ctgtctatcc cggcggtcgc tgctactgcg    240

cgttttggcg ctgctgtggt actggacgaa aacccggaaa ctcacgaacg tgtcctgcag    300

agccgccgtg tgattgtcga caaagtttct acccagcgtt ctgtatacgg cgttagcacc    360

ggcttcggcg gttccgctga cactcgcacc tctgacccgc tgcaactggg ccacgcgctg    420

ctgcagcacc aacacgtcgg tgttctgccg actcagactg aaagcccgct gccagccctg    480
```

```
ccactgggtg acccgctggc gaccacctct atgccggaag cgtgggttcg cggtgctatc    540

ctgattcgta tgaactctct gatccgtggt cactctggcg ttcgttggga actgattgag    600

aaaatgggtg agctgctgcg tgaaaacatt accccgctgg tcccgctgcg tggtagcatc    660

tctgctagcg gcgatctgtc tccgctgtcc tatatcgctg gcaccctgat tggttcccct    720

gccattcgtg tgttcgacgg tcctgcctct tacggtgcgc gtcgtatcct gccgtctaat    780

attgcgctgg ccaaccacgg tgtagcgccg atcccgctgt cttccaaaga acatctgggt    840

attctgaatg gtaccgcttt ttctgcctct gttggtgcac tggctctgaa cgaagctgtt    900

cacctgagcc tgctggcgca ggtatgcacc gcaatgggta ccgaagcgat gatcggcgca    960

gtgggcagct ttgatgcgtt catccacgat accgctcgtc cacacccggg ccaggtagag   1020

gttgcgcgta acgttcgtac cctgctggaa gactctcaga tggcagtcaa ggcagaagat   1080

gaagtacata ttgctgaaga tgagggtgag ctgcgccaag atcgttatcc gctgcgtacc   1140

gctgcgcagt tcctgggccc gcagatcgaa gacattctgt ctgcacacga gacggttacc   1200

ctggaatgta actccaccac ggacaatcca ctgatcgacg gcgaaactgg cacggtacat   1260

catggtggca actttcaagc tatggcggtt accaacgcaa tggagaaaac ccgtctggcg   1320

atccaccaca tcggcaaact gctgttcgcg caggccacgg aactgatcaa ccctatgatg   1380

aaccgcggcc tgccgccgaa cctggcagca accgacccta gccacaatta cttcgcaaaa   1440

ggtgttgata tccacctggc agcatacgtt ggcgagctgg gtttcctggc gagcccagtt   1500

tctagccaca tccagtccgc agaaatgcat aaccaggcag tgaactccct ggctctggtt   1560

tctgcgcgtt acaccatttc cgctctggat gtgctgtccc tgctgaccgc cgcatatctg   1620

tatgtcctgt gccaggccct ggatctgcgt gcgatgcaca acgatctgca gtcctctctg   1680

tccgccatcg ttcgtgaact gctgccgaag cattttccgt ctgcggctaa acgcgcagat   1740

gcactgctgc cgattctgga acgtaccatc ttccgcgcac tgaactcttc ttcctccgcg   1800

gactgcaaag cccgcatggt ttccgtggca gcttctacca ccaccccgct ggttgatttc   1860

ctgagcgccg acgctgccct ggcttccgaa ctggctaata ttactgcttt ccgtaccgaa   1920

ctggcgaccc gcgcagctga cgcactgacc accctgcgca cccagtacct ggaaggtgct   1980

cgcggtgccg cgccagcttc taaatatctg ggcaaaactc gtccggtata cgaatttgtg   2040

cgtgtgactc tgaacgtgcc gatgcatggc cgtgaaaatc tgcacaactt cgaaatgggt   2100

ccgggtgttg aggatggcat catcggcaac aacatctcca ctatctacga agccatccgt   2160

gatggtaaaa tgcagaacgt tgttatgcag ctggttaagt ctattaaagc ctaa         2214
```

<210> SEQ ID NO 16
<211> LENGTH: 40
<212> TYPE: DNA
<213> ORGANISM: Artificial Sequence
<220> FEATURE:
<223> OTHER INFORMATION: Primer for PCR amplification of the RgTAL coding region from plasmid pKK223-PAL

<400> SEQUENCE: 16

```
taacaggagg aattaaccat ggcaccctcg ctcgactcga                          40
```

<210> SEQ ID NO 17
<211> LENGTH: 30
<212> TYPE: DNA
<213> ORGANISM: Artificial Sequence
<220> FEATURE:
<223> OTHER INFORMATION: Primer for PCR amplification of the RgTAL coding region from plasmid pKK223-PAL

<400> SEQUENCE: 17
acagccaagc ttggctgcag gaggcagcca 30

<210> SEQ ID NO 18
<211> LENGTH: 42
<212> TYPE: DNA
<213> ORGANISM: Artificial Sequence
<220> FEATURE:
<223> OTHER INFORMATION: Primer for PCR amplification of the araC-araB region from E. coli strain FM5

<400> SEQUENCE: 18
gccattcagg ctgcgcatta tgacaacttg acggctacat ca 42

<210> SEQ ID NO 19
<211> LENGTH: 70
<212> TYPE: DNA
<213> ORGANISM: Artificial Sequence
<220> FEATURE:
<223> OTHER INFORMATION: Primer for PCR amplification of the araC-araB region from E. coli strain FM5

<400> SEQUENCE: 19
agccaagctt ggtacctccc ggggagctcc gaattcttcc tcctgttagc ccaaaaaacg 60
ggtatggaga 70

<210> SEQ ID NO 20
<211> LENGTH: 36
<212> TYPE: DNA
<213> ORGANISM: Artificial Sequence
<220> FEATURE:
<223> OTHER INFORMATION: Primer for PCR amplification of the transcription termination sequences rrnBT1 and rrnBT2 from plasmid pTrc99A (Pharmacia Biotech, Amersham, GE Healthcare, Piscataway, NJ)

<400> SEQUENCE: 20
gcttgaaagc ttggctgttt tggcggatga gagaag 36

<210> SEQ ID NO 21
<211> LENGTH: 50
<212> TYPE: DNA
<213> ORGANISM: Artificial Sequence
<220> FEATURE:
<223> OTHER INFORMATION: Primer for PCR amplification of the transcription termination sequences rrnBT1 and rrnBT2 from plasmid pTrc99A (Pharmacia Biotech, Amersham, GE Healthcare, Piscataway, NJ)

<400> SEQUENCE: 21
tcgggaattg aagcttaaga gtttgtagaa acgcaaaaag gccatccgtc 50

<210> SEQ ID NO 22
<211> LENGTH: 46
<212> TYPE: DNA
<213> ORGANISM: Artificial Sequence
<220> FEATURE:
<223> OTHER INFORMATION: Oligonucleotides encoding for a linker sequence added to pLH312

<400> SEQUENCE: 22
ctacaaactc ttggtacccc gtctagaact agtcaattcc cgacag 46

<210> SEQ ID NO 23
<211> LENGTH: 46
<212> TYPE: DNA

<213> ORGANISM: Artificial Sequence
<220> FEATURE:
<223> OTHER INFORMATION: Oligonucleotides encoding for a linker sequence added to pLH312

<400> SEQUENCE: 23
ctgtcgggaa ttgactagtt ctagacgggg taccaagagt ttgtag 46

<210> SEQ ID NO 24
<211> LENGTH: 53
<212> TYPE: DNA
<213> ORGANISM: Artificial Sequence
<220> FEATURE:
<223> OTHER INFORMATION: Primer for PCR amplification of the colE1 replication origin and rop (encodes a replication origin protein) gene locus of pBR322

<400> SEQUENCE: 24
ggacatcgca tgcgggttgc cttactggtt agcagaatga atcaccgata cgc 53

<210> SEQ ID NO 25
<211> LENGTH: 53
<212> TYPE: DNA
<213> ORGANISM: Artificial Sequence
<220> FEATURE:
<223> OTHER INFORMATION: Primer for PCR amplification of the colE1 replication origin and rop (encodes a replication origin protein) gene locus of pBR322

<400> SEQUENCE: 25
ggacatcgca tgcgggttgc cttactggtt agcagaatga atcaccgata cgc 53

<210> SEQ ID NO 26
<211> LENGTH: 30
<212> TYPE: DNA
<213> ORGANISM: Artificial Sequence
<220> FEATURE:
<223> OTHER INFORMATION: Primer for PCR amplification of the putative TAL encoding sequence from the cDNA of P. chrysosporium

<400> SEQUENCE: 26
gatcgaattc atgccgcccc ttcaacagag 30

<210> SEQ ID NO 27
<211> LENGTH: 31
<212> TYPE: DNA
<213> ORGANISM: Artificial Sequence
<220> FEATURE:
<223> OTHER INFORMATION: Primer for PCR amplification of the putative TAL encoding sequence from the cDNA of P. chrysosporium

<400> SEQUENCE: 27
gatcaagctt ctacgccttg atagacttga c 31

<210> SEQ ID NO 28
<211> LENGTH: 716
<212> TYPE: PRT
<213> ORGANISM: Rhodotorula glutinis mutant

<400> SEQUENCE: 28

Met Ala Pro Ser Leu Asp Ser Ile Ser His Ser Phe Ala Asn Gly Val
1 5 10 15

Ala Ser Ala Lys Gln Ala Val Asp Gly Ala Ser Thr Asn Leu Ala Val
20 25 30

Ala Gly Ser His Leu Pro Thr Thr Gln Val Thr Gln Val Asp Ile Val
35 40 45

```
Glu Lys Met Leu Ala Ala Pro Thr Asp Ser Thr Leu Glu Leu Asp Gly
    50                  55                  60

Tyr Ser Leu Asn Leu Gly Asp Val Val Ser Ala Ala Arg Lys Gly Arg
65                  70                  75                  80

Pro Val Arg Val Lys Asp Ser Asp Glu Ile Arg Ser Lys Ile Asp Lys
                85                  90                  95

Ser Val Glu Phe Leu Arg Ser Gln Leu Ser Met Ser Val Tyr Gly Val
            100                 105                 110

Thr Thr Gly Phe Gly Gly Ser Ala Asp Thr Arg Thr Glu Asp Ala Ile
        115                 120                 125

Ser Leu Gln Lys Ala Leu Leu Glu His Gln Leu Cys Gly Val Leu Pro
    130                 135                 140

Ser Ser Phe Asp Ser Phe Arg Leu Gly Arg Gly Leu Glu Asn Ser Leu
145                 150                 155                 160

Pro Leu Glu Val Val Arg Gly Ala Met Thr Ile Arg Val Asn Ser Leu
                165                 170                 175

Thr Arg Gly His Ser Ala Val Arg Leu Val Val Leu Glu Ala Leu Thr
            180                 185                 190

Asn Phe Leu Asn His Gly Ile Thr Pro Ile Val Pro Leu Arg Gly Thr
        195                 200                 205

Ile Ser Ala Ser Gly Asp Leu Ser Pro Leu Ser Tyr Ile Ala Ala Ala
    210                 215                 220

Ile Ser Gly His Pro Asp Ser Lys Val His Val Val His Glu Gly Lys
225                 230                 235                 240

Glu Lys Ile Leu Tyr Ala Arg Glu Ala Met Ala Leu Phe Asn Leu Glu
                245                 250                 255

Pro Val Val Leu Gly Pro Lys Glu Gly Leu Gly Leu Val Asn Gly Thr
            260                 265                 270

Ala Val Ser Ala Ser Met Ala Thr Leu Ala Leu His Asp Ala His Met
        275                 280                 285

Leu Ser Leu Leu Ser Gln Ser Leu Thr Ala Met Thr Val Glu Ala Met
    290                 295                 300

Val Gly His Ala Gly Ser Phe His Pro Phe Leu His Asp Val Thr Arg
305                 310                 315                 320

Pro His Pro Thr Gln Ile Glu Val Ala Gly Asn Ile Arg Lys Leu Leu
                325                 330                 335

Glu Gly Ser Arg Phe Ala Val His His Glu Glu Glu Val Lys Val Lys
            340                 345                 350

Asp Asp Glu Gly Ile Leu Arg Gln Asp Arg Tyr Pro Leu Arg Thr Ser
        355                 360                 365

Pro Gln Trp Leu Gly Pro Leu Val Ser Asp Leu Ile His Ala His Ala
    370                 375                 380

Val Leu Thr Ile Glu Ala Gly Gln Ser Thr Thr Asp Asn Pro Leu Ile
385                 390                 395                 400

Asp Val Glu Asn Lys Thr Ser His His Gly Gly Asn Phe Gln Ala Ala
                405                 410                 415

Ala Val Ala Asn Thr Met Glu Lys Thr Arg Leu Gly Leu Ala Gln Ile
            420                 425                 430

Gly Lys Leu Asn Phe Thr Gln Leu Thr Glu Met Leu Asn Ala Gly Met
        435                 440                 445

Asn Arg Gly Leu Pro Ser Cys Leu Ala Ala Glu Asp Pro Ser Leu Ser
    450                 455                 460

Tyr His Cys Lys Gly Leu Asp Ile Ala Ala Ala Ala Tyr Thr Ser Glu
465                 470                 475                 480
```

```
Leu Gly His Leu Ala Asn Pro Val Thr Thr His Val Gln Pro Ala Glu
                485                 490                 495

Met Ala Asn Gln Ala Val Asn Ser Leu Ala Leu Ile Ser Ala Arg Arg
            500                 505                 510

Thr Thr Glu Ser Asn Asp Val Leu Ser Leu Leu Leu Ala Thr His Leu
        515                 520                 525

Tyr Cys Val Leu Gln Ala Ile Asp Leu Arg Ala Ile Glu Phe Glu Phe
    530                 535                 540

Lys Lys Gln Phe Gly Pro Ala Ile Val Ser Leu Ile Asp Gln His Phe
545                 550                 555                 560

Gly Ser Ala Met Thr Gly Ser Asn Leu Arg Asp Glu Leu Val Glu Lys
                565                 570                 575

Val Asn Lys Thr Leu Ala Lys Arg Leu Glu Gln Thr Asn Ser Tyr Asp
            580                 585                 590

Leu Val Pro Arg Trp His Asp Ala Phe Ser Phe Ala Ala Gly Thr Val
        595                 600                 605

Val Glu Val Leu Ser Ser Thr Ser Leu Ser Leu Ala Ala Val Asn Ala
    610                 615                 620

Trp Lys Val Ala Ala Ala Glu Ser Ala Ile Ser Leu Thr Arg Gln Val
625                 630                 635                 640

Arg Glu Thr Phe Trp Ser Ala Ala Ser Thr Ser Ser Pro Ala Leu Ser
                645                 650                 655

Tyr Leu Ser Pro Arg Thr Gln Ile Leu Tyr Ala Phe Val Arg Glu Glu
            660                 665                 670

Leu Gly Val Lys Ala Arg Arg Gly Asp Val Phe Leu Gly Lys Gln Glu
        675                 680                 685

Val Thr Ile Gly Ser Asn Val Ser Lys Ile Tyr Glu Ala Ile Lys Ser
    690                 695                 700

Gly Arg Ile Asn Asn Val Leu Leu Lys Met Leu Ala
705                 710                 715
```

<210> SEQ ID NO 29
<211> LENGTH: 2151
<212> TYPE: DNA
<213> ORGANISM: Rhodotorula glutinis mutant

<400> SEQUENCE: 29

```
atggcaccct cgctcgactc gatctcgcac tcgttcgcaa acggcgtcgc atccgcaaag      60

caggctgtcg atggcgcctc gaccaacctc gcagtcgcag gctcgcacct gcccacaacc     120

caggtcacgc aggtcgacat cgtcgagaag atgctcgccg cgccgaccga ctcgacgctc     180

gaactcgacg gctactcgct caacctcgga gacgtcgtct cggccgcgag gaagggcagg     240

cctgtccgcg tcaaggacag cgacgagatc cgctcaaaga ttgacaaatc ggtcgagttc     300

ttgcgctcgc aactctccat gagcgtctac ggcgtcacga ctggatttgg cggatccgca     360

gacacccgca ccgaggacgc catctcgctc cagaaggctc tcctcgagca ccagctctgc     420

ggtgttctcc cttcgtcgtt cgactcgttc cgcctcggcc gcggtctcga gaactcgctt     480

cccctcgagg ttgttcgcgg cgccatgaca atccgcgtca acagcttgac ccgcggccac     540

tcggctgtcc gcctcgtcgt cctcgaggcg ctcaccaact tcctcaacca cggcatcacc     600

cccatcgtcc ccctccgcgg caccatctct gcgtcgggcg acctgtctcc tctctcctac     660

attgcagcgg ccatcagcgg tcacccggac agcaaggtgc acgtcgtcca cgagggcaag     720

gagaagatcc tgtacgcccg cgaggcgatg gcgctcttca acctcgagcc cgtcgtcctc     780
```

-continued

```
ggcccgaagg aaggtctcgg tctcgtcaac ggcaccgccg tctcagcatc gatggccacc    840

ctcgctctgc acgacgctca catgctctcg ctcctctcgc agtcgctcac ggccatgacg    900

gtcgaagcga tggtcggcca cgccggctcg ttccacccct tccttcacga cgtcacgcgc    960

cctcacccga cgcagatcga agtcgcggga aacatccgca agctcctcga gggaagccgc   1020

tttgctgtcc accatgagga ggaggtcaag gtcaaggacg acgagggcat tctccgccag   1080

gaccgctacc ccttgcgcac gtctcctcag tggctcggcc cgctcgtcag cgacctcatt   1140

cacgcccacg ccgtcctcac catcgaggcc ggccagtcga cgaccgacaa ccctctcatc   1200

gacgtcgaga acaagacttc gcaccacggc ggcaatttcc aggctgccgc tgtggccaac   1260

accatggaga agactcgcct cgggctcgcc cagatcggca agctcaactt cacgcagctc   1320

accgagatgc tcaacgccgg catgaaccgc ggcctcccct cctgcctcgc ggccgaagac   1380

ccctcgctct cctaccactg caagggcctc gacatcgccg ctgcggcgta cacctcggag   1440

ttgggacacc tcgccaaccc tgtgacgacg catgtccagc cggctgagat ggcgaaccag   1500

gcggtcaact cgcttgcgct catctcggct cgtcgcacga ccgagtccaa cgacgtcctt   1560

tctctcctcc tcgccaccca cctctactgc gttctccaag ccatcgactt gcgcgcgatc   1620

gagttcgagt tcaagaagca gttcggccca gccatcgtct cgctcatcga ccagcacttt   1680

ggctccgcca tgaccggctc gaacctgcgc gacgagctcg tcgagaaggt gaacaagacg   1740

ctcgccaagc gcctcgagca gaccaactcg tacgacctcg tcccgcgctg gcacgacgcc   1800

ttctccttcg ccgccggcac cgtcgtcgag gtcctctcgt cgacgtcgct ctcgctcgcc   1860

gccgtcaacg cctggaaggt cgccgccgcc gagtcggcca tctcgctcac ccgccaagtc   1920

cgcgagacct tctggtccgc cgcgtcgacc tcgtcgcccg cgctctcgta cctctcgccg   1980

cgcactcaga tcctctacgc cttcgtccgc gaggagcttg gcgtcaaggc ccgccgcgga   2040

gacgtcttcc tcggcaagca agaggtgacg atcggctcga acgtctccaa gatctacgag   2100

gccatcaagt cgggcaggat caacaacgtc ctcctcaaga tgctcgcttg a            2151
```